(12) United States Patent
Brandt et al.

(10) Patent No.: US 9,765,478 B2
(45) Date of Patent: Sep. 19, 2017

(54) TREATMENT OF BIOMASS TO DISSOLVE LIGNIN WITH IONIC LIQUID COMPOSITION

(75) Inventors: Agnieszka Brandt, London (GB); Richard J. Murphy, London (GB); David J. Leak, London (GB); Tom Welton, London (GB); Jason Hallett, London (GB)

(73) Assignee: Imperial Innovations Ltd, London (GB)

( * ) Notice: Subject to any disclaimer, the term of this patent is extended or adjusted under 35 U.S.C. 154(b) by 649 days.

(21) Appl. No.: 13/993,681

(22) PCT Filed: Dec. 15, 2011

(86) PCT No.: PCT/GB2011/001723
§ 371 (c)(1),
(2), (4) Date: Oct. 22, 2013

(87) PCT Pub. No.: WO2012/080702
PCT Pub. Date: Jun. 21, 2012

(65) Prior Publication Data
US 2014/0073016 A1    Mar. 13, 2014

(30) Foreign Application Priority Data

Dec. 15, 2010  (GB) .................................. 1021319.7
May 27, 2011   (GB) .................................. 1109119.6

(51) Int. Cl.
| | |
|---|---|
| *D21C 3/00* | (2006.01) |
| *D21C 3/06* | (2006.01) |
| C07G 1/00 | (2011.01) |
| D21C 3/04 | (2006.01) |
| D21C 3/14 | (2006.01) |
| D21C 3/20 | (2006.01) |

(52) U.S. Cl.
CPC .............. *D21C 3/003* (2013.01); *D21C 3/06* (2013.01); *C07G 1/00* (2013.01); *C12P 2201/00* (2013.01); *D21C 3/04* (2013.01); *D21C 3/14* (2013.01); *D21C 3/20* (2013.01)

(58) Field of Classification Search
CPC ...................................................... D21C 3/003
USPC ............ 435/99; 530/500; 162/76, 82, 83, 80
See application file for complete search history.

(56) References Cited

U.S. PATENT DOCUMENTS

| | | |
|---|---|---|
| 2,032,437 A | 3/1936 | Richter |
| 3,598,695 A | 8/1971 | Waterstradt |
| 4,462,865 A | 7/1984 | Walles |
| 2007/0215300 A1* | 9/2007 | Upfal ....................... D21C 3/20 |
| | | 162/29 |
| 2010/0081798 A1 | 4/2010 | Balensiefer |
| 2012/0010334 A1* | 1/2012 | D'Andola ............ C07D 487/04 |
| | | 524/35 |

FOREIGN PATENT DOCUMENTS

| | | |
|---|---|---|
| WO | 90/11401 A1 | 10/1990 |
| WO | 98/49390 A1 | 11/1998 |
| WO | 2005/017001 A1 | 2/2005 |
| WO | 2005/017252 A1 | 2/2005 |
| WO | 2006/108861 A2 | 10/2006 |
| WO | WO 2008073186 A2 * | 6/2008 ............... C08H 8/00 |
| WO | 2008/090155 A1 | 7/2008 |
| WO | 2008/090156 A1 | 7/2008 |
| WO | 2008/112291 A2 | 9/2008 |
| WO | 2010/056790 A1 | 5/2010 |
| WO | WO 2010056790 A1 * | 5/2010 ............. D21C 3/006 |

OTHER PUBLICATIONS

Brandt et al., "The effect of the ionic liquid anion in the pretreatment of pine wood chips", Green Chemistry, 2010, vol. 12, 672-679.
Fu et al., "Lignin Extraction from Straw by Ionic Liquids and Enzymatic Hydrolysis of the Cellulosic Residues," J. Agric. Food Chem., 2010, 58, 2915-2922.

* cited by examiner

*Primary Examiner* — Scott Long
*Assistant Examiner* — Nghi Nguyen
(74) *Attorney, Agent, or Firm* — McDonnell Boehnen Hulbert & Berghoff LLP

(57) ABSTRACT

The present invention relates to a method for treating a lignocellulose biomass in order to dissolve the lignin therein, while the cellulose does not dissolve. The cellulose pulp obtained can be used to produce glucose. In addition the lignin can be isolated for subsequent use in the renewable chemical industry as a source for aromatic platform chemicals.

19 Claims, 32 Drawing Sheets

TREATMENT OF BIOMASS TO DISSOLVE LIGNIN WITH IONIC LIQUID COMPOSITION

CROSS-REFERENCE TO RELATED APPLICATIONS

This Application is a National Stage application under 35 U.S.C. §371 of International Patent Application no. PCT/GB2011/001723, filed Dec. 15, 2011, which claims the benefit of priority of United Kingdom Patent Applications nos. GB1021319.7, filed Dec. 15, 2010, and GB1109119.6, filed May 27, 2011.

BACKGROUND OF THE INVENTION

1. Field of the Invention

The present invention relates to a method for treating a lignocellulose biomass in order to dissolve the lignin therein, while the cellulose does not dissolve. The cellulose pulp obtained can be used to produce glucose. In addition the lignin can be isolated for subsequent use in the renewable chemical industry as a source for aromatic platform chemicals.

2. Description of Related Art

Biofuels can be generated by fermenting sugars to produce bioethanol. Currently biofuels are generally derived from food resources. This leads to several problems as there is competition with the food supply for the raw materials; the yield is low per unit area of land and a high energy input is required to grow the crops. It is possible to produce the sugar required by hydrolysing starch, or the sucrose produced by plants like sugar cane or sugar beet can be used. The problems could be alleviated if the woody part of plants from agricultural residues, forestry residues and energy crops could be used.

The woody or structural parts of the plant have evolved to withstand degradation. They are made up of mainly cellulose, hemicellulose and lignin. Pretreatment of the material is required in order to break up the structure. Generally pretreatment involves one or more of the following: removing the hemicelluose; modifying and solubilising the lignin; hydrolysing the hemicellulose-lignin linkages; and reducing the crystallinity of the cellulose fibres. This makes the cellulose more accessible to enzymes, and also removes potential inhibitors of the fermentation stage.

Several pretreatment strategies have been previously described. These include steam explosion, catalysis with dilute acid or a base, ammonia fibre expansion, Organosolv pulping and biological pretreatment. All of these processes have their disadvantages. Pretreatment with ionic liquids has also been described. Ionic liquids (ILs) are salts that are liquid at the temperature of interest. The combination of anions and cations can be chosen to match the particular application required.

WO10/0056790 describes the use of substantially water free ILs to dissolve biomass which can then be separated using various solvents. WO08/090155 and WO08/090156 both describe the use of ILs to dissolve all the biomass components e.g. the lignin, hemicellulose and cellulose. In these methods the cellulose is separated from the other components usually by adding a suitable solvent so that the cellulose precipitates out and can be separated. Two recent reports applying $[MeSO_4]^-$ containing ionic liquids for biomass pretreatment concluded that the ionic liquid is not capable of enhancing the digestibility of neither maple wood nor corn cob.

WO2008/112291 describes the use of ionic liquids to pretreat a lignin containing biomass to increase the yield in a subsequent saccharification reaction. The IL is used to swell the biomass structure and not achieve any dissolution of the lignocellulose. Lignin can be recovered as a post-saccharification solid.

US2010-0081798 describes the use of ILs containing a polyatomic anion to solubilise lignocellulose. The cellulose dissolves in the IL.

WO2005/017252 discloses the use of ILs with an aromatic anion to dissolve the lignin from biomass allowing the cellulosic fibres obtained to be further processed.

SUMMARY OF THE INVENTION

Many of the prior art processes require the ionic liquid to be substantially water free so that the biomass dissolves. Therefore the IL and the biomass have to be dried before use which adds to the processing costs. A tolerance of up to 15% water by weight in ILs has been reported, but higher levels produced unwanted results, such as precipitation of dissolved cellulose and reduced saccharification yields.

The pretreatment process could be improved by reducing the processing required to obtain the desired cellulose product. In addition methods which allow the lignin to be isolated and used would also be desirable.

Lignin is produced by current technologies (e.g. paper pulping) and is burned as a source of heat and electricity for the process (in paper pulping it even creates surplus electricity which is fed into the grid). However, if it was available in a purer form it could be used as the source of aromatic platform chemicals (containing a benzene ring) for a biorefinery (chemical value chain based on renewable resources). It could also be used with less modification as polymer additive (e.g. UV stabiliser) or wood adhesive.

The present inventors have identified a process where the lignin but not the cellulose is dissolved by an IL, so that the cellulose pulp produced can be mechanically separated before undergoing saccharification. The lignin can also be precipitated out from the IL by simply adding an anti-solvent, such as water. This means that the IL can be recycled. The present invention relates to a method of treating a lignocellulosic biomass to dissolve the lignin therein, but not the cellulose comprising:

(a) contacting the lignocellulose biomass with a composition comprising an ionic liquid to produce a cellulose pulp, wherein the ionic liquid comprises a cation and an anion selected from $C_{1-20}$ alkylsulfate [Alkyl $SO_4$]$^-$, $C_{1-20}$ alkylsulfonate [Alkyl $SO_3$]$^-$, hydrogensulfate [$HSO_4$]$^-$, hydrogen sulphite [$HSO_3$]$^-$, dihydrogen phosphate [$H_2PO_4$]$^-$, hydrogen phosphate [$HPO_4$]$^{2-}$ and acetate, with the proviso that if the anion is acetate then the composition further comprises 10-40% v/v water.

The IL is preferably heated with the biomass at 100-160° C., preferably 120-140° C. The reaction is carried out for 1-22 hours, preferably 1-13 hours, more preferably 1-8 hours. Preferably the mixture is stirred.

As used herein the term "lignocellulosic biomass" refers to living or dead biological material that can be used in one or more of the disclosed processes. It can comprise any cellulosic or lignocellulosic material and includes materials comprising cellulose, and optionally further comprising hemicellulose, lignin, starch, oligosaccharides and/or monosaccharides, biopolymers, natural derivatives of biopolymers, their mixtures, and breakdown products. It can also comprise additional components, such as protein and/or lipid. The biomass can be derived from a single source, or it can comprise a mixture derived from more than one source. Some specific examples of biomass include, but are not limited to, bioenergy crops, agricultural residues, municipal solid waste, industrial solid waste, sludge from paper manufacture, yard waste, wood and forestry waste. Additional examples of biomass include, but are not limited to, corn grain, corn cobs, crop residues such as corn husks, corn stover, grasses including *Miscanthus×giganteus*, wheat, wheat straw, hay, rice straw, switchgrass, waste paper, sugar cane bagasse, sorghum, soy, components obtained from milling of grains, trees (e.g. pine), branches, roots, leaves, wood chips, wood pulp, sawdust, shrubs and bushes, vegetables, fruits, flowers, animal manure, multi-component feed, and crustacean biomass (i.e., chitinous biomass). It may be preferable to treat the biomass before use in the method of the invention. For example the biomass could be mechanically treated e.g. milling or shredding.

In a preferred embodiment the biomass is contacted with the ionic liquid composition prior to mechanical treatment. It has been found that treating the biomass, supplied as wood chips can reduce the energy required to grind the biomass. The IL composition appears to work as a lubricant during the grinding phase. The lignocellulosic biomass, supplied as wood chips, can be briefly impregnated with an IL composition at slightly elevated temperature (70-100° C., preferably 90° C.) to harness their lubrication properties before a mechanical size reduction step is applied. The IL composition can be contacted with the biomass for any length of time from several minutes to 18 hours or longer, preferably 5 minutes to 1 hour. This can be followed by further treatment with an ionic liquid composition as described herein to further solubilise the lignin content of the biomass.

As used herein "ionic liquid" refers to an ionized species (i.e. cations and anions). Typically they have a melting point below about 100° C. The anion is selected from $C_{1-20}$ alkyl sulfate [Alkyl $SO_4$]$^-$, $C_{1-20}$ alkylsulfonate [Alkyl $SO_3$]$^-$, hydrogen sulfate [$HSO_4$]$^-$, hydrogen sulphite [$HSO_3$]$^-$, dihydrogen phosphate [$H_2PO_4$]$^-$, hydrogen phosphate [$HPO_4$]$^{2-}$ and acetate [$MeCO_2$], with the proviso that if the anion is acetate then the composition comprises 10-40% v/v water. Preferably the anion is selected from methyl sulfate [$MeSO_4$]$^-$, hydrogen sulfate [$HSO_4$]$^-$, methanesulfonate [$MeSO_3$]$^-$, and acetate [$MeCO_2$].

The lignin in the lignocellulosic biomass is soluble in the ionic liquid at the treatment temperature, but the cellulose is not, so that a pulp comprising the cellulose is produced. Other components such as hemicellulose may preferably also dissolve in the ionic liquid.

The cation is preferably a protic cation ion i.e they are capable of donating an $H^+$ (proton).

The cation ion can be an ammonium or phosphonium derivative. These cations have the general formula

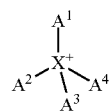

wherein
X is N or P; and
$A^1$ to $A^4$ are each independently selected from H, an aliphatic, $C_{3-6}$ carbocycle, $C_{6-10}$ aryl, alkylaryl, and heteroaryl.

The term "aliphatic" as used herein refers to a straight or branched chain hydrocarbon which is completely saturated or contains one or more units of unsaturation. Thus, aliphatic may be alkyl, alkenyl or alkynyl, preferably having 1 to 12 carbon atoms, preferably up to 6 carbon atoms or more preferably up to 4 carbon atoms. The aliphatic can have 1, 2, 3, 4, 5, 6, 7, 8, 9, 10, 11, or 12 carbon atoms.

The term "alkyl" as used herein, is typically a linear or branched alkyl group or moiety containing from 1 to 20 carbon atoms, such as 11, 12, 13, 14, 15, 16, 17, 18, or 19 carbon atoms. Preferably the alkyl group or moiety contains 1-10 carbon atoms i.e 2, 3, 4, 5, 6, 7, 8, 9, or 10 carbon atoms such as a $C_{1-4}$ alkyl or a $C_{1-6}$ alkyl group or moiety, for example methyl, ethyl, n-propyl, i-propyl, n-butyl, i-butyl and t-butyl, n-pentyl, methylbutyl, dimethylpropyl, n-hexyl, 2-methylpentyl, 3-methylpentyl, 2,3-dimethylbutyl, and 2,2-dimethylbutyl.

The term "carbocycle" as used herein refers to a saturated or partially unsaturated cyclic group having 3 to 6 ring carbon atoms, i.e. 3, 4, 5, or 6 carbon atoms. A carbocycle is preferably a "cycloalkyl", which as used herein refers to a fully saturated hydrocarbon cyclic group. Preferably, a cycloalkyl group is a $C_3$-$C_6$ cycloalkyl group.

The term "$C_{6-10}$ aryl group" used herein means an aryl group constituted by 6, 7, 8, 9 or 10 carbon atoms and includes condensed ring groups such as monocyclic ring group, or bicyclic ring group and the like. Specifically, examples of "$C_{6-10}$ aryl group" include phenyl group, indenyl group, naphthyl group or azulenyl group and the like. It should be noted that condensed rings such as indan and tetrahydro naphthalene are also included in the aryl group.

The terms "alkylaryl" as used herein refers to an alkyl group as defined below substituted with an aryl as defined above. The alkyl component of an "alkylaryl" group may be substituted with any one or more of the substituents listed above for an aliphatic group and the aryl or heteroaryl component of an "alkylaryl" or "alkylheteroaryl" group may be substituted with any one or more of the substituents listed above for aryl, and carbocycle groups. Preferably, alkylaryl is benzyl.

The term "heteroaryl" as used herein refers to a monocyclic or bicyclic aromatic ring system having from 5 to 10 ring atoms, i.e. 5, 6, 7, 8, 9, or 10 ring atoms, at least one ring atom being a heteroatom selected from O, N or S.

An aryl, heteroaryl, or carbocycle group as referred to herein may be unsubstituted or may be substituted by one or more substituents independently selected from the group consisting of halo, lower alkyl, —$NH_2$, —$NO_2$, —OH —COOH, or —CN.

The term "halogen atom" or "halo" used herein means a fluorine atom, a chlorine atom, a bromine atom, an iodine atom and the like, preferably a fluorine atom or a chlorine atom, and more preferably a fluorine atom.

The cation can also contain a nitrogen-containing heterocyclic moiety which, as used herein, refers to mono- or bicyclic ring systems which include one nitrogen atom and optionally one or more further heteroatoms selected from N, S and O. The ring systems contain 5-9 members, preferably 5 or 6 members for monocyclic groups, and 9 or 10 members for bicyclic groups. The rings can be aromatic, partially saturated or saturated and thus, includes both a "heteroalicyclic" group, which means a non-aromatic heterocycle and a "heteroaryl" group, which means an aromatic heterocycle. The cation is preferably selected from

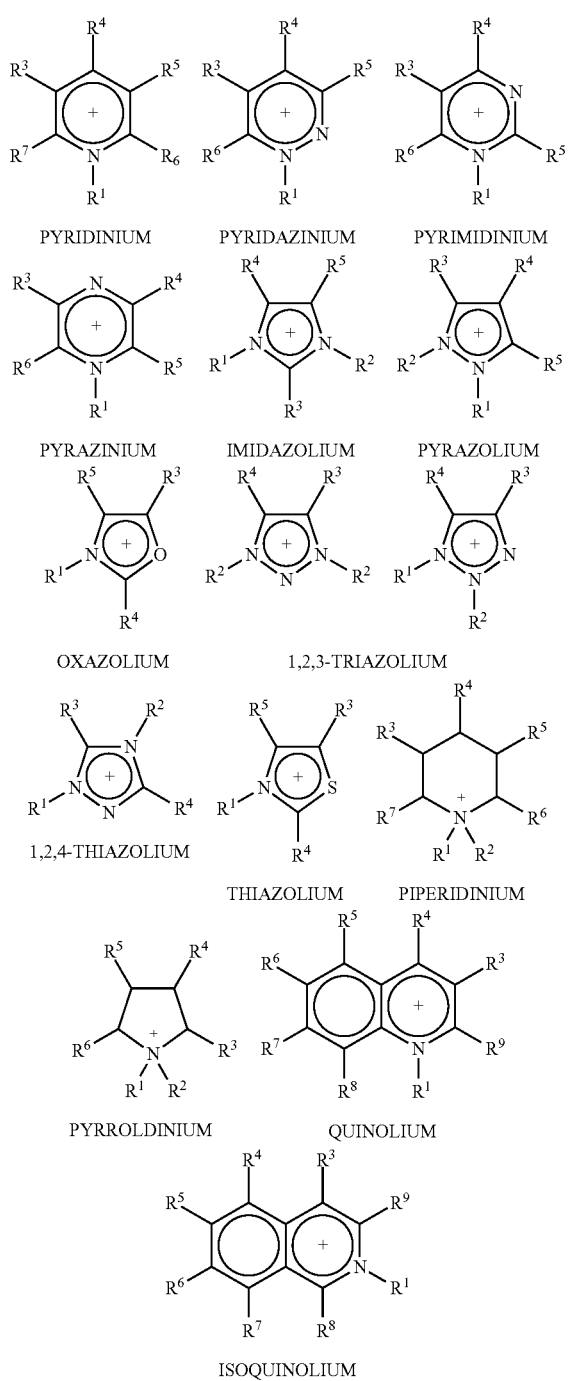

wherein $R^1$ and $R^2$ are independently a $C_{1-6}$ alkyl or a $C_{1-6}$ alkoxyalkyl group, and $R^3$, $R^4$, $R^5$, $R^6$, $R^7$, $R^8$ and $R^9$, when present are independently H, a $C_{1-6}$ alkyl, $C_{1-6}$ alkoxyalkyl group, or $C_{2-6}$ alkyoxy group. Preferably $R^1$ and $R^2$ are $C_{1-4}$ alkyl, with one being methyl and $R^3$-$R^9$, ($R^3$, $R^4$, $R^5$, $R^6$, $R^7$, $R^8$ and $R^9$), when present, are H. Preferably the cation ring is imidazolium or pyridinium.

"$C_{2-6}$ Alkoxy" refers to the above $C_{1-6}$ alkyl group bonded to an oxygen that is also bonded to the cation ring. A "$C_{2-6}$ alkoxyalkyl group" refers to an alkyl containing an ether group, with the general formula X—O—Y wherein X and Y are each independently a $C_{1-5}$ alkyl and the total number of carbon atoms is between 2 and 6 e.g. 2, 3, 4, 5, or 6.

As used here in the term "alkenyl" refers to a linear or branched alkenyl group or moiety containing from 2 to 20 carbon atoms, such as 11, 12, 13, 14, 15, 16, 17, 18, or 19 carbon atoms. Preferably the alkyl group or moiety contains 2-10 carbon atoms i.e 3, 4, 5, 6, 7, 8, 9, or 10 carbon atoms such as a $C_{2-4}$ alkenyl or a $C_{2-6}$ alkenyl group or moiety, for example ethenyl, 2-propenyl, 1-propenyl.

Preferably the cation ion is selected from 1-butyl-3-methylimidazolium $[C_4C_1im]^+$, 1-ethyl-3-methylimidazolium $[C_2C_1im]^+$, 1-methylimidazolium $[C_1Him]^+$ and 1-butylimidazolium $[C_4Him]^+$.

Preferred ionic liquids for use in the invention are 1-butyl-3-methylimidazolium methyl sulfate $[C_4C_1im][MeSO_4]$, 1-butyl-3-methylimidazolium hydrogen sulfate $[C_4C_1im][HSO_4]$, 1-butyl-3-methylimidazolium methanesulfonate $[C_4C_1im][MeSO_3]$, 1-butylimidazolium hydrogen sulfate $[C_4Him][HSO_4]$, and 1-ethyl-3-methylimidazolium acetate $[C_2C_1im][MeCO_2]$.

Ionic liquids can be prepared by methods known to the person skilled in the art or obtained commercially.

It has been surprisingly found that the yield in the saccharification step can be improved if the pretreatment composition comprises water. Therefore in one preferred embodiment the composition comprises the IL and 10-40% v/v water. Preferably the composition comprises 20-30% v/v water.

It has also been discovered that the presence of an excess of acid improves the glucose and hemicellulose yield. Therefore in one preferred embodiment the composition further comprises 0.01-20% v/v acid, preferably 1-5% v/v acid. The addition of a small amount of acid significantly accelerates the pre-treatment process, when other variable such as water content and temperature are kept constant. The acid can be selected from any known strong acid such as hydrochloric acid, sulphuric acid, nitric acid, phosphoric acid hydroiodic acid, perchloric acid and hydrobromic acid. Preferably the acid is Sulphuric or phosphoric acid.

The ionic liquids of the present invention dissolve the lignin within the biomass but unlike ILs described previously they do not dissolve the cellulose. The majority of cellulose remains solid, preferably at least 90%, more preferably 95%. It can be easily removed from the liquid phase mechanically, for example by filtration. The separated pulp can then be washed and used in the saccharification process. This removes the need for a separate precipitation step to obtain the cellulose once the biomass has been treated. Thus in a preferred embodiment the method of the invention further comprises the step of separating the ionic liquid from the pulp produced.

In a preferred embodiment the pulp is washed with an organic solvent miscible with the ionic liquid. The separation efficiency and the ionic liquid recovery can be enhanced by washing the pulp with an organic solvent that is miscible with the ionic liquid. The organic solvent is removed before or potentially after the lignin is precipitated. Examples of suitable organic solvents include aliphatic alcohols such as methanol and ethanol.

It is possible to precipitate out the lignin dissolved in the IL compositions. Therefore in another preferred embodiment the method further comprises (c) adding an anti-solvent to the ionic liquid which has been separated from the pulp, to precipitate out the dissolved lignin; and (d) separating the precipitated solid from the anti-solvent/ionic liquid.

As used herein an "anti-solvent" is a liquid which causes the lignin to precipitate out from the ionic liquid containing the solubilised lignin produced in step (a). The anti-solvent is preferably water. The ionic liquid can be recovered by removing the anti-solvent, for example by evaporation. The resulting ionic liquid can then be recycled to be used again in the method. Thus in another embodiment the method further comprises (e) removing the anti-solvent from the ionic liquid obtained in (d). As the presence of some water improves the yield less energy is required to dry the IL.

The cellulose pulp obtained from the method of the invention can be used to undergo saccharification to obtain glucose. This can then be used in the fermentation process to obtain biofuel. Thus in a second aspect the invention provides a process of preparing glucose from a lignocellulose biomass comprising subjecting a cellulose pulp obtainable by suitable methods of the invention to enzymatic hydrolysis. In a further aspect the invention provides glucose obtained by this hydrolysis.

Suitable enzymes for use in the process include commercially available preparations of cellulases such as *T. reseei* cellulase and Novozyme 188 cellobiase that also contains hemicellulolytic activity. Other useful enzymes include esterases, either acetyl esterases or feruloyl esterases, which cleave substituents that are esterified to hemicellulose. The process is preferably carried out in an aqueous medium at a suitable pH for the enzymes. The conditions can be optimised in relation to pH, temperature and the medium used depending on the enzyme mixture required. Such methods are well known to the skilled person. The process is preferably carried out in accordance with "Enzymatic saccharification of lignocellulosic biomass" (NREL/TP-510-42629), issue date Mar. 21, 2008.

In a further aspect the invention relates to lignin obtained by suitable methods as described herein.

Figure 25:
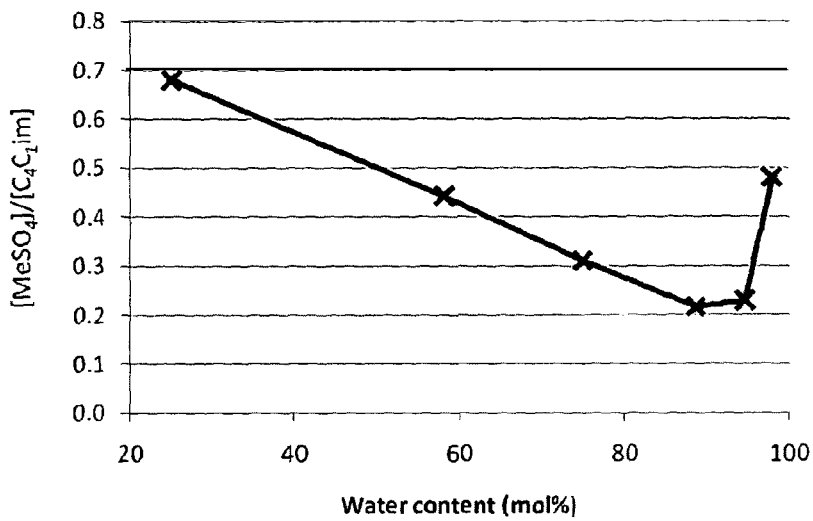

FIG. 25 shows the ratio of [MeSO$_4$]$^-$ anions to ionic liquid cations in the recycled ionic liquid after pretreatment of *Miscanthus* (detected by $^1$H-NMR), the remaining anions being [HSO$_4$]$^-$.

Figure 26:
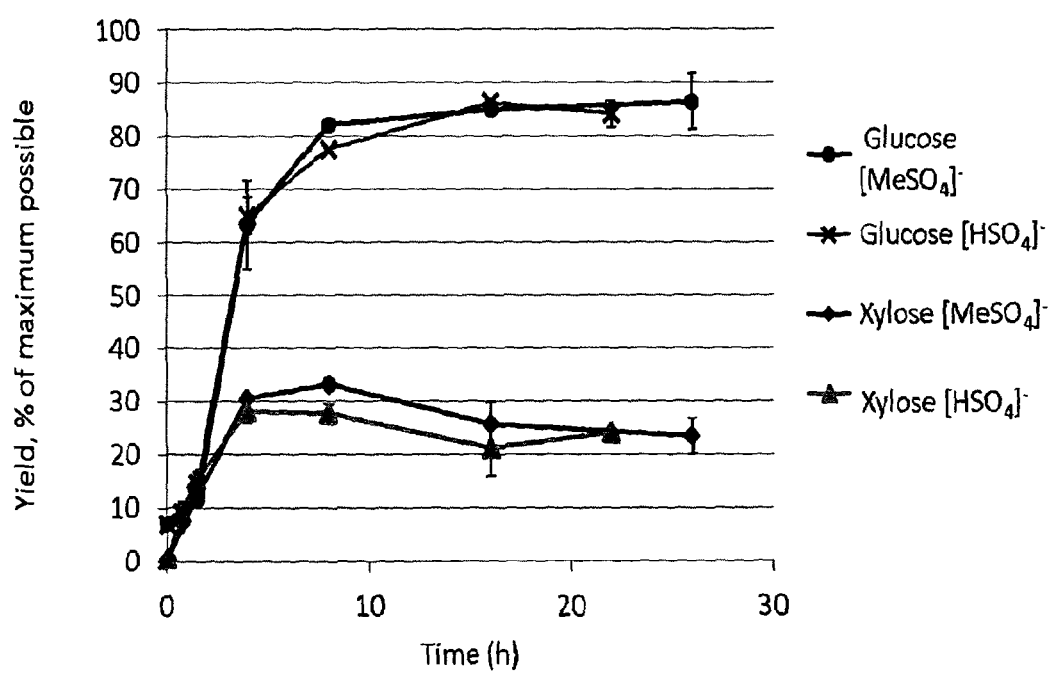

FIG. 26 shows the glucose and hemicellulose yields after enzymatic hydrolysis of *Miscanthus* pretreated with [C$_4$C$_1$im][MeSO$_4$]$_{80\%}$ and [C$_4$C$_1$im][HSO$_4$]$_{80\%}$ at 120° C. The yields are based on the glucan and hemicellulose content of the untreated biomass.

Figure 27:
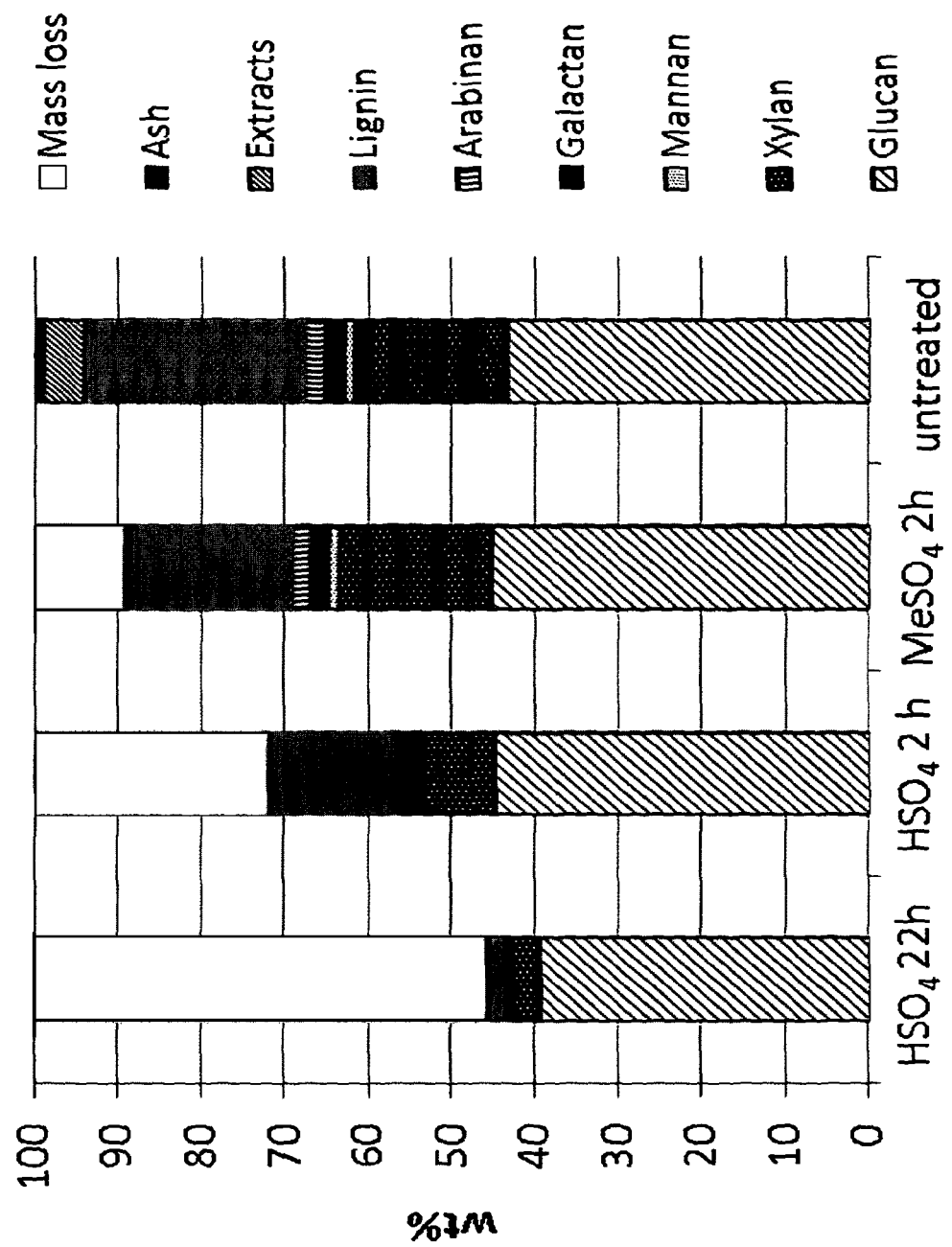

FIG. 27 shows the composition of *Miscanthus* before and after pretreatment with [C$_4$C$_1$im][HSO$_4$]$_{80\%}$ and [C$_4$C$_1$im][MeSO$_4$]$_{80\%}$ at 120° C. for 2 h or 22 h.

Figure 28:
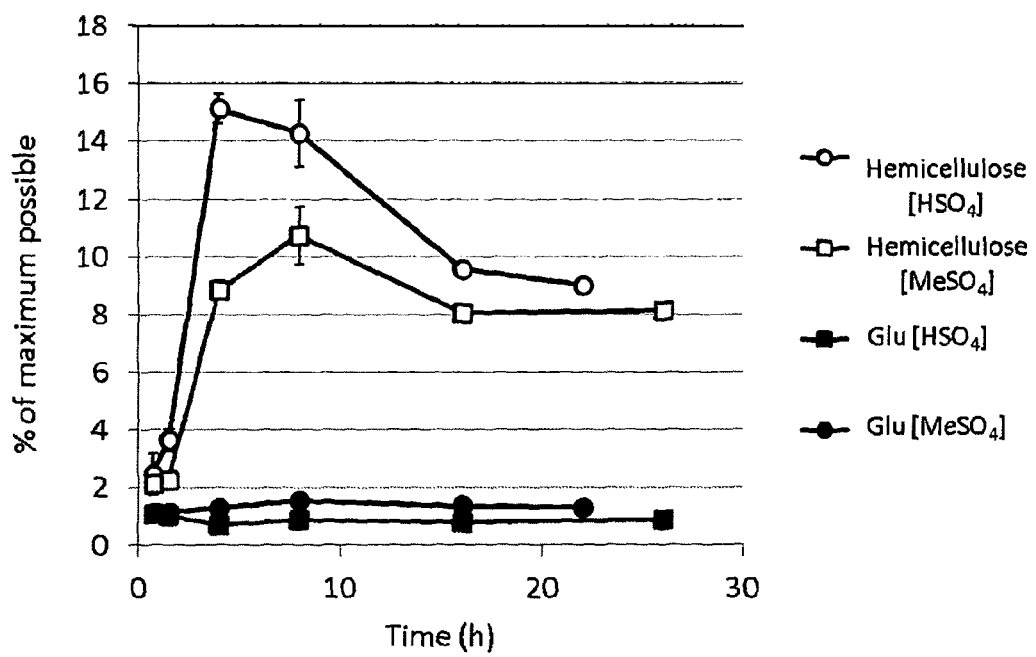

FIG. 28 shows the amount of glucose and hemicellulose monomers found in [C$_4$C$_1$im][HSO$_4$]$_{80\%}$ and [C$_4$C$_1$im][MeSO$_4$]$_{80\%}$ liquors during pretreatment at 120° C. The yields are based on the glucan and hemicellulose content of the untreated biomass.

Figure 29:
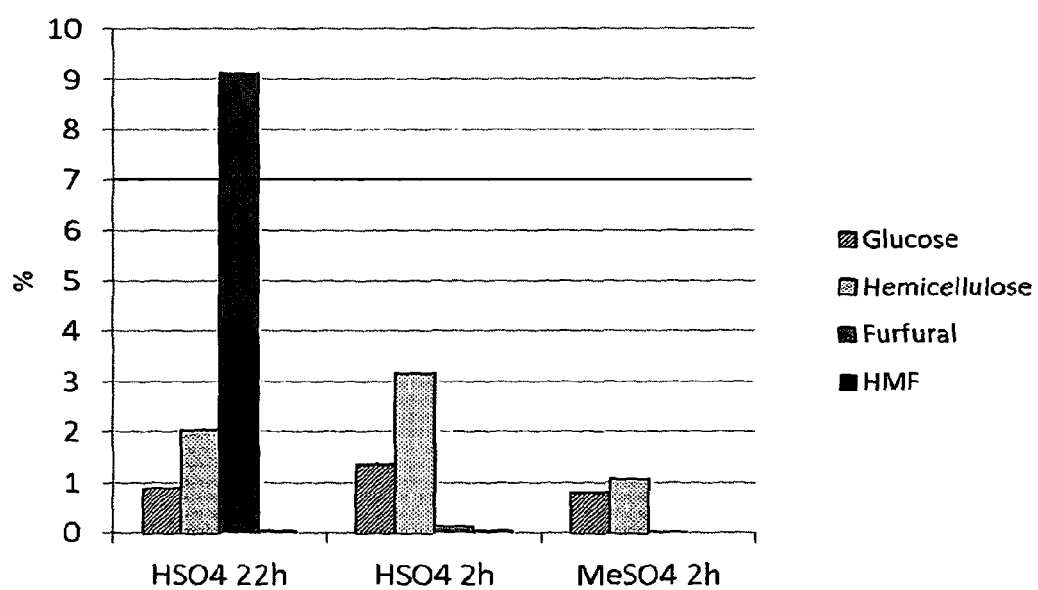

FIG. 29 shows the solubilised carbohydrates (monomers only) and the fraction converted to furfural after pretreatment with [C$_4$C$_1$im][HSO$_4$]$_{80\%}$ and [C$_4$C$_1$im][MeSO$_4$]$_{80\%}$ liquors. The yields are based on the glucan and hemicellulose content of the untreated biomass.

Figure 30:
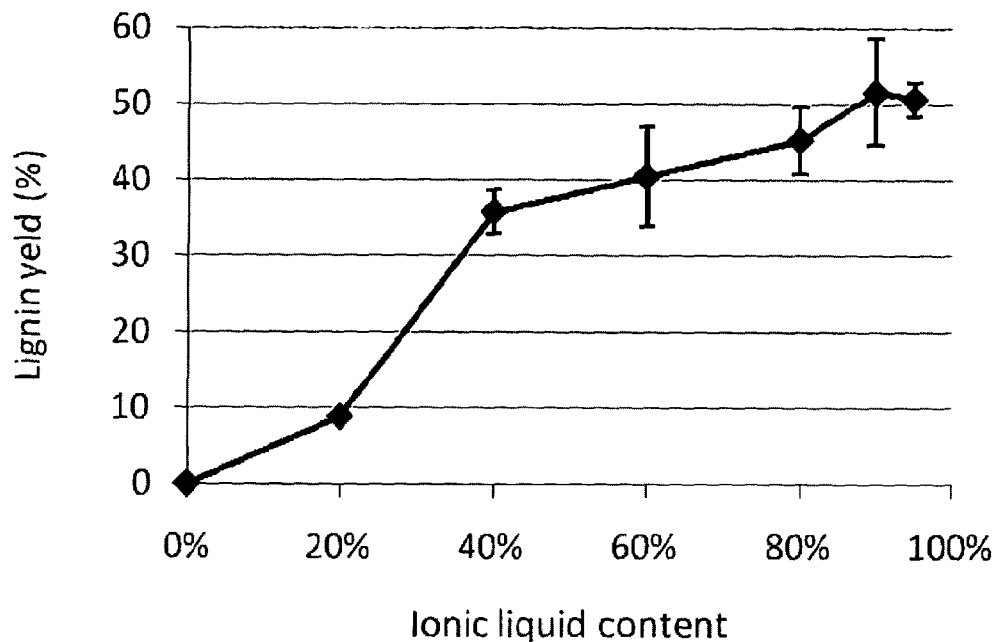

FIG. 30 shows the yield of precipitate (relative to Klason-lignin content of the untreated biomass) after pretreatment of *Miscanthus* with [C$_4$C$_1$im][HSO$_4$] water mixtures at 120° C. for 13 h.

Figure 31:
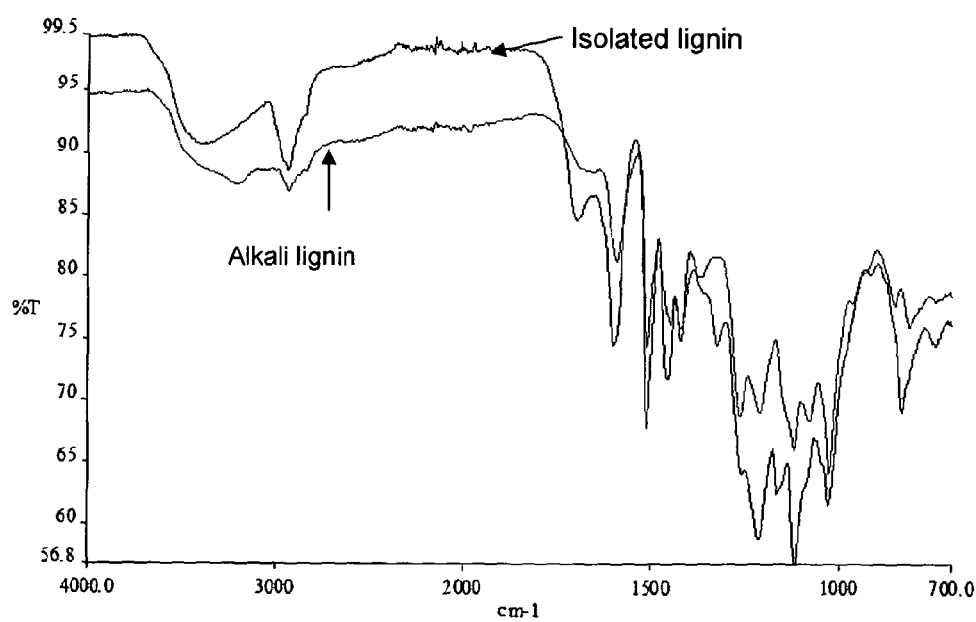

FIG. 31 shows IR spectra of lignin isolated from *Miscanthus* treated with [C$_4$C$_1$im][HSO$_4$]$_{80\%}$ for 22 h (black) and alkali lignin (from Aldrich, red).

Figure 32:
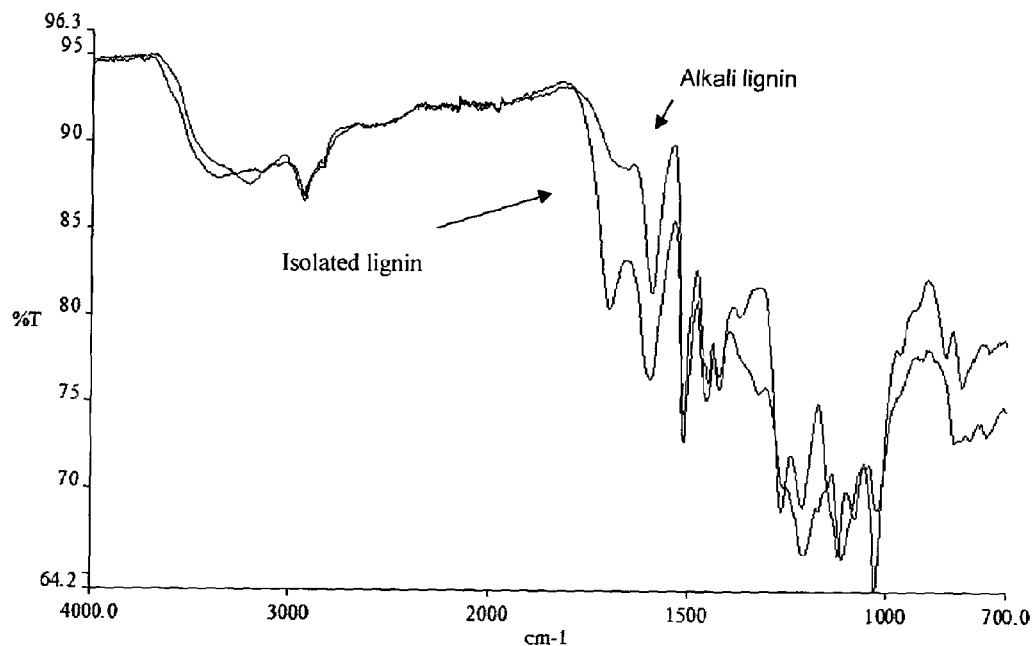

FIG. 32 shows IR spectra of lignin isolated from *Miscanthus* treated with [C$_4$Him][HSO$_4$]$_{80\%}$ for 20 h (blue) and alkali lignin (from Aldrich, red)

Figure 33:
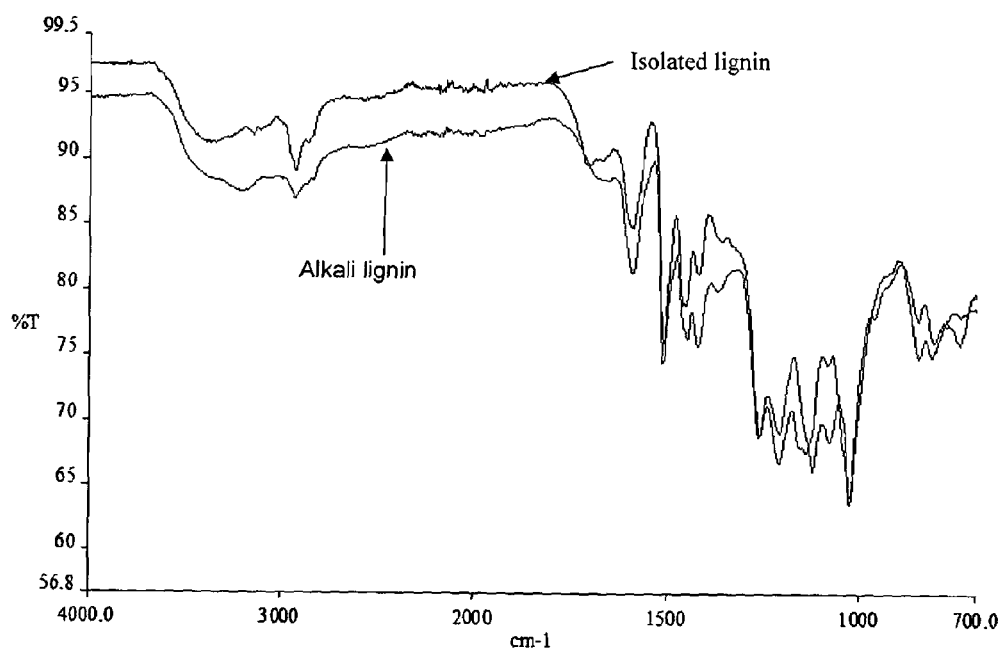

FIG. 33 shows IR spectra of lignin isolated from pine treated with [C$_4$C$_1$im][HSO$_4$]$_{80\%}$ for 22 h (blue) and alkali lignin (from Aldrich, red).

Figure 34:
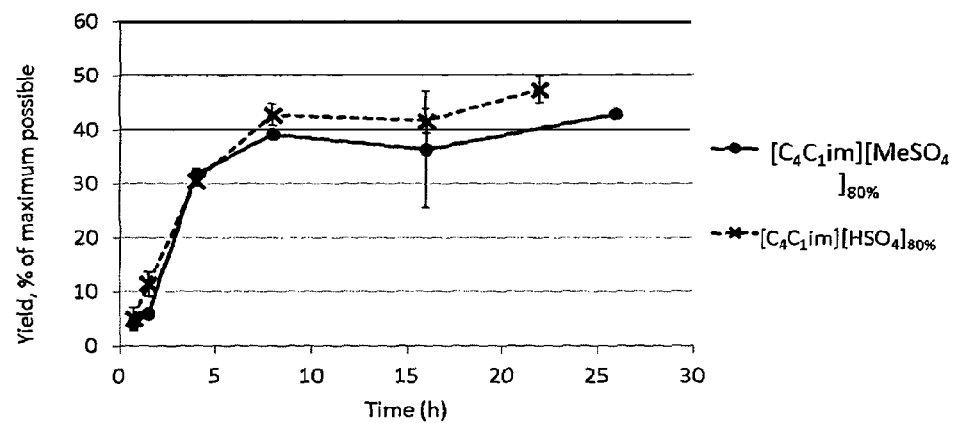

FIG. 34 shows the time course of lignin recovery after pretreatment of *Miscanthus* with [C$_4$C$_1$im][MeSO$_4$]$_{80\%}$ and [C$_4$C$_1$im][HSO$_4$]$_{80\%}$ at 120° C. The lignin was isolated from the liquor by precipitation with water.

Figure 35:
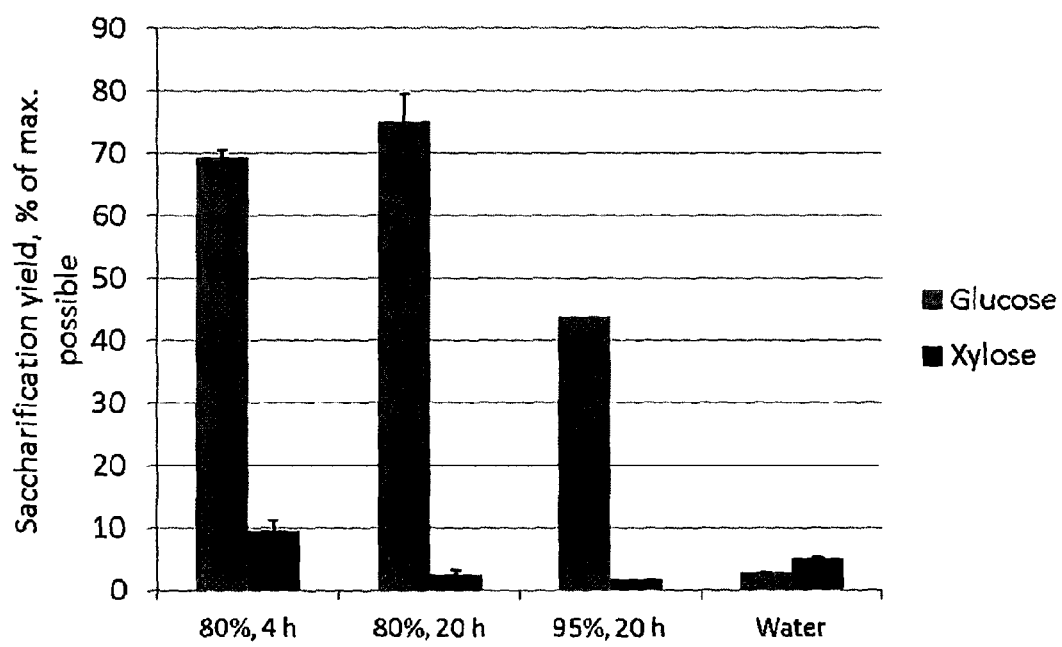

FIG. 35 shows the enzymatic saccharification yields obtained from *Miscanthus* after pretreatment with [C$_4$Him][HSO$_4$]$_{95\%}$ and [C$_4$Him][HSO$_4$]$_{80}$%. The saccharification was carried out for 96 h. The yields are based on the glucan and hemicellulose content of the untreated biomass.

Figure 36:
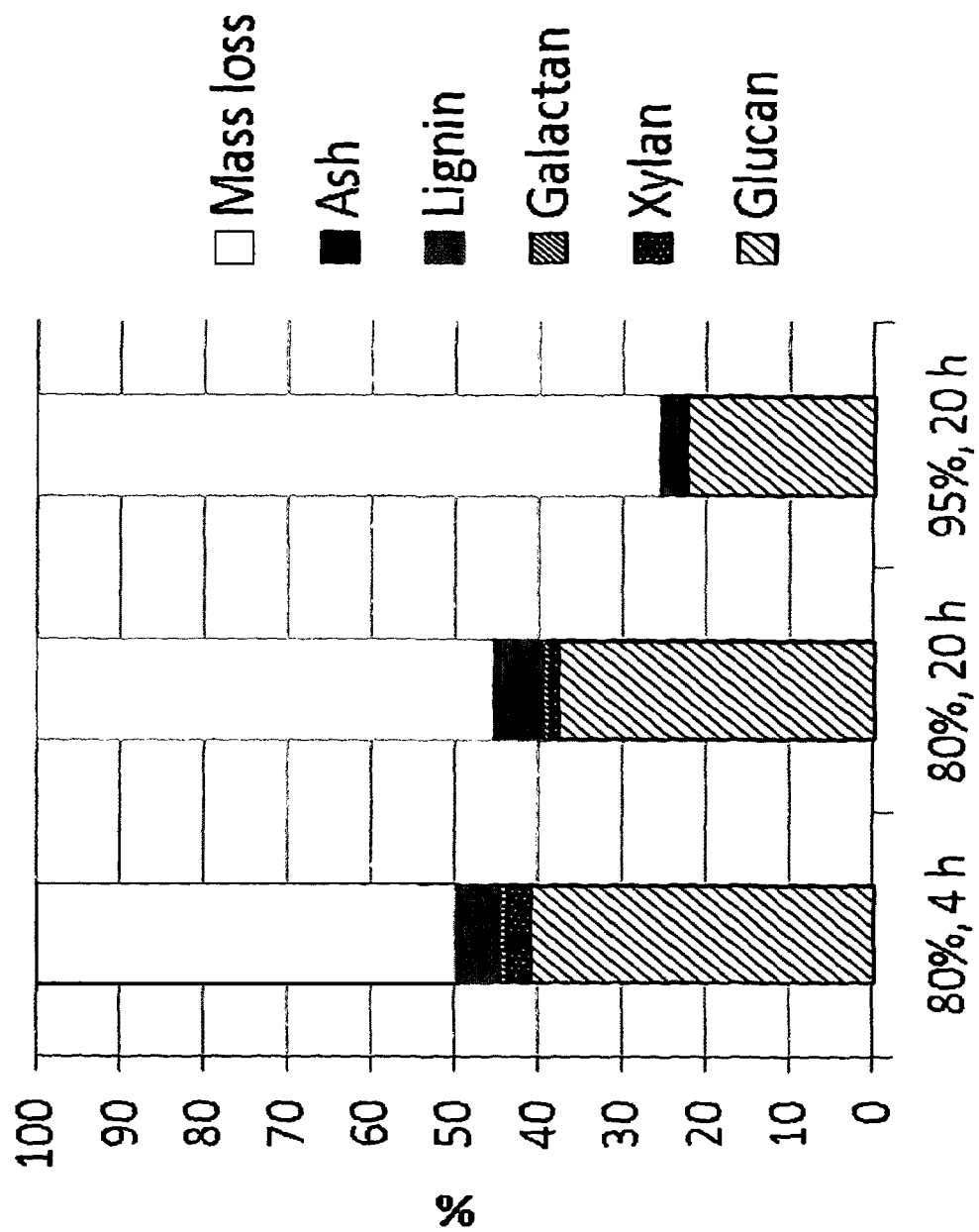

FIG. 36 shows the composition of *Miscanthus* after pretreatment with [C$_4$Him][HSO$_4$] water mixtures at 120° C.

Figure 37:
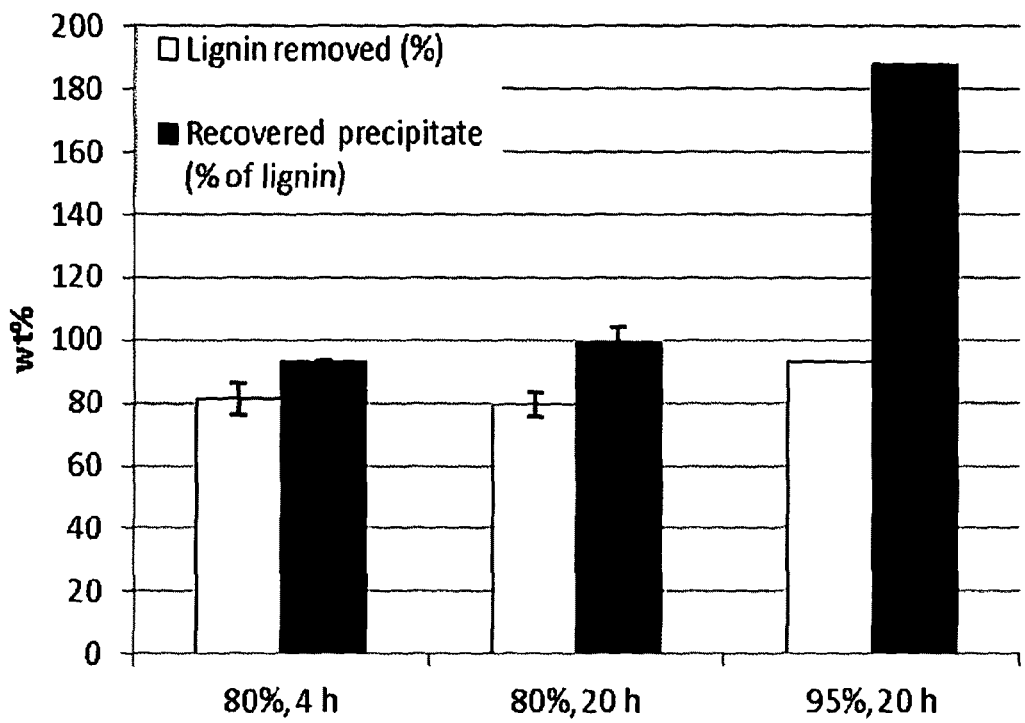

FIG. 37 shows the lignin removal and precipitate yield after pretreatment of *Miscanthus* with [C$_4$Him][HSO$_4$] water mixtures at 120° C. The yields are based on the lignin content of the untreated biomass.

Figure 38:
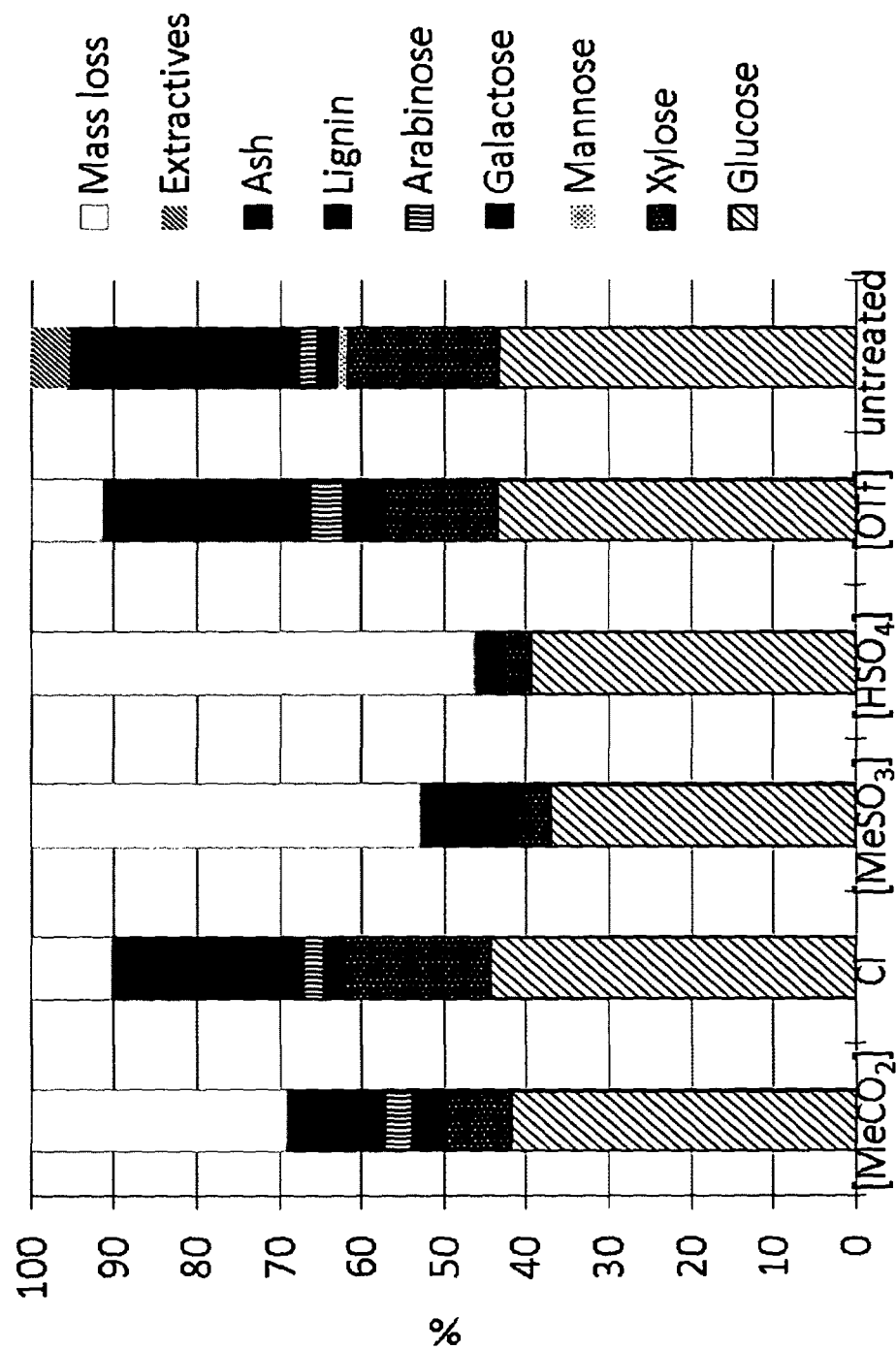

FIG. 38 shows the effect of the ionic liquid anion on the mass loss and the composition of the recovered pulp after pretreatment of *Miscanthus* with 80% ionic liquid water mixtures at 120° C. for 22 h. The data are ordered (left to right) according to the hydrogen-bond basicity of the ionic liquid, which is, in case of 1,3-dialkylimidazolium ionic liquids, a property of the anion.

Figure 39:
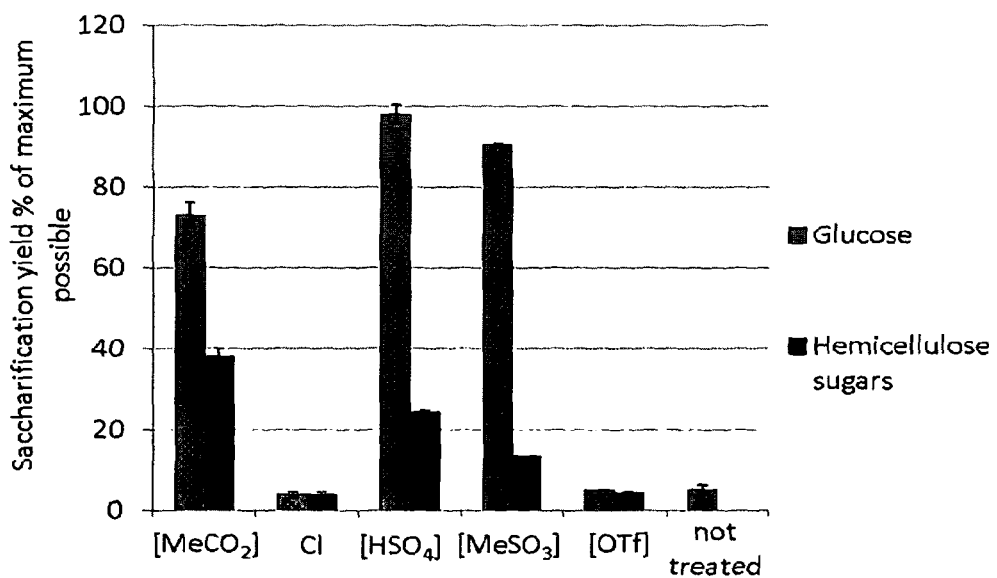

FIG. 39 shows the impact of the ionic liquid anion on glucose and hemicellulose yields after enzymatic saccharification of *Miscanthus* pulp pretreated with 80/20 vol % ionic liquid water mixtures at 120° C. for 22 h. The yields are based on the glucan and hemicellulose content of the untreated biomass.

Figure 40:
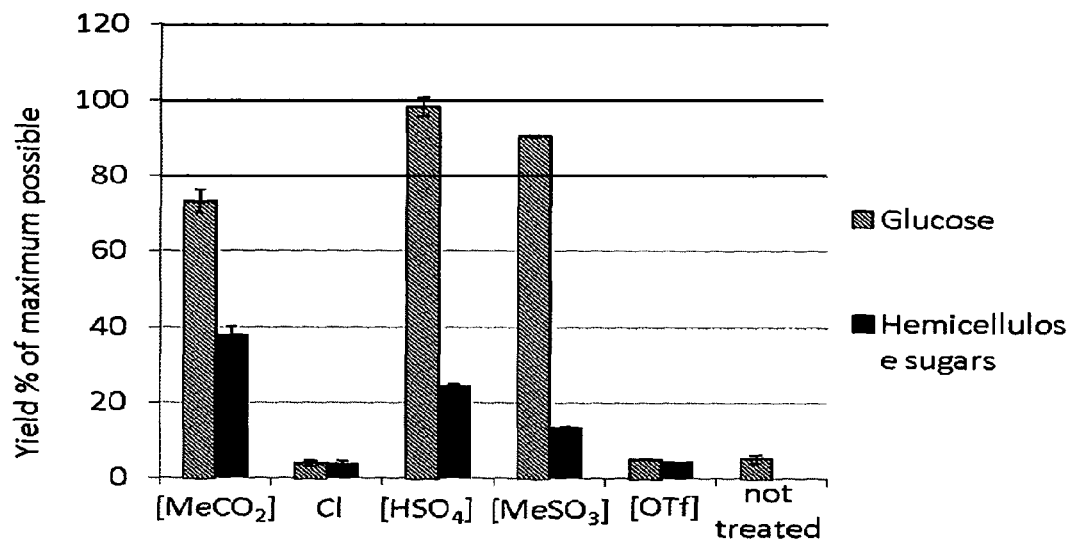

FIG. 40 shows the effect of the anion on the lignin removal and precipitate yield after pretreatment of *Miscanthus* with 80/20 vol % ionic liquid water mixtures. The higher yield from [HSO$_4$]$^-$ containing liquors (compared to FIG. 30 and FIG. 34) is ascribed to the larger quantity of ionic liquid and biomass used in this experiment. Values are relative to the lignin content of the untreated biomass.

Figure 41:
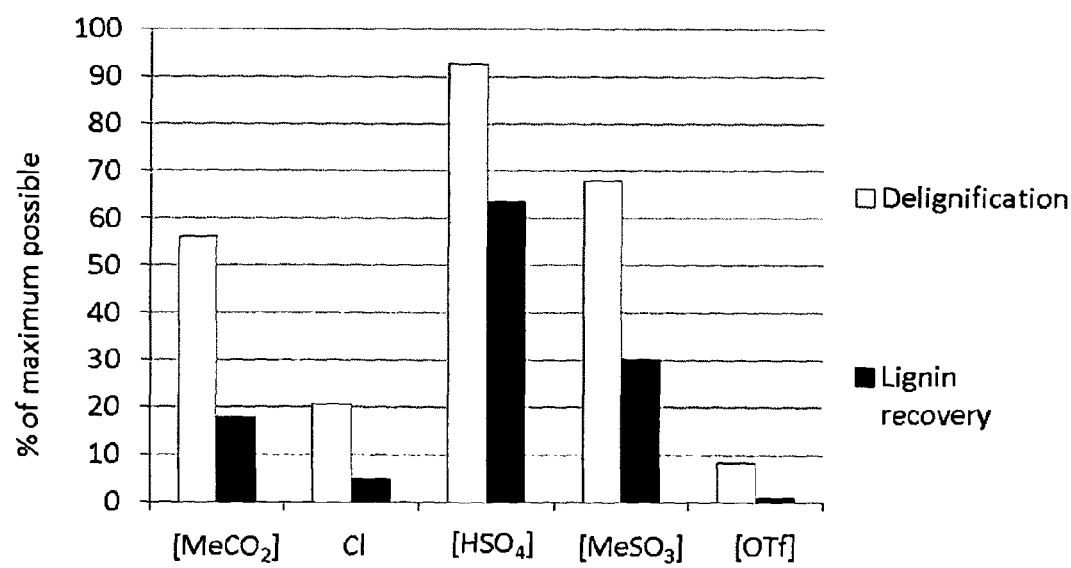

FIG. 41 shows sugar monomers and furfurals solubilised in liquors containing 80 vol % 1,3-dialkylimidazolium ionic liquids with various anions and 20 vol % water after treatment of *Miscanthus* at 120° C. for 22 h. The yields are based on the glucan and hemicellulose content of the untreated biomass.

Figure 42:
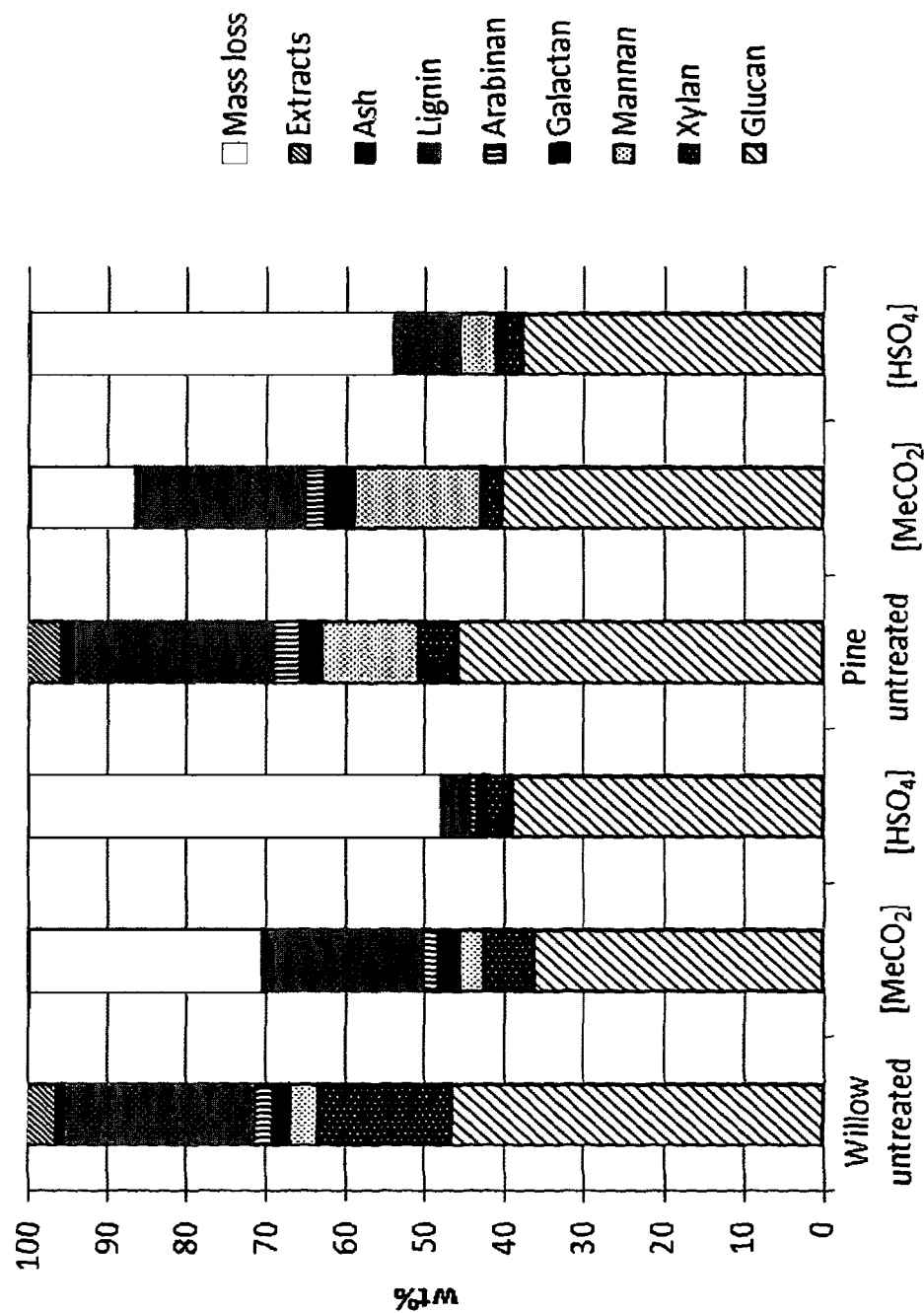

FIG. 42 shows the composition of willow (3 bar graphs on the left) and pine (on the right) before and after pretreatment with [C$_4$C$_1$im][HSO$_4$]$_{80\%}$ and [C$_4$C$_1$im][MeCO$_2$]$_{80\%}$ for 22 h at 120° C.

Figure 43:
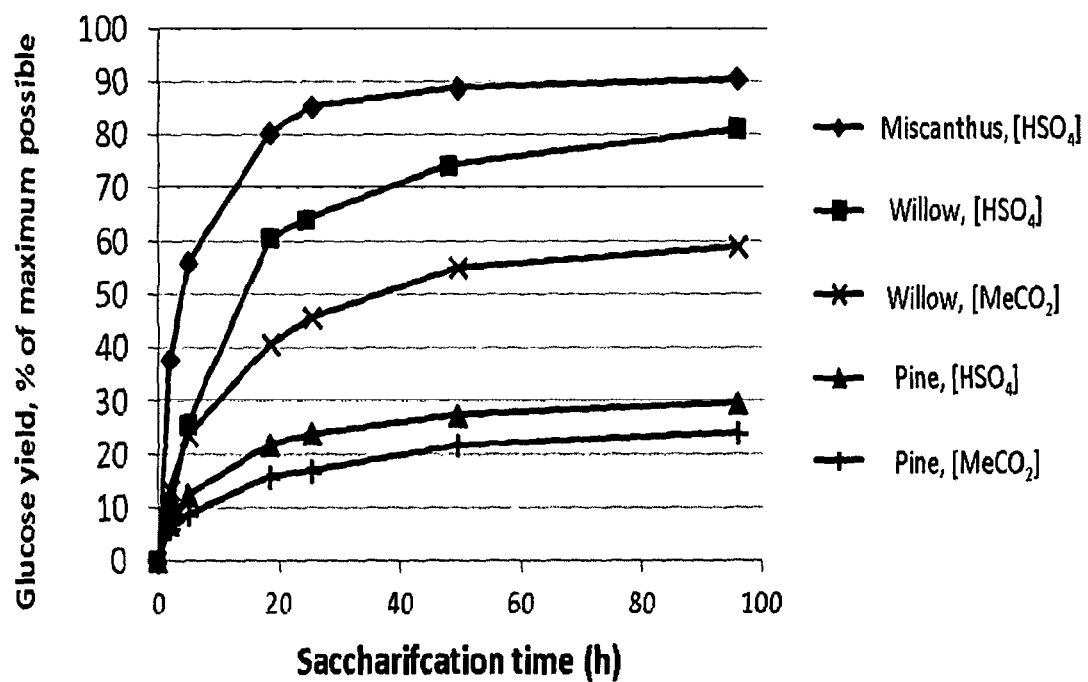

FIG. 43 shows the enzymatic saccharification of lignocellulosic feedstocks after pretreatment with [C$_4$C$_1$im][HSO$_4$]$_{80\%}$ or [C$_2$C$_1$im][MeCO$_2$]$_{80\%}$ for 22 h at 120° C. The yields are based on the glucan and hemicellulose content of the untreated biomass.

Figure 44:
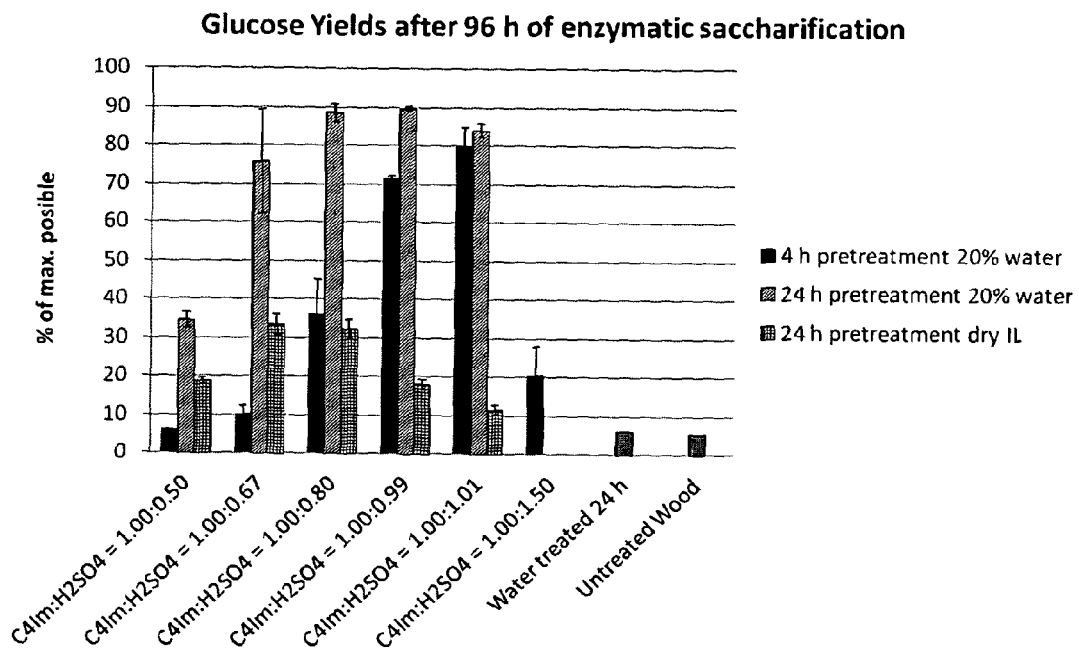

FIG. 44 shows the glucose yields after 96 hours of enzymatic saccharification following treatment with [C$_4$Him][HSO$_4$] wherein the relative concentrations of acid and base have been varied.

Figure 45:
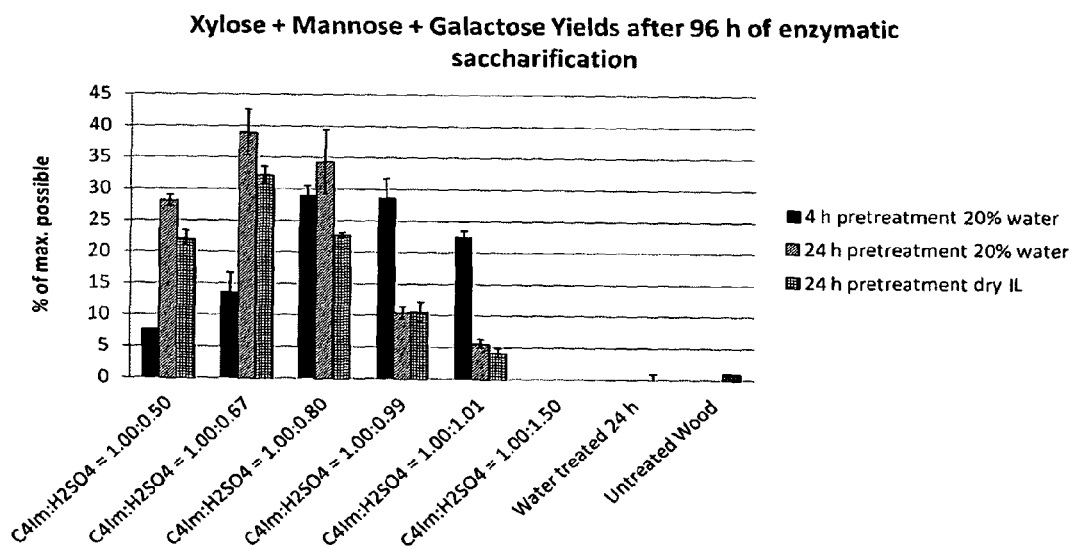

FIG. 45 shows the xylose, mannose, and galactose yields after 96 hours of enzymatic saccharification following treatment with [C$_4$Him][HSO$_4$] wherein the relative concentrations of acid and base have been varied.

Figure 46:
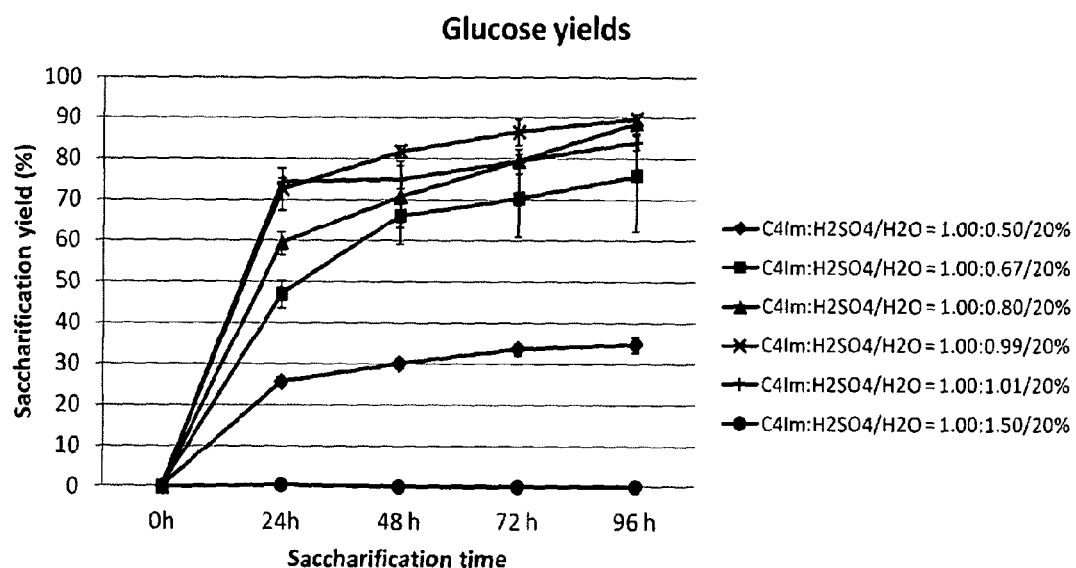

FIG. 46 shows the changes in the glucose yields over time during enzymatic saccharification following treatment with [C$_4$Him][HSO$_4$] wherein the relative concentrations of acid and base have been varied.

Figure 47:
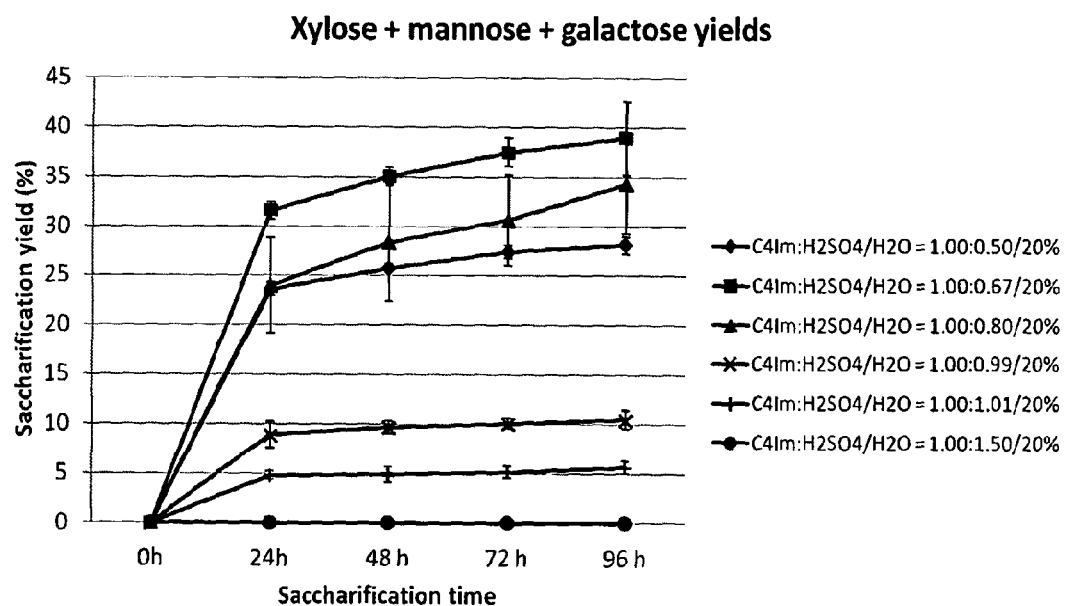

FIG. 47 shows the changes in the xylose yields over time during enzymatic saccharification following treatment with [C$_4$Him][HSO$_4$] wherein the relative concentrations of acid and base have been varied.

Figure 48:
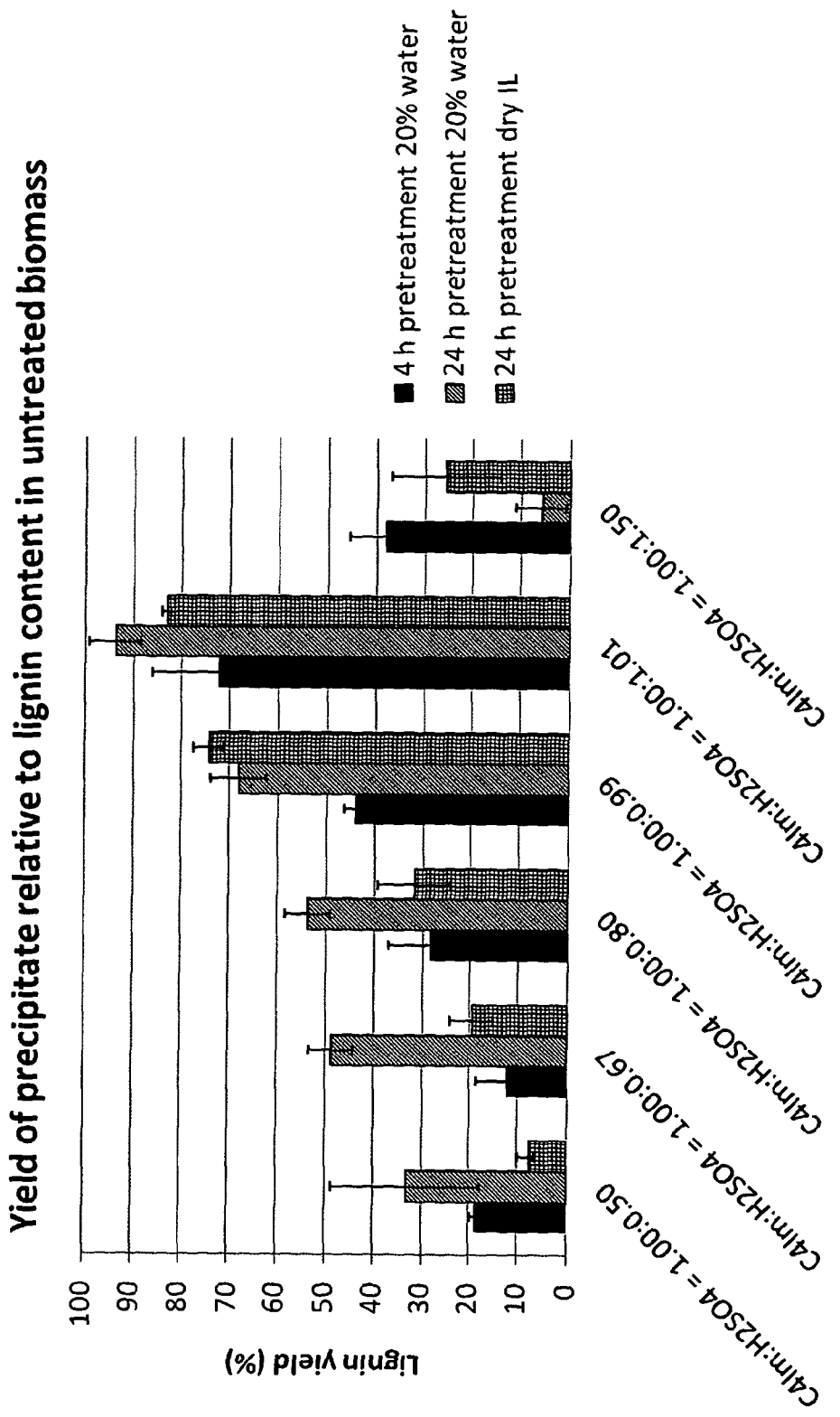

FIG. 48 shows the yield of precipitate relative to lignin content in untreated biomass following treatment with [C$_4$Him][HSO$_4$] wherein the relative concentrations of acid and base have been varied.

Figure 49:
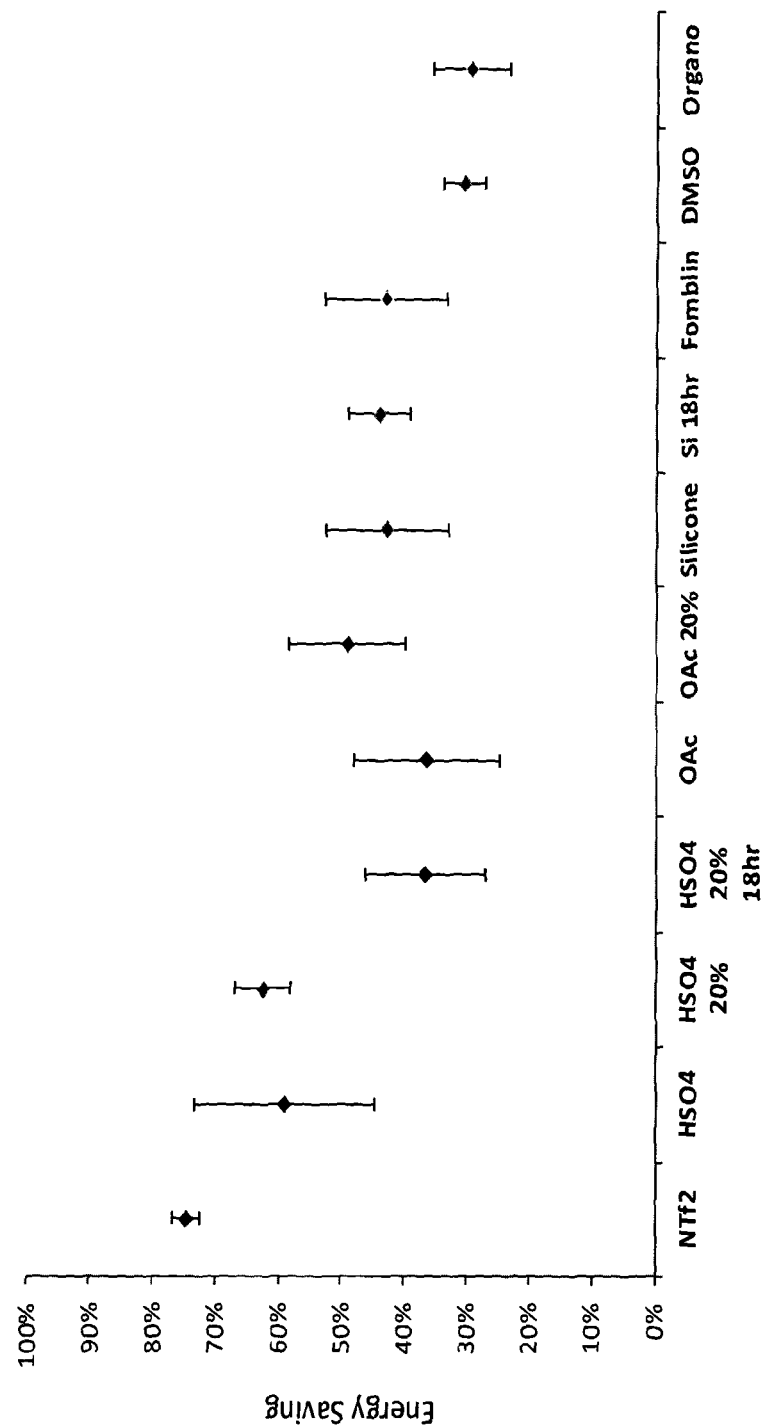

FIG. 49 shows the woodchip grinding energy saving for various pre-treatment methods relative to dry wood.

Figure 50:
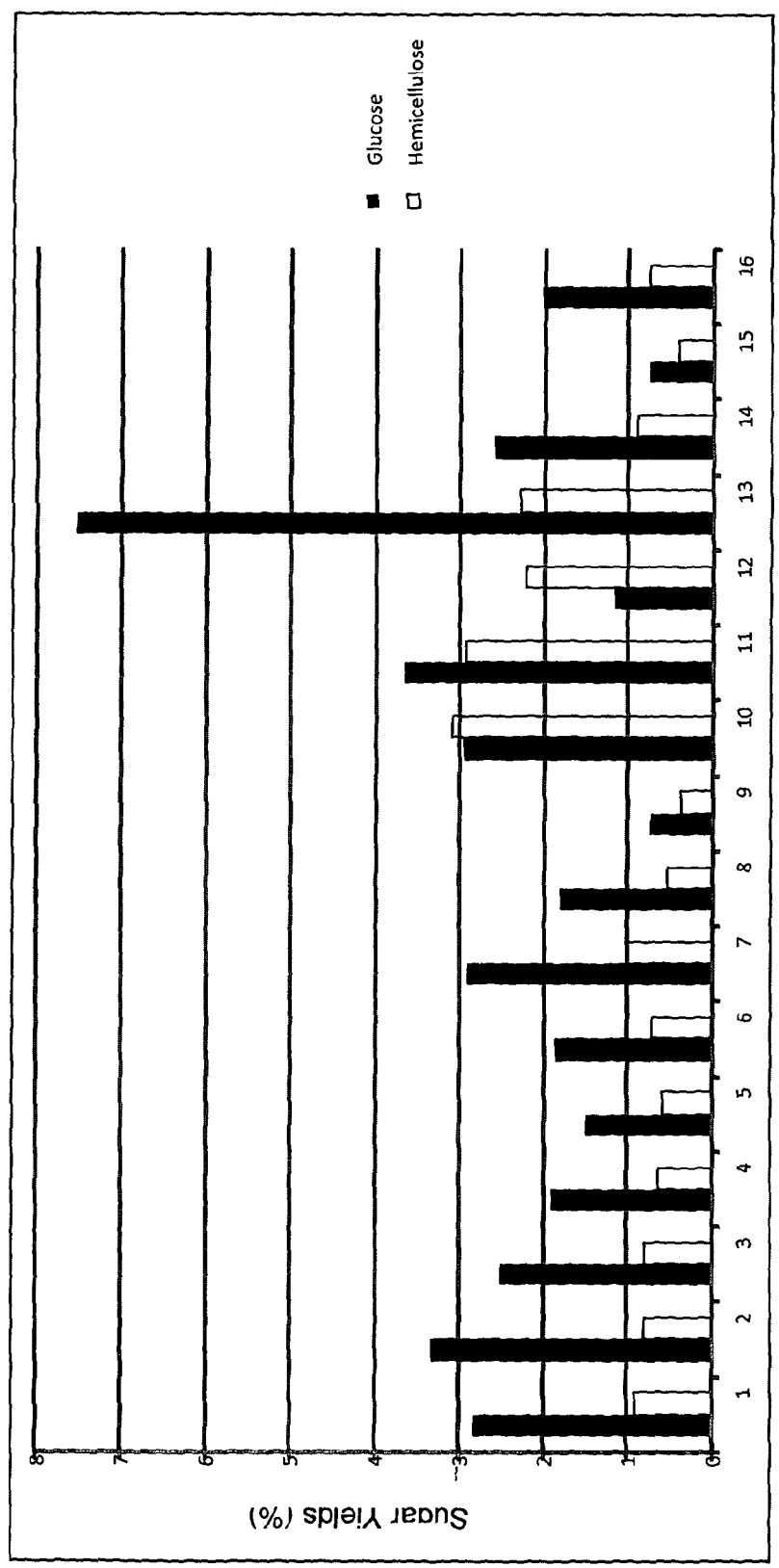

FIG. 50 shows the sugar yields from enzymatically treated wood powder ground from woodchips pre-treated in different ways, as a percentage of the sample dried-weight.

DETAILED DESCRIPTION OF THE INVENTION

The invention will now be described in the following non-limiting examples with reference to the figures.

Example 1

Biomass

The lignocellulosic biomass was pine sapwood (*Pinus sylvestris*, variety SCOES) from East Sussex, willow (*Salix* sp. variety TORA) de-barked mixed stems and *Miscanthus× giganteus*. All biomass was stored air-dried at room temperature, ground and sieved (0.18-0.85 mm mesh) before use. Dry *Miscanthus giganteus* internodes (0=11 mm) were cut into discs of 5 mm height in order to obtain *Miscanthus* wood chips. The moisture content of untreated lignocellulose was 8.0% (*Miscanthus*), 8.9% (Pine) and 7.6% (Willow) based on oven-dry weight. The biomass was stored in plastic bags at room temperature.

Synthesis of 1-butyl-3-methylimidazolium hydrogen sulfate [C$_4$C$_1$im][HSO$_4$]

170.67 g (682 mmol) [C$_4$C$_1$im][MeSO$_4$](BASF quality) was mixed with 25 ml distilled water in a round-bottomed flask with Graham condenser followed by a horizontal Liebig condenser. The mixture was heated to reflux. The Graham condenser was cooled to 65° C. using a temperature-controlled circulator. The Liebig condenser was cooled with room temperature water and condensed methanol.

The water was refluxed for 24 h. Most water was removed with the rotary evaporator and the ionic liquid dried in vacuo at 45° C. The yield was 98.1 wt %.

Synthesis of 1-butyl-3-methylimidazolium methane-sulfonate [C$_4$C$_1$im][MeSO$_3$]

50.0 ml (0.380 mol) 1-ethylimidazole and 42 ml (0.495 mol) dimethyl carbonate and 100 ml methanol were charged into a 300 ml stainless steel pressure reactor with Teflon lining and stir bar. The mixture was heated at 140° C. for 24 h, after which a yellowish solution containing the product ionic liquid was obtained (conversion: 98%). 33.73 g (351 mmol) pure methanesulfonic acid was added to a stirred crude product mixture containing 351 mmol 1-butyl-3-methylimidazolium methyl carbonate. Vigorous gas formation was observed. The ionic liquid was dried in vacuo until crystallisation was observed. The product was recrystallised twice in acetonitrile, washed with ethyl acetate and dried under reduced pressure. The product was a white solid. Yield: 70%

Liquid Uptake into *Miscanthus* Chips

*Miscanthus* wood chips were covered with ionic liquid while under vacuum to encourage even soaking. The ionic liquids were prepared as described above, but are also available commercially e.g. from Sigma-Aldrich, BASF. The ionic liquids were dried to a water content <0.3 wt %, with exception of [C$_4$Him][HSO$_4$] which had a water content of 1 wt %.

The samples were incubated in snap-top glass vials with plastic cap for 20 days and then heated to 80° C. for a few hours. The uptake was calculated according to Eq. 1, with m$_{80° C.}$ being the mass after the incubation, m$_{ps}$ the mass after pre-soaking at room temperature and ρ the ionic liquid density at 25° C.

$$V_{uptake} = \frac{m_{80° C.} - m_{ps}}{m_{ps} - \rho} \quad \text{Eq. 1}$$

Determination of Moisture Content

To determine the moisture content, 100-200 mg air-dried biomass were wrapped in aluminium foil of known weight and dried in an oven at 105° C. overnight. The samples were transferred into a desiccator with activated silica and the weight determined after 5 min. The moisture content was calculated according to Equation 2. The moisture content of the air-dried biomass (both untreated and treated) was in the range 5-12%.

$$\text{moisture (\%)} = \frac{m_{air\ dried} - m_{oven\ dried}}{m_{oven\ dried}} \cdot 100\% \quad \text{Eq. 2}$$

Softening of *Miscanthus* Chips in [C$_4$C$_1$im][MeSO$_4$]

Figure 1:
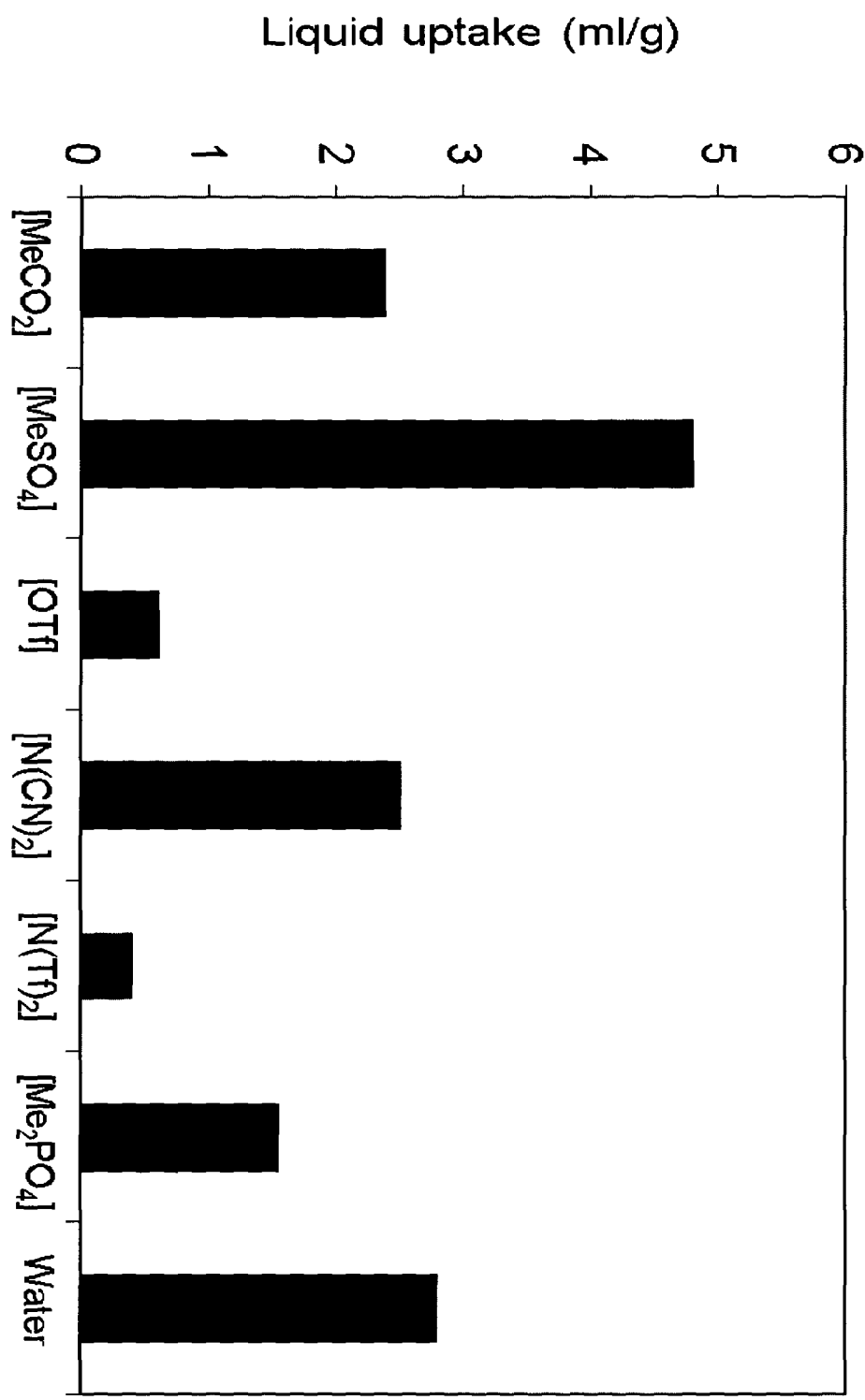
FIG. 1 shows the uptake of ionic liquids into *Miscanthus* chips at 80° C.

During trial measurements that were designed to find ionic liquids that had swelling effects on biomass, an unusual effect of the ionic liquid [C$_4$C$_1$im][MeSO$_4$] on *Miscanthus* chips was observed, when the samples were heated to 80° C. Instead of swelling, the chips shrunk, moreover they absorbed significantly more liquid than chips immersed in other ionic liquids or water (FIG. 1).

Figure 2:
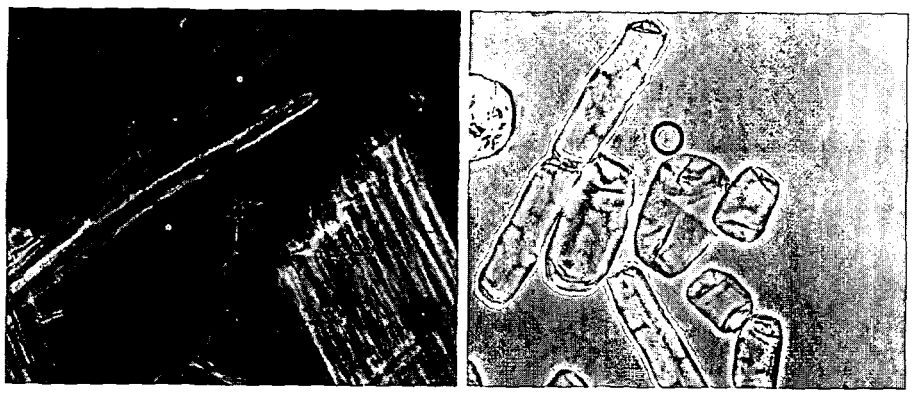
FIG. 2 shows images of *Miscanthus* wood dissolved in wet $[C_4C_1im][MeSO_4]$ using light transmission microscopy. Left: Outer part with fibre cells; right: parenchyma cells. Magnification was 10×.

The chips immersed in this ionic liquid became soft and even visibly dissolved in the ionic liquid upon stirring. The apparent solution was examined under the microscope and revealed the presence of separated parenchyma and fibre cells (FIG. 2).

It appeared that the middle lamella, the glue between the cell walls was affected by the ionic liquid. The middle lamella in grasses consists of hemicelluloses, including pectins, and in mature tissues a large proportion of lignin (>50% in fully lignified wood). Therefore it is possible that either of the major components or both were solubilised by the ionic liquid.

These results suggest that the surface area of *Miscanthus* chips can be vastly enhanced using a mild treatment, and also that this ionic liquid could be able to enhance the digestibility of the lignocellulose by solubilising lignin and hemicelluloses.

Pretreatment of Lignocellulosic Biomass and Isolation of Pulp

In order to ensure a homogenous samples, the *Miscanthus* stems were ground and particles of 0.18-0.85 mm width used. The biomass had been harvested in winter and air-dried. The pretreatment was performed in wide-mouthed culture flasks with screw cap and Teflon lining. The flasks were chosen, because they were guaranteed to withstand temperatures up to 120° C. and the Teflon lining ensured chemical resistance as well as tight capping. Stirring was not used, because the oven did not support stirring. In order to minimise ionic liquid use, small batches of 0.5 g oven-dried biomass were used, unless stated otherwise. Into this, 5 ml of pretreatment solvent was added. This was just enough to cover the ground *Miscanthus* biomass without compressing it.

After the pretreatment was finished, the samples were cooled to room temperature and mixed with 10 ml methanol. The suspension was filtered through filter papers (Whatman 541 or equivalent, hardened) after a couple of hours. The supernatant was set aside for determination of lignin yield and analysis of furfural content. The solids were washed with methanol from a wash bottle and incubated with 10 ml fresh methanol overnight. The suspension was filtered again, rinsed with methanol from a wash bottle and the solids dried on the filter paper on a laboratory bench overnight. The air-dried weight was recorded and the samples transferred into re-sealable air-tight sample bags. The moisture content was determined as described above. In order to obtain enough material for compositional analysis the pretreatment experiments were scaled up 2-3×.

Lignin Isolation

The supernatant obtained after pretreatment was dried under mild vacuum at 40° C. to remove the organic wash solvent using a carousel 12 with glass tubes (Radleys), equipped with a hotplate and rare earth metal stir bars. 10 ml water was added to precipitate the lignin as a fine suspension. The precipitate was washed 3 times with distilled water, air-dried and subsequently dried under high vacuum at room temperature. The yield was determined by weighing. The precipitates were stored in glass vials with plastic cap.

The precipitate yield was calculated based on the Klason lignin content of untreated biomass using the equation below. Part of the precipitate may be pseudo-lignin.

$$\text{Lignin yield (\%)} = \frac{m_{precipitate}}{m_{Klason\ Lignin}} \cdot 100\%$$

The precipitate was characterised by IR spectroscopy using a Spectrum 100 IR machine (Perkin-Elmer) equipped with an universal ATR sampling accessory with diamond crystal.

Figure 3:
FIG. 3 shows ground *Miscanthus* after pretreatment with $[C_4C_1im][MeSO_4]$. Left: pretreated at 120° C. for 6 h with pure ionic liquid. Right: pretreated at 120° C. for 22 h with 80/20% v/v ionic liquid/water after washing.

It was a surprise to find that treating *Miscanthus* flour with pure [C$_4$C$_1$im][MeSO$_4$] at 120° C. resulted in a solid ionic liquid wood paste (FIG. 3 left). The saccharification yield from this paste was low. The addition of water, however, allowed the separation of ionic liquid and a *Miscanthus* pulp (FIG. 3 right) even after extended periods of heating (24 h). The liquid turned almost black during the pretreatment, but after separating liquid and solid fraction, a beige pulp was obtained. In preliminary experiments, a very high digestibility was observed.

Example 2

Saccharification

Enzymatic saccharification was performed according to LAP "Enzymatic saccharification of lignocellulosic biomass" (NREL/TP-510-42629), issue date Mar. 21, 2008. 150 mg of untreated and pretreated air-dried sample was used per saccharification. When a pretreatment condition was run in duplicate or triplicate, saccharification was only performed once per sample. If the pretreatment condition was not replicated, the saccharification was performed in duplicate. The enzymes were *T. reseei* cellulase and Novozyme 188 cellobiase that also contains hemicellulolytic activity and can therefore hydrolyse xylan (both from Sigma-Aldrich). Glucose and hemicellulose yields were calculated based on the glucose and hemicellulose content of the untreated biomass, respectively.

Compositional Analysis

The compositional analysis (lignin, carbohydrates, ash) was performed according to Laboratory analytical procedure (LAP) "Determination of structural carbohydrates and lignin in biomass" (NREL/TP-510-42618), issue date Apr. 25, 2008. No replicates were run.

The extracts from untreated pine and willow biomass were removed by a one-step automated solvent extraction with 95% ethanol using an ASE 300 accelerated solvent extractor (Dionex) according to the LAP "Determination of extractives" (NREL/TP-510-42619), issue date Jul. 17, 2005. Extracts from untreated *Miscanthus* were removed by a two-step solvent extraction using deionised water and subsequently 95% ethanol according to the same LAP.

HPLC analysis of glucose and hemicellulose sugars was performed on an Agilent 1200 system equipped with an Aminex HPX-87P column (Biorad), a de-ashing column and a Carbo-P guard column. The mobile phase was de-ionised water. The column temperature was set to 80° C. and the flow rate was 0.6 ml/min. The content of carbohydrates, Klason lignin, ash and extracts (where applicable) was expressed as a fraction of the sum (normalised to 100%).

Quantification of Solubilised Sugars and Furfurals

200 µl pretreatment liquor was mixed with 600 µl deionised water in a 1-5 ml plastic cup, vortexed and centrifuged with a table-top centrifuge (Biofuge 13, Heraeus) at maximum speed for 10 min. The supernatant was transferred into a clean cup and centrifuged for 10 min. The supernatant was transferred into HPLC sample vials and analysed on a Jasco HPLC system equipped with an Aminex HPX-87H column (Biorad) using a 10 mM sulfuric acid mobile phase. The column oven temperature was 55° C., the flow rate 0.6 ml/min and the acquisition time 55 min. Standard concentrations of 2-furaldehyde (furfural) and 5-(hydroxymethyl)-2-furaldehyde (HMF) standards were prepared in deionised water to concentration of 0.01, 0.02, 0.1, 0.2 and 0.4 mg/ml. The standards for carbohydrates were 0.1, 1, 2 and 4 mg/ml. The factor $f_{HPLC}(S)$ was obtained from the respective calibration curve. The relative yield of solubilised sugar monomers and furfurals, wt % (S), was calculated using Eq. 3. The molecular mass transformation factor $F_T$ was 1.37 for furfural, 1.28 for HMF, 0.91 for glucose and 0.88 for hemicellulose sugars. The mass fraction factor $F_C$ was 0.243 for hemicellulose sugars and furfural and 0.436 for glucose and HMF.

$$\text{wt \%}(S) = \frac{A_{HPLC} \cdot F_D \cdot V_{PL} \cdot F_T(S)}{F_{HPLC}(S) \cdot m_{biomass} \cdot F_C} \cdot 100\% \qquad \text{Eq. 3}$$

$A_{HPLC}$: area of HPLC peak, $F_{HPLC}(S)$: HPLC calibration factor for substance S, $F_D$: dilution factor, $V_{PL}$: volume of pretreatment liquor in ml, $m_{biomass}$: biomass (oven-dried weight) in mg, $F_C$: fraction of glucan or hemicellulose sugars in untreated biomass as determined by compositional analysis, $F_T(S)$: transformation factor accounting for molecular mass differences between starting material and product.

Figure 4:
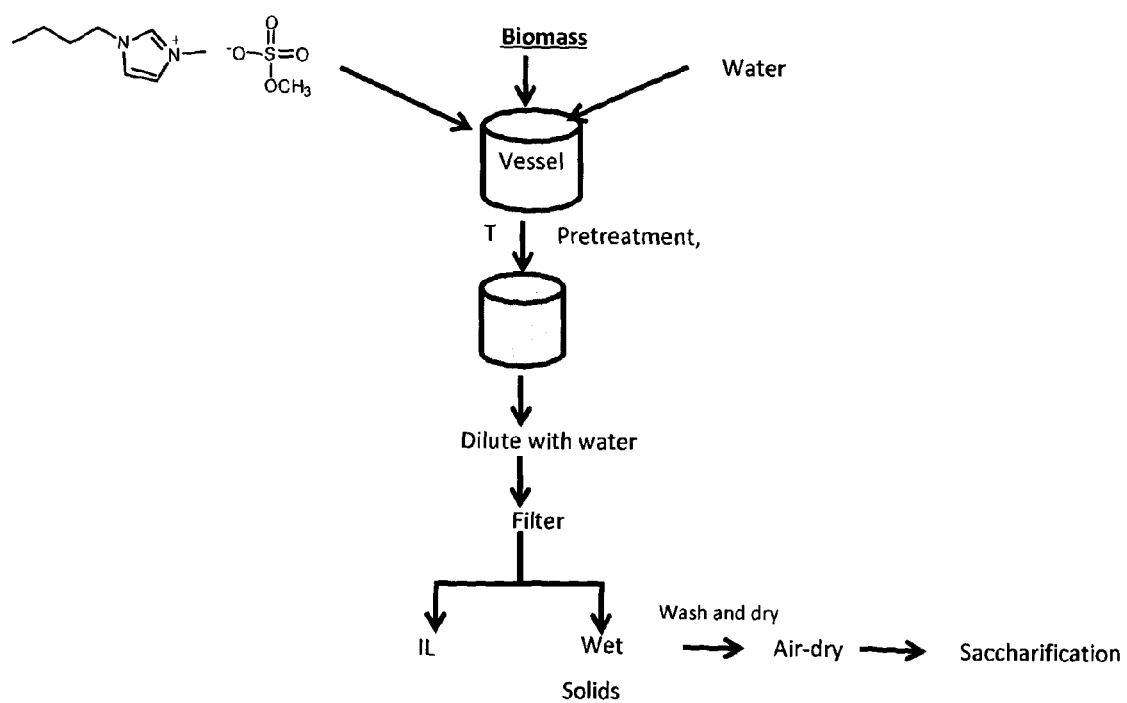
FIG. 4 shows the experimental setup for pretreatment of ground *Miscanthus* with $[C_4C_1im][MeSO_4]$/water mixtures.

Saccharification Yields after Pretreatment with 1-Butyl-3-Methylimidazolium Methyl Sulfate Water Mixtures The influence of water content on the digestibility was investigated. This confirmed that water was an important factor in the pretreatment with this ionic liquid. The water content was varied between 2% and 80 v/v %. The composition refers to the amount of pure components added, thus mixing effects on the volume are neglected. The pretreatment time was set to 22 h to allow the pretreatment to go to completion despite the lack of stirring. A set of control samples was treated with pure deionised water. The samples were processed according to FIG. 4. The pulp that could be isolated after the pretreatment was subjected to saccharification using cellulase and a hemicellulase mix (Novozyme 188) in a buffer.

Figure 5:
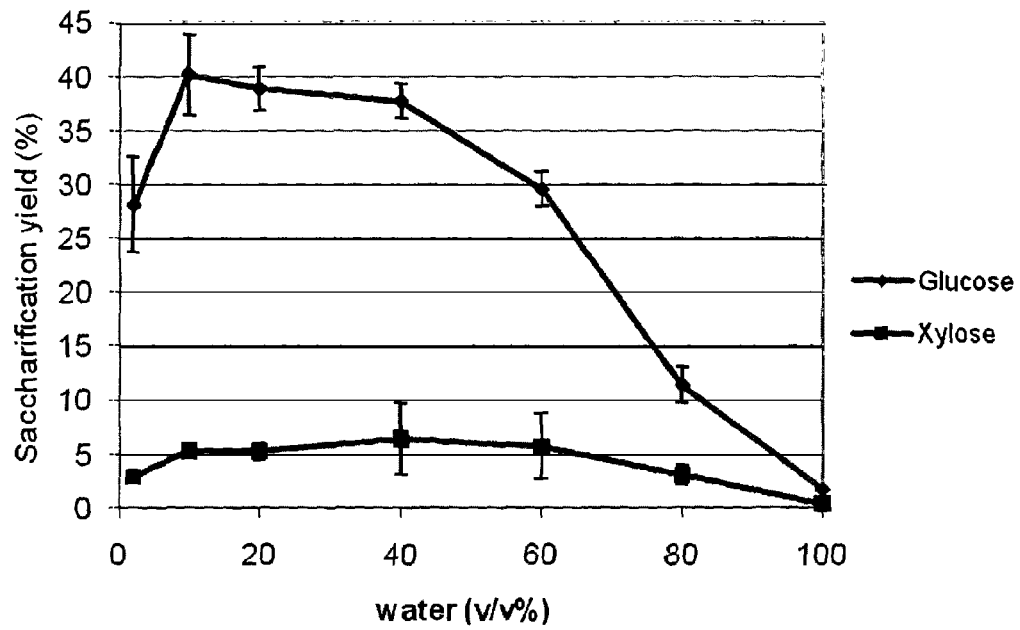
FIG. 5 shows saccharification yields after 22 h/120° C. pretreatment of ground *Miscanthus* with $[C_4C_1im][MeSO_4]$ water mixtures. The saccharification proceeded for 48 h. Yields are based on the oven-dried sample weight before the pretreatment.
Figure 6:
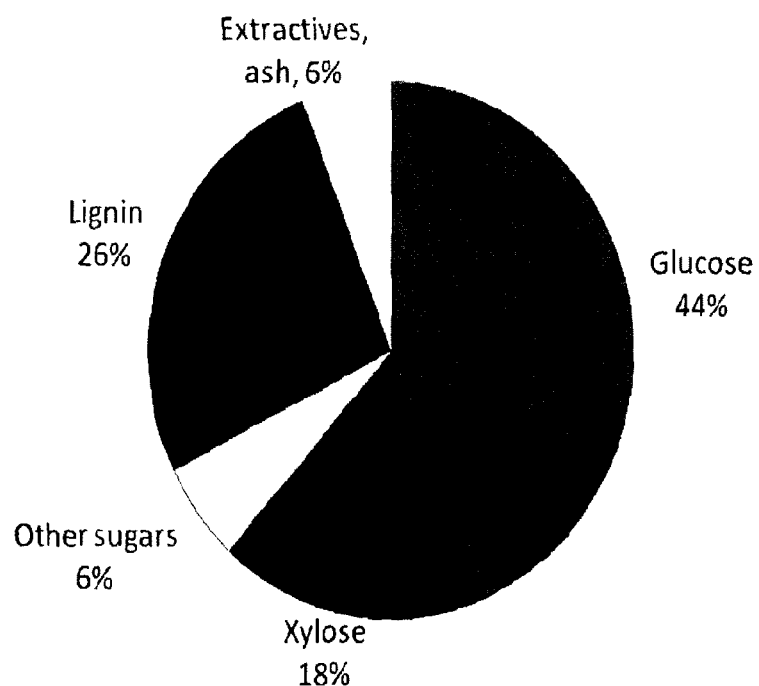
FIG. 6 shows the composition of untreated *Miscanthus* flour used in this study.

The yields after enzymatic digestion are shown in FIG. 5. The sugar yields vary widely. The highest glucose yield was observed for mixtures containing 10-40% water. Higher or lower water content reduced the glucose yield. The hemicellulose sugar xylose could also be quantified. The yield was much lower but followed a similar trend. Other hemicellulose sugars, such as arabinose, mannose and galactose, were below the detection level.

The saccharification yields can be compared with the composition of the original biomass. The amount of glucose in air-dried biomass was 43.6%. A glucose yield between 37.7 and 40.2 wt % after saccharification means that 86-92% of the original glucose were recovered in the solid fraction and could be hydrolysed by the cellulases within 48 h. These yields are very high and in stark contrast to the yields from the water-treated controls, for which the glucose yield was marginal.

The hemicellulose yields for the pretreated samples are generally low compared to the hemicellulose content of the untreated biomass. A yield of 5.3-6.4% means that only 29-35% of the hemicellulose was recovered during saccharification. It is still higher than the recovery from the controls. The almost quantitative glucose and good hemicellulose recovery is also reflected by the liquefaction of the pulp during the saccharification. While the untreated *Miscanthus* hardly changed its appearance during saccharification, the treated material was almost entirely solubilised. The left-over was a fine, voluminous brown powder. It was probably comprised of lignin which precipitated during the washing, as will be explained below.

The findings that water was required for the pretreatment are good news. Water is ubiquitous; it is not only present in biomass, but also the ionic liquid can contain lots of absorbed moisture. In terms of a process, this means that less energy needs to be spent on drying both biomass and ionic liquid. The results also suggest that a relatively wide range of water concentrations are acceptable, so a change in the water content will not necessarily mean a sharp drop in yield. The presence of water improves the process as the yield decreases if the water content is too low.

Example 3

Influence of Wash Solvent on Biomass Recovery and Fractionation

The previous examples indicate that the cellulose was significantly enriched in the pulp, which implies that some of the other components were removed. The low hemicellulose yield suggests that a significant fraction of the hemicellulose had been solubilised. However, the dark colour of the pretreatment liquor also suggests that part of the lignin was solubilised in the ionic liquid. Native lignin is not coloured, however, when lignin is chemically modified it often becomes darkly coloured, as can be seen with commercially available lignin preparations.

During the washing phase, the previously clear liquor became hazy upon dilution with distilled water and a fine precipitate began to settle. It was likely that this was lignin. Fractionation of lignin from the carbohydrate fraction has been part of the Organosolv pretreatment, from which Organosolv lignin can be obtained.

Example 4

Composition of Recycled [C$_4$C$_1$Im][MeSO$_4$]

The ionic liquid liquor obtained after lignin precipitation was dried under vacuum at 40° C. A sample of the dried ionic liquid was submitted to mass spectrometry. Part of the recovered ionic liquid was dissolved in DMSO-d$_6$ and a $^1$H NMR spectrum recorded. The peaks of the methyl group at 3.40 ppm and of the C-2 ring hydrogen were used to determine the anion to cation ratio. The pretreatment was carried out in capped vessels, so it is reasonable to assume that the water content did not change substantially during the pretreatment. The water introduced by the ionic liquid and the air-dried biomass was taken into account, but not water consumed in hydrolytic reactions.

The spectrum suggested that the recovered ionic liquid appeared to be free of degradation products. However, the peak integral for the methyl group on the anion was significantly diminished. A mass spectrum of the mixture revealed that hydrogen sulfate anions, [HSO$_4$]$^-$, were present alongside the methyl sulfate anions. The bond between the methyl group and the rest of the anion is an ester bond, a methoxy sulfate ester and thus, like all esters, susceptible to hydrolysis in the presence of water. Therefore, loss of the methyl group signal is attributed to a chemical equilibrium between methyl sulfate ester and the hydrolysed form (Scheme 1).

Scheme 1: Equilibrium between methylsulfate and hydrogensulfate at elevated temperatures in the presence of water

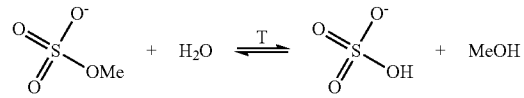

The pretreatment experiments were carried out in capped vessels, it is reasonable to assume a closed system.

Example 5

Pretreatment with 1-Butyl-3-Methylimidazolum Hydrogen Sulfate [C$_4$C$_1$im][HSO$_4$] Water Mixtures The pretreatment experiments were conducted with 1-butyl-3-methylimidazolum hydrogen sulfate water mixtures. If the methyl sulfate anion and the methanol were important, yields would be reduced. If the hydrogensulfate was important, yields should be as good as before. The main difference between the hydrogen sulfate anion and the anions is its acidity. The pK$_a$ of hydrogen sulfate is 1.99. This is more acidic than acetic acid (pK$_a$=4.72) but less than hydrochloric acid (pK$_a$=−7).

Figure 7:
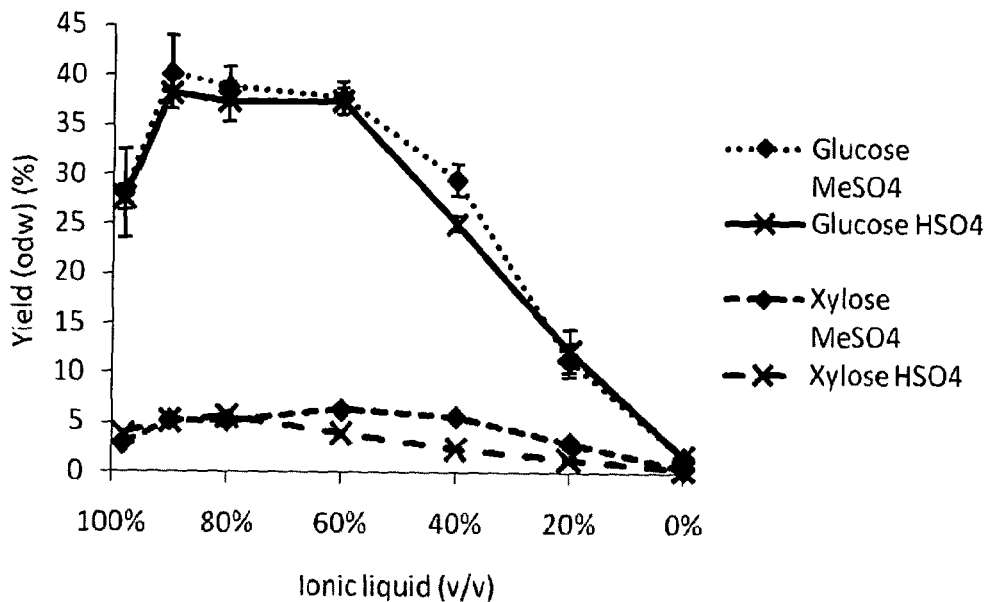
FIG. 7 shows saccharification yields from ground *Miscanthus* after pretreatment with $[C_4C_1im][HSO_4]$ and $[C_4C_1im][MeSO_4]$ water mixtures. The conditions were 120° C., 13 h and 22 h pretreatment time, respectively. Yields are based on the oven-dried sample weight before the pretreatment.

The saccharification yields for both glucose and xylose after pretreatment with [C$_4$C$_1$im][HSO$_4$] water mixtures were very similar to the yields found for [C$_4$C$_1$im][MeSO$_4$] water mixtures (FIG. 7). The glucose yield was high for ionic liquid containing 10-40% water. This was achieved in shorter time (13 h) than previously used (22 h).

This proves that hydrogensulfate anion paired with the 1-butyl-3-methylimidazolium cation is effective in pretreating *Miscanthus* lignocellulose.

Figure 8:
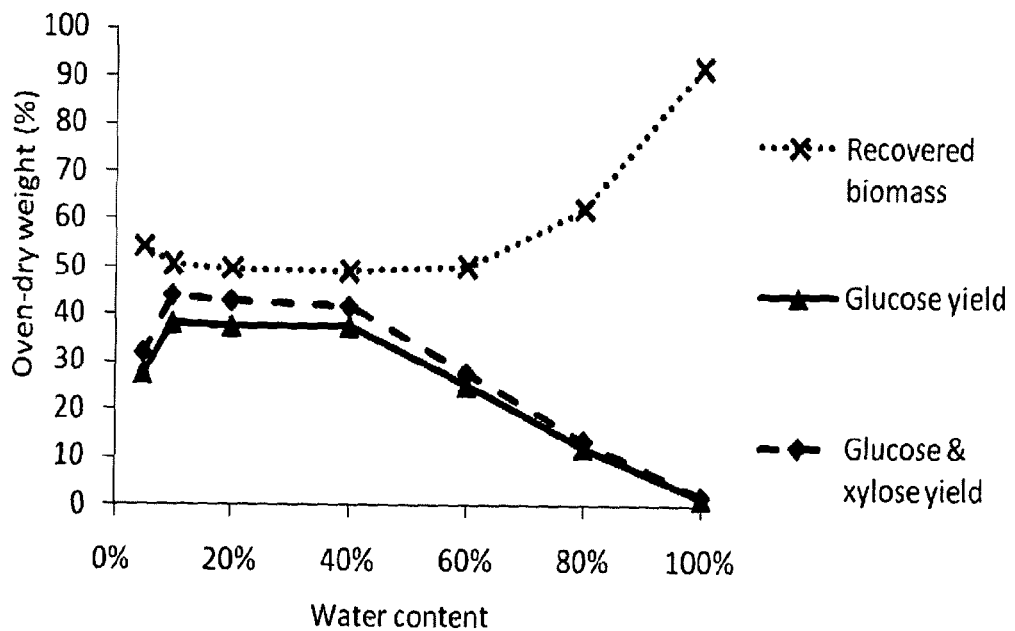
FIG. 8 shows percentage of recovered *Miscanthus* pulp after pretreatment with various $[C_4C_1im][HSO_4]$ water mixtures at 120° C. for 13 h as well as the glucose yield and total sugar recovery after saccharification.

The recovery of *Miscanthus* pulp is shown in FIG. 8. While pure water only removed 8% of the matter, removal by the ionic liquid was much more pronounced. Mass loss after pretreatment with 60-90% ionic liquid was around 50%. The glucose yield and total sugar yield after saccharification of the recovered solid are also depicted in FIG. 8. It can be seen that the saccharification yield is the higher the more lignin and hemicellulose have been solubilised. The figure also suggests that the cellulose which is the major source of glucose is enriched in the pulp.

Figure 9:
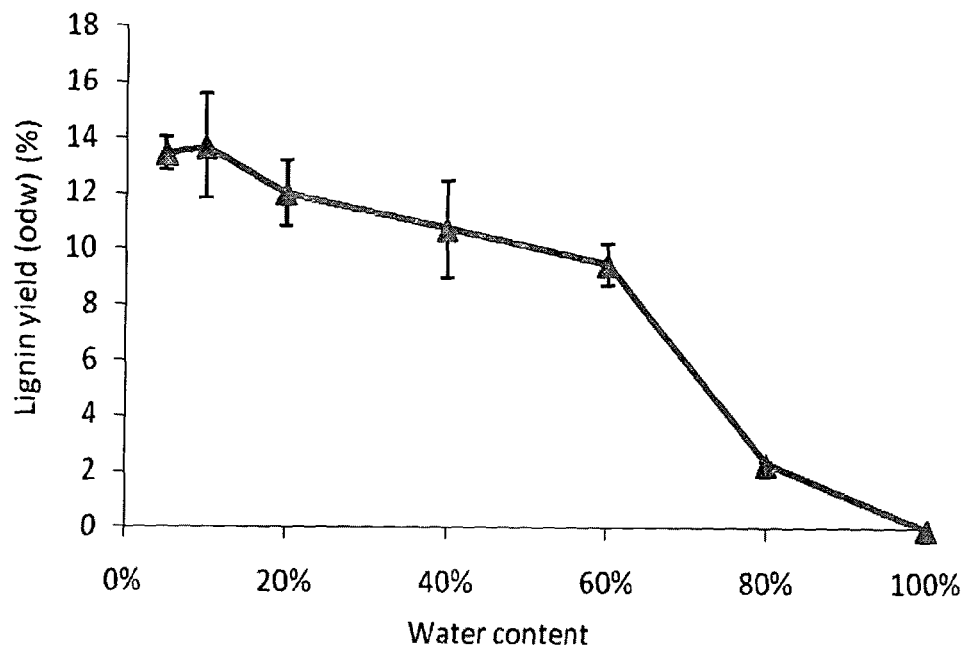
FIG. 9 shows lignin recovery after pretreatment with $[C_4C_1im][HSO_4]$ water mixtures at 120° C. for 13 h. Yields are based on the oven-dried sample weight before the pretreatment.

The precipitation of lignin from [C$_4$C$_1$im][HSO$_4$] was also investigated. FIG. 9 shows the lignin yield after washing the biomass with methanol and precipitating with water. The lignin yield correlates well with ionic liquid concentration. The higher the ionic liquid content the more lignin can be isolated. The yield only drops moderately from 13.4% and 13.7% at 5% and 10% water content, to 9.5% at 60% water content. A sharp drop in lignin yield was observed when the water content increased from 60% to 80%. This is in accordance with a reduced biomass solubilisation at 80% water content (FIG. 8).

Example 6

Time Course of Ionic Liquid Pretreatment

The pretreatment effect of ionic liquid water mixtures, either containing [C$_4$C$_1$im][HSO$_4$] or [C$_4$C$_1$im][MeSO$_4$], which contains a mixture of [MeSO$_4$]$^-$ and [HSO$_4$]$^-$ anions under the applied conditions, over time was investigated. The 80% ionic liquid pretreatment liquor was used as example pretreatment liquor.

Figure 10:
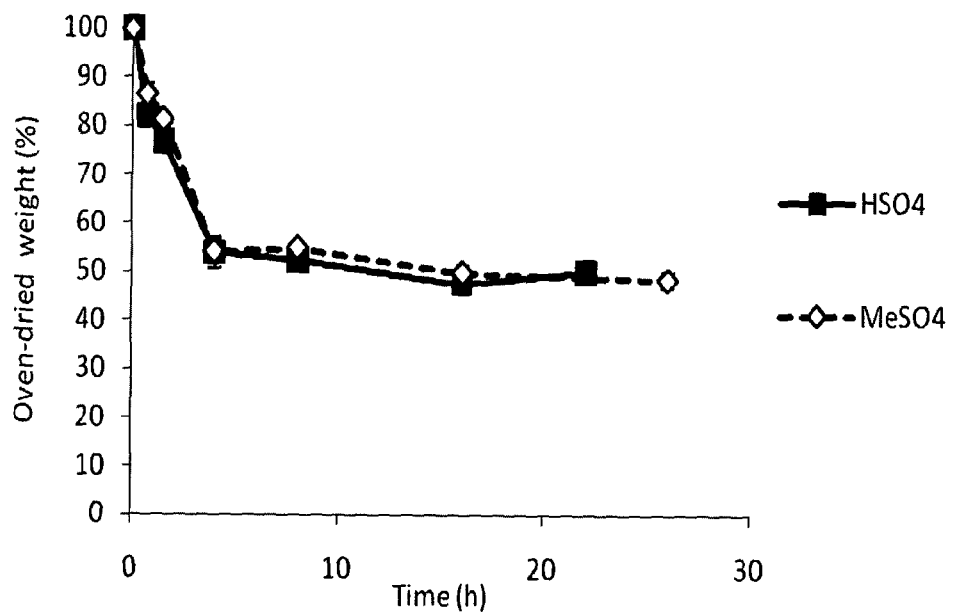
FIG. 10 shows mass loss time course for 80% v/v ionic liquid water mixtures pretreated at 120° C. The ionic liquids were $[C_4C_1im][MeSO_4]$ and $[C_4C_1im][HSO_4]$.

The time-resolved biomass recovery for both methyl sulfate and hydrogen sulfate is shown in FIG. 10. It can be seen that the majority of biomass solubilisation occurred within four hours after starting the pretreatment, accounting for 90% of the mass loss.

The remaining 10% were solubilised in the following 18-20 h. This was the case for both pretreatment liquors. Slight differences were observed before the 4 h time point, with hydrogen sulfate being better at removing the soluble biomass fraction within 45 and 90 mm.

Figure 11:
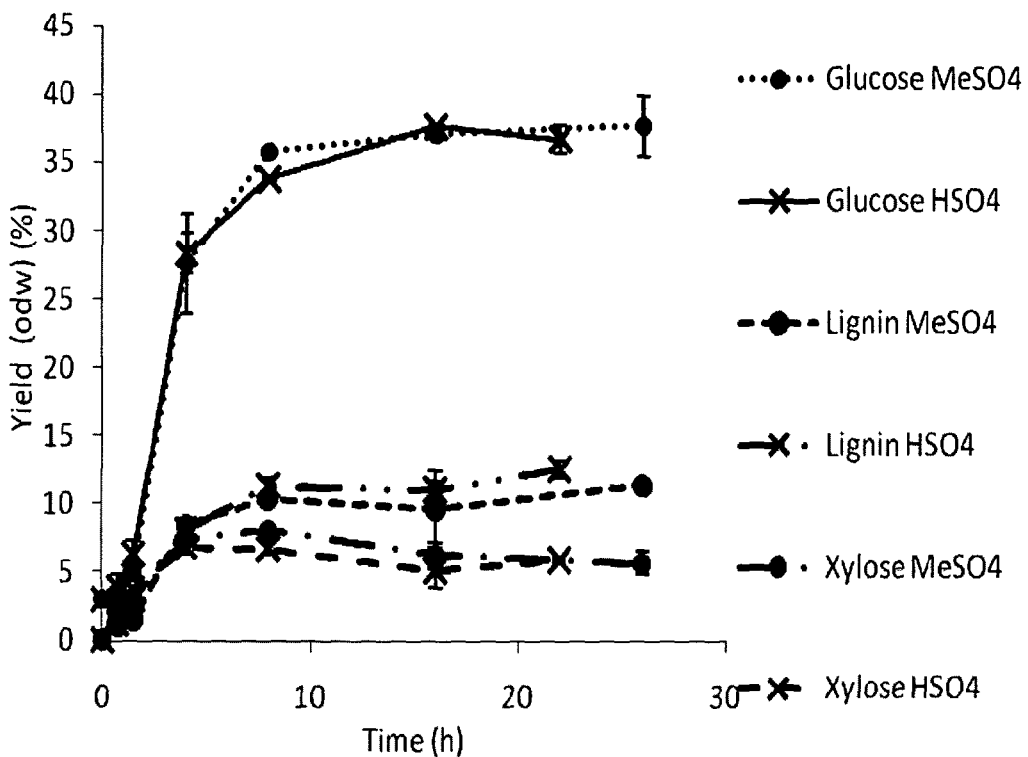
FIG. 11 shows time course study of saccharification and lignin yields from ground *Miscanthus*. Pretreatment with $[C_4C_1im][MeSO_4]_{80\%}$ and $[C_4C_1im][HSO_4]_{80\%}$ mixtures was performed at 120° C. for up to 26 or 22 h. Yields are based on the oven-dried sample weight before the pretreatment.

The corresponding saccharification and lignin yields are shown in FIG. 11. The glucose yield rose steeply in the first 8 h and then leveled in the remaining time. The hemicellulose yield on the other hand reached a maximum yield around 7% at 8 h and then declined to 5% towards the end of the pretreatment.

Although the majority of mass loss occurred within 4 h, the glucose yield was significantly improved by prolonging the pretreatment to 8 h.

The lignin yield followed a similar trend, increasing quickly within the first 8 h and changing only slightly afterwards.

In conclusion, the data suggest that the pretreatment does not need to be conducted for 22 h or even 13 h. 8-10 h appear to be enough to obtain the maximum possible yield of glucose. Prolonging the pretreatment does not seem to have a significant impact on the glucose yield, while the hemicellulose yield from the pulp decreases somewhat with longer pretreatment time.

The significant mass loss coupled with a high glucose yield suggests that a strong enrichment of the cellulose fraction occurs. In order to confirm this, analysis of the composition of *Miscanthus* before and during the pretreatment was carried out. Ground *Miscanthus* was pretreated for 2 h with both $[C_4C_1im][HSO_4]_{80\%}$ and $[C_4C_1im][MeSO_4]_{80\%}$. A 2 h incubation falls into the 'active' phase, when mass loss and saccharification yield increase rapidly. Therefore analysis of this samples offers a glimpse of the composition changes during this pretreatment phase.

Figure 12:
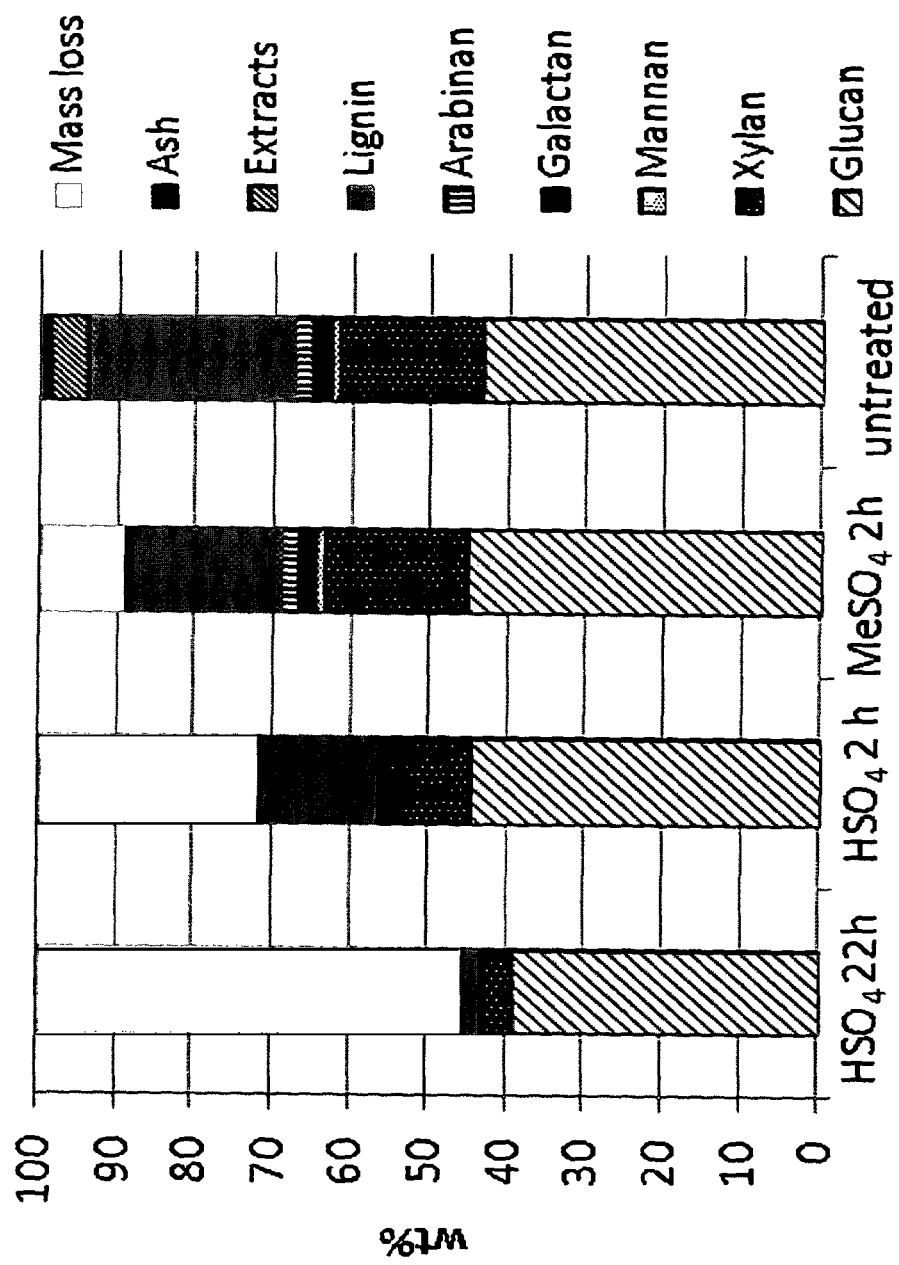
FIG. 12 shows the effect of pretreatment with $[C_4C_1im][MeSO_4]_{80\%}$ and $[C_4C_1im][HSO_4]_{80\%}$ at 120° C. on the composition of *Miscanthus* flour for various length of time.

FIG. 12 shows that for $[C_4C_1im][MeSO_4]_{80\%}$, the 2 h pretreatment resulted in 10% mass loss. The hemicellulose content was nearly unchanged, while the lignin content was reduced to 70%. The mass loss was significantly higher after pretreatment with $[C_4C_1im][HSO_4]_{80\%}$. As the figure shows, this was due to a reduction of lignin content (by 44%) as well as to the removal of hemicellulose sugars. The hemicellulose content was halved within 2 h. This can be explained with the acid-labile nature of hemicellulose. It is the fraction that is most susceptible to hydrolysis under acidic conditions. The solubilisation of the hemicellulose is the principal mode of action for dilute acid pretreatment and also occurs under the acidic conditions of the Organosolv process.

The composition after 22 h of pretreatment is also shown in FIG. 12. The solid fraction after the long pretreatment consisted of only 46% of the original biomass. The largest fraction was glucose, which made up 85.2% of the solid residue. This is almost twice as concentrated as in the original biomass, which had a glucose content of 43.6%. It appears that some glucose was lost during the pretreatment. It is possible that this is probably the glucose contained in the hemicellulose, but also exposed parts of the amorphous regions in cellulose fibrils might have been hydrolysed. Nevertheless, 39.5% of the original biomass was recovered as glucose, which is 91% of the glucose fraction. The hemicellulose content of the 22 h pulp was low, accounting for less than 9.4% of the solid fraction. This translates into a removal of 80% of the (non-glucose) hemicellulose sugars. A similar trend is observed for lignin. The lignin content after 22 h was only 4.1%. This means that 93% of the original lignin was solubilised.

Figure 13:
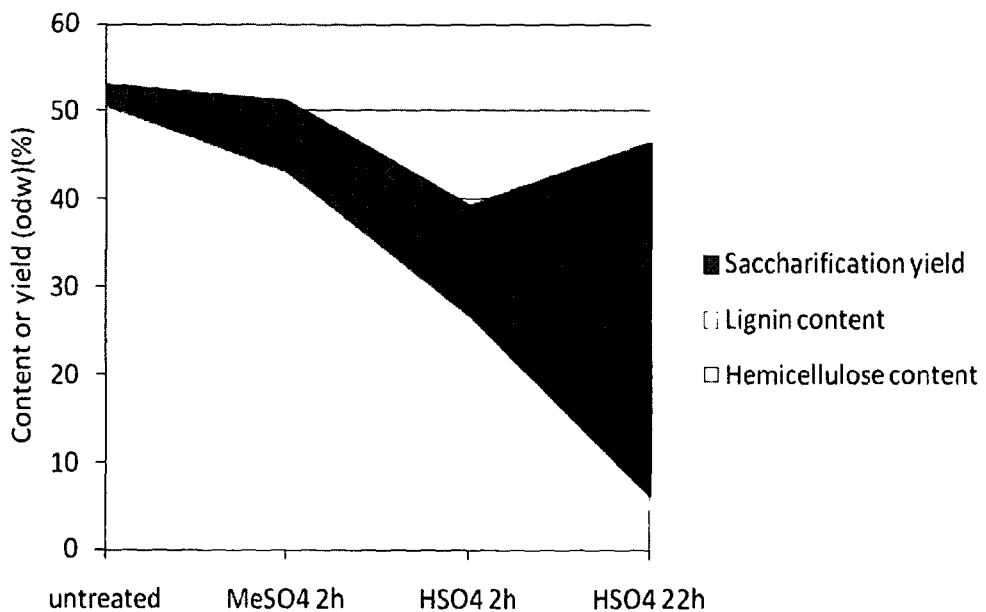
FIG. 13 shows lignin and hemicellulose content and the glucose yield after enzyme hydrolysis of untreated *Miscanthus* and ionic liquid treated *Miscanthus* pulp. The saccharification yield is based on the oven-dried sample weight before the pretreatment.

The highly enriched cellulose contained in this pulp is very susceptible to enzymatic hydrolysis. The relationship between lignin and hemicellulose removal and saccharification yield of glucose is depicted in FIG. 13. A correlation between lignin removal by ionic liquid pretreatment and saccharification yields has been previously suggested.

Example 7

The Influence of the Anion on Biomass Composition and Saccharification Yields

The impact of $[C_4C_1im][MeSO_4]$ and $[C_4C_1im][HSO_4]$ water mixtures was investigated and revealed that efficient lignocellulose pretreatment can be carried out using these pretreatment solvents. To further assess which features make the ionic liquid effective, the influence of the anion was investigated. The effect of the ionic liquid anion had been a focus previously and proved to be an important factor in promoting cell wall swelling.

The condition that has been investigated most thoroughly so far, namely pretreatment with $[C_4C_1im][HSO_4]_{80\%}$ at 120° C. for 22 h, was also selected for the investigation of the anion effect. The anions used for the comparison were acetate, chloride, methanesulfonate and trifluoromethansulfonate. The effectiveness of the pretreatment could not be correlated with the hydrogen-bond basicity of the anion.

Figure 14:
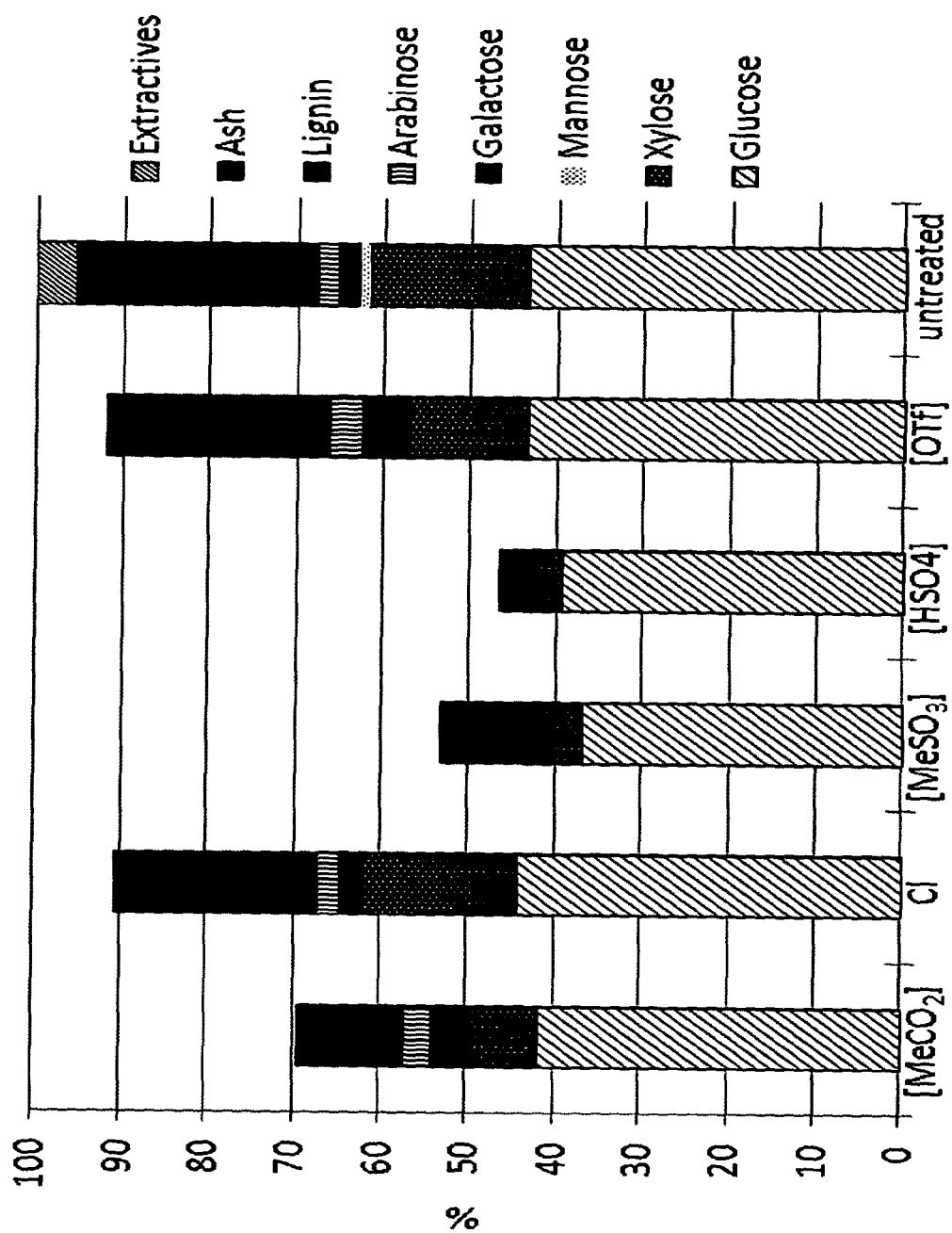
FIG. 14 shows the impact of pretreatment with 80/20% v/v ionic liquid water mixtures on the composition of *Miscanthus*. The anions are ordered according to their hydrogen-bond acceptor strength.

The impact on the composition and the mass loss is depicted in FIG. 14. The results have been ordered according to the hydrogen-bond basicity of the respective anions, with high values on the left. It is clear that the $[HSO_4]^-$ anion caused the greatest mass loss, concomitant with a thorough removal of lignin and hemicellulose.

The second most efficient pulping was found for the $[MeSO_3]^-$ anion. The hemicellulose content was reduced to similar levels, but the lignin content was significantly higher. A significant reduction of hemicellulose and lignin content was observed for pretreatment with the acetate ionic liquid. However, the pulping was significantly less efficient under these conditions. The effect of the chloride containing ionic liquid was surprisingly small. The smallest impact on the composition was exerted by $[C_4C_1im][OTf]$ (trifluoromethanesulfonate).

Figure 15:
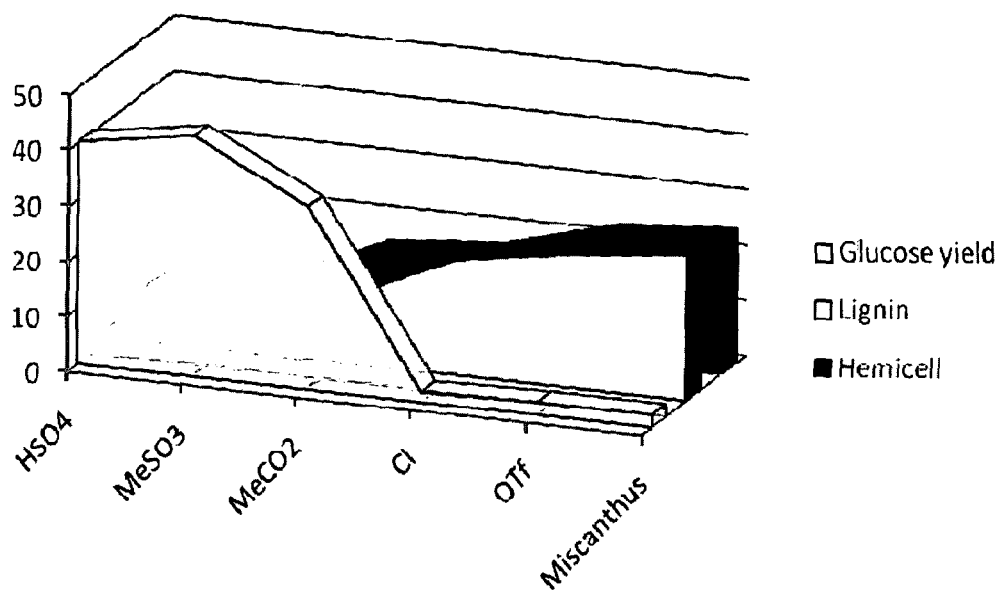
FIG. 15 shows qualitative correlation between lignin and hemicellulose content and cellulose digestibility.

A correlation between the removal of hemicellulose and lignin and the saccharification yields was found (FIG. 15). The highest glucose yields were obtained with $[C_4C_1im][MeSO_3]$ and $[C_4C_1im][HSO_4]$ water mixtures. Pretreatment with $[C_2C_1im][MeCO_2]$ resulted in good glucose yields, but it did not achieve the same level of digestibility as the methanesulfonate and hydrogensulfate based pretreatment solvents. The glucose yields from mixtures containing chloride and triflate ions were very low.

Figure 16:
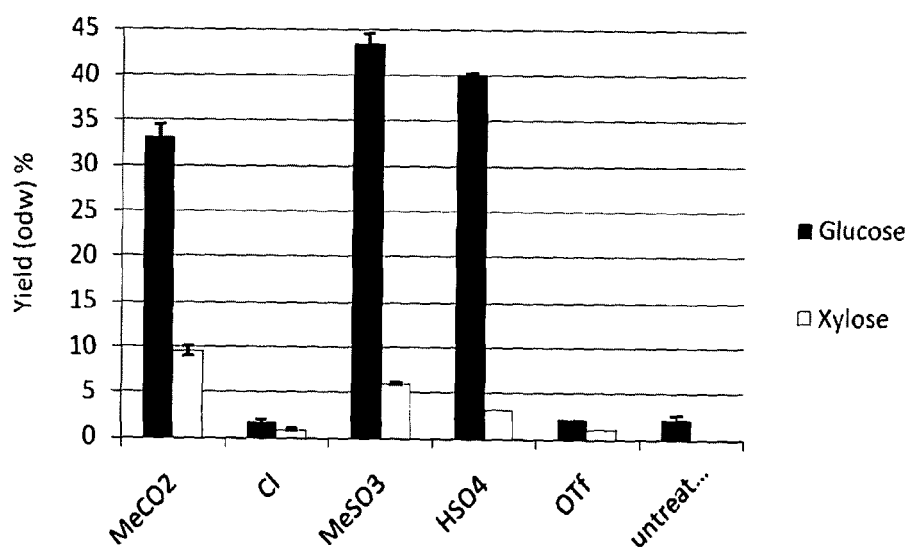
FIG. 16 shows saccharification yield after pretreatment with 80/20% v/v ionic liquid water mixtures at 120° C. for 22 h. Yields were determined after 96 h. Yields are based on the oven-dried sample weight before the pretreatment.

The hemicellulose yields behaved slightly different (FIG. 16). The yield was the highest after $[C_2C_1im][MeCO_2]$ treatment (9.6%), intermediate after $[C_4C_1im][MeSO_3]$ pretreatment (6.0%) and lower after $[C_4C_1im][HSO_4]$ treatment (3.3%). This seems to correlate with the acidity of the ionic liquid mixtures, which has a profound effect on the stability of the hemicellulose fraction.

The acetate anion can exert a buffering effect on an aqueous solution limiting the hydrolysis of glycosidic bonds. Methanesulfonate, as the base of a strong acid, cannot perform such a function and more hydrolysis is observed. Hydrogensulfate is even more acidic and will decrease the pH to 2 or lower. This will not only assist in hemicellulose hydrolysis but encourage further reactions of sugar monomers to furfurals and possibly other degradation products.

Figure 17:
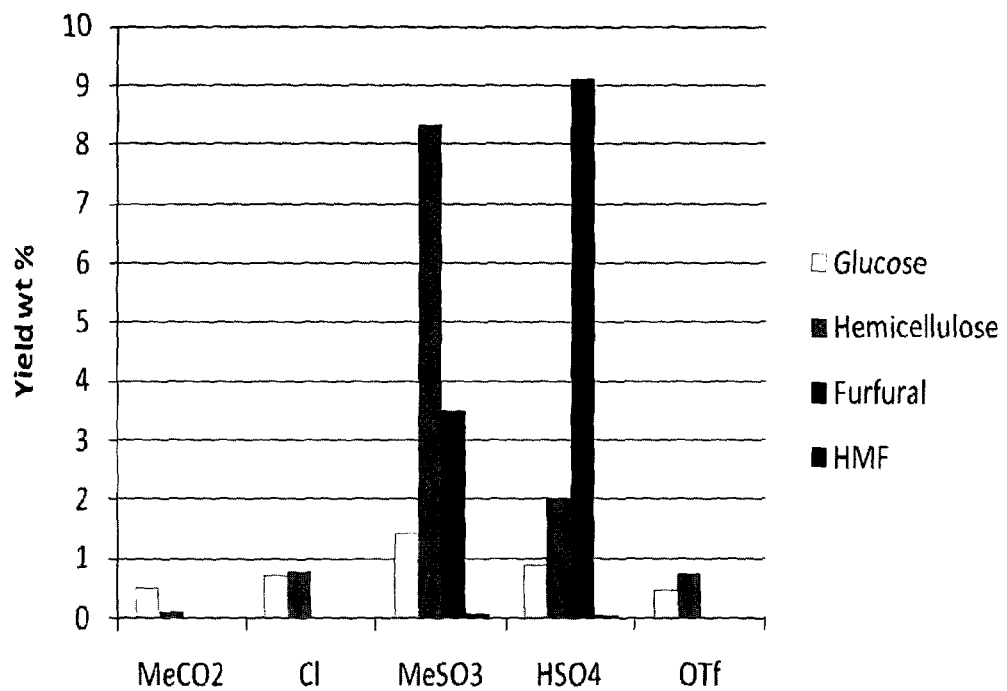
FIG. 17 shows concentrations of solubilised sugars and sugar dehydration products in pretreatment liquors. Yields are based on the oven-dried sample weight before the pretreatment.

The quantities of sugar monomers and furfurals found in the pretreatment liquor are shown in FIG. 17. The pretreatment with [$C_2C_1$im][$MeCO_2$] resulted in a very low quantity of monomers and practically no furfurals. A large fraction of the hemicellulose is recovered in pulp (63% of all hemicellulose). The remaining cellulose was probably solubilised but oligomeric and could not be detected with the available HPLC setup.

Substantial quantities of monomers and furfurals were found in the [$MeSO_3$]$^-$ and [$HSO_4$]$^-$ containing liquors. 13.3 wt % and 12.1 wt % of the original biomass were detected as monomers or monomer dehydration products in both liquids. The distribution among the various products varied considerably. The monomeric hemicellulose was the prevalent fraction in the methanesulfonate liquor, while furfural was the major fraction in the hydrogensulfate liquor.

The chloride and [OTf]$^-$ containing liquors both had a low abundance of monomers and dehydration products, which is no surprise given the negligible fractionation and little mass loss they achieved.

Figure 18:
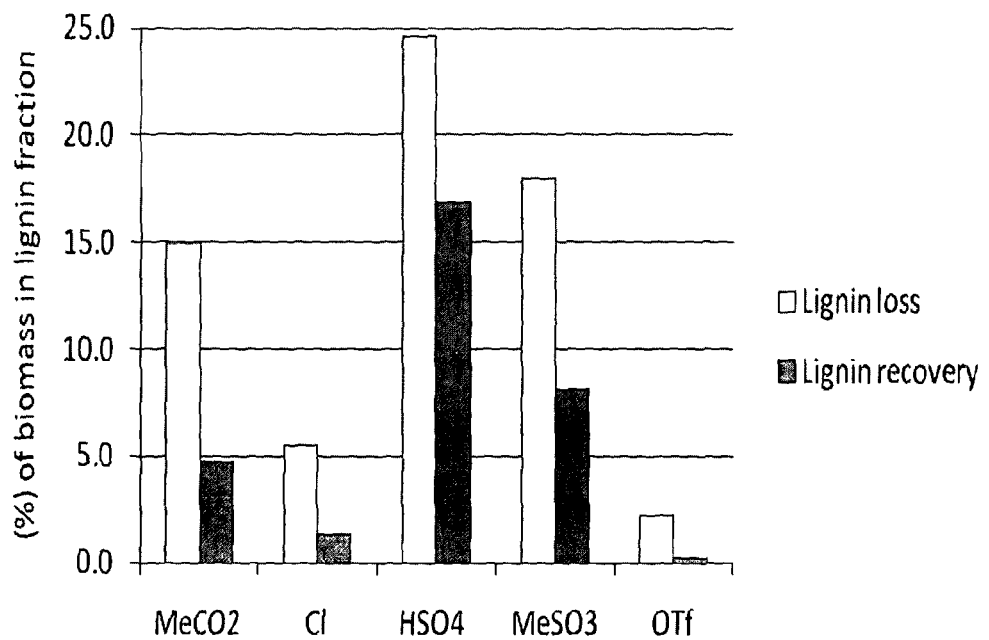
FIG. 18 shows the influence of the anion on delignification and on the lignin recovery after precipitation. Ground *Miscanthus* was pretreated with ionic liquid water mixtures at 120° C. for 22 h. The ionic liquid cation was $[C_4C_1im]^+$, except in $[C_2C_1im][MeCO_2]$. Yields are based on the oven-dried sample weight before the pretreatment. The original lignin content was 26.5%.

The lignin recovery was also determined for 80/20 vol % ionic liquid water mixtures (FIG. 18). The removal of lignin from the biomass (delignification) is also shown in this diagram.

The lignin recovery was best in [$C_4C_1$im[$HSO_4$]$_{80\%}$ with a recovery of 64% of the original lignin, followed by 31% lignin recovery from [$C_4C_1$im[$MeSO_3$]$_{80\%}$ and 18% of all lignin from [$C_2C_1$im[$MeCO_2$]$_{80\%}$.

Example 8

The Influence of the Lignocellulose Type

Figure 19:
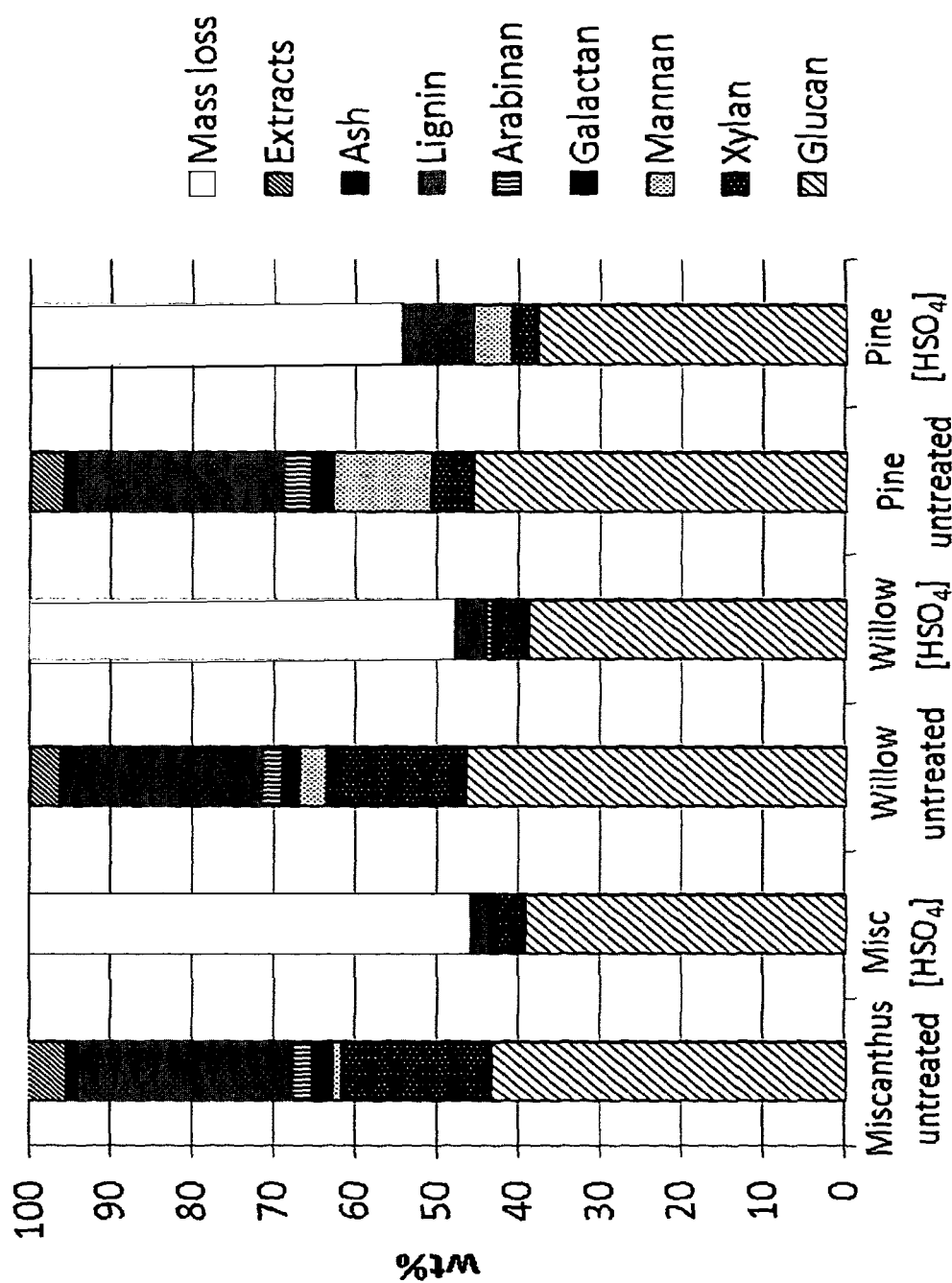
FIG. 19 shows composition of ground *Miscanthus*, willow and pine before and after pretreatment with 80/20% v/v $[C_4C_1im][HSO_4]$ water mixture.

The [$C_4C_1$im][$HSO_4$]$_{80\%}$ pretreatment at 120° C. for 22 h was also performed on ground willow and ground pine. The impact on the biomass composition is shown in FIG. 19. It shows that the pretreatment has a similar effect on the other biomass types. Particularly the impact on willow was very similar compared with the effect on *Miscanthus*, with advanced solubilisation of hemicellulose and lignin. The effect on pine was less pronounced.

Figure 20:
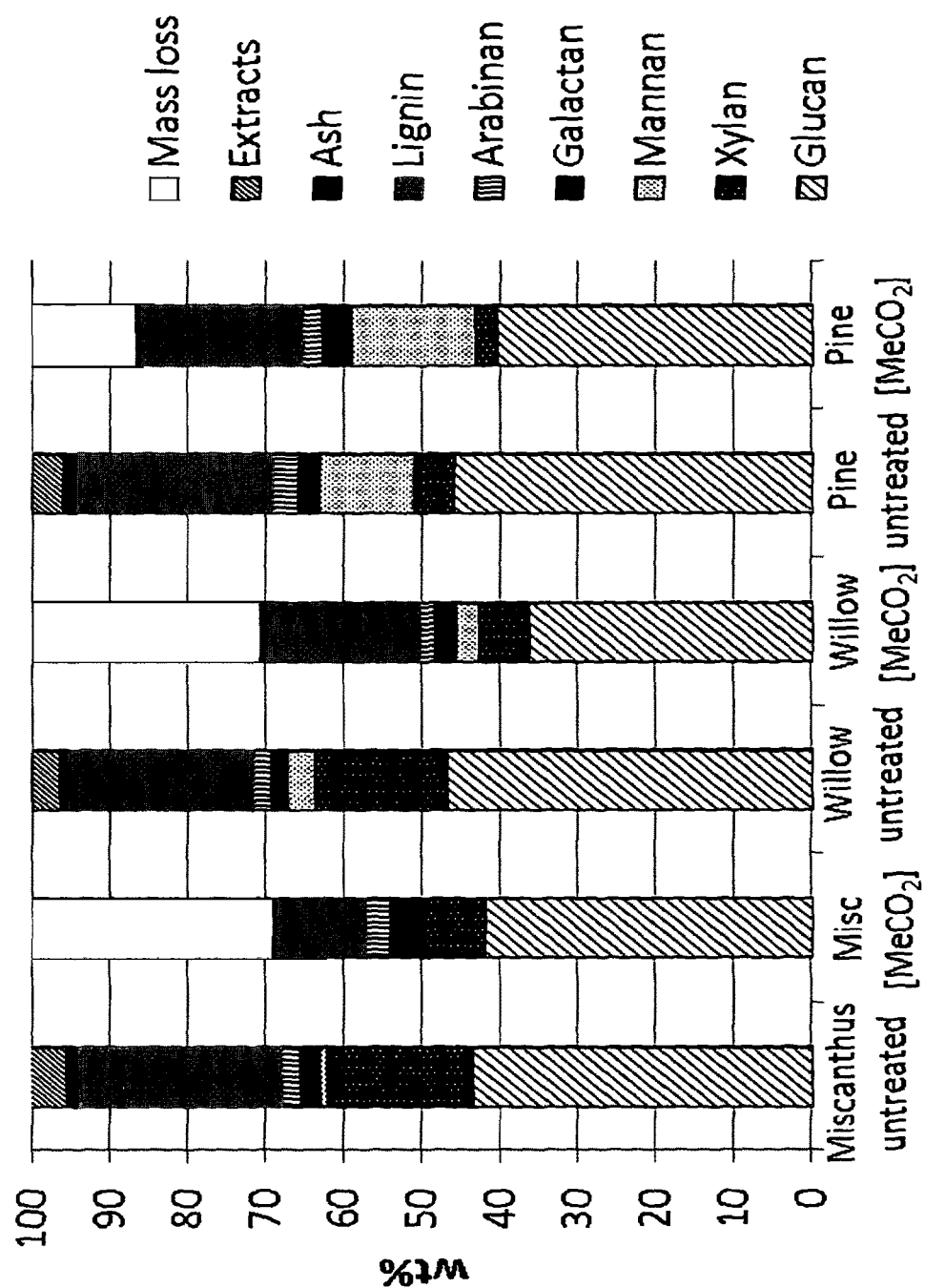
FIG. 20 shows effect of pretreatment of different types of lignocellulosic biomass with 80/20% v/v $[C_2C_1im][MeCO_2]$ water and 80/20% v/v $[C_4C_1im][HSO_4]$ water mixture on the composition.

The various biomass types were also pretreated with [$C_2C_1$im][$MeCO_2$]$_{80}$%. The impact on the biomass composition is shown in FIG. 20. Less delignification and less hemicellulose removal was observed when the anion was acetate, irrespective of the biomass type. The general trend was again, that the pine flour was more recalcitrant to the pretreatment. The [$C_2C_1$im][$MeCO_2$]$_{80\%}$ liquor had very little impact on the pine composition, with some solubilisation of lignin. There was also some loss of the glucose fraction during pretreatment with [$C_2C_1$im][$MeCO_2$]$_{80}$%. This is attributed to the solubility of cellulose in the acetate ionic liquid. Although most of the cellulose was precipitated during washing the pulp with methanol, it was observed that some biomass remained dispersed in the diluted liquor and would only precipitate after further dilution.

The reduced activity on willow and pine compared to *Miscanthus* can be explained by their thicker cell walls and smaller pores. This will results in mass transfer limitation. The differences in the composition and the natural abundance of chemical linkages within the lignin or between the lignin and the hemicellulose could also be responsible.

Figure 21:
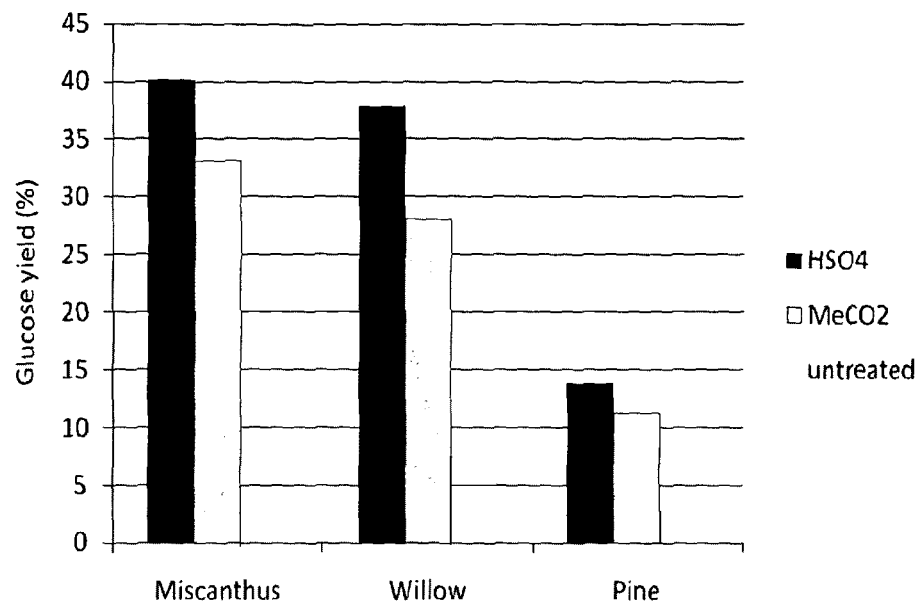
FIG. 21 shows glucose yield after pretreatment with 80/20% v/v ionic liquid water mixtures and 96 h of saccharification of the resulting pulp. Yields are based on the oven-dried sample weight before the pretreatment.

The saccharification results reflect the compositional changes. Removal of lignin and hemicellulose coincided with better digestibility of the cellulose fraction (FIG. 21). The highest digestibility was obtained for *Miscanthus* biomass pretreated with [$C_4C_1$im][$HSO_4$]$_{80\%}$. The second best yield was obtained for willow with the same pretreatment liquor. The order for the biomass anion combinations tested was *Miscanthus* [$HSO_4$]$^-$>Willow [$HSO_4$]$^-$>*Miscanthus* [$MeCO_2$]$^-$>Willow [$MeCO_2$]$^-$>Pine [$HSO_4$]$^-$>Pine [$MeCO_2$]$^-$. The saccharification yields for pine were surprisingly low. Significant delignification (66%) and hemicellulose removal (69%) was observed for pine pretreated with [$C_4C_1$im][$HSO_4$]$_{80\%}$, however, the glucose yield was only 30% of the theoretically possible yield.

Figure 22:
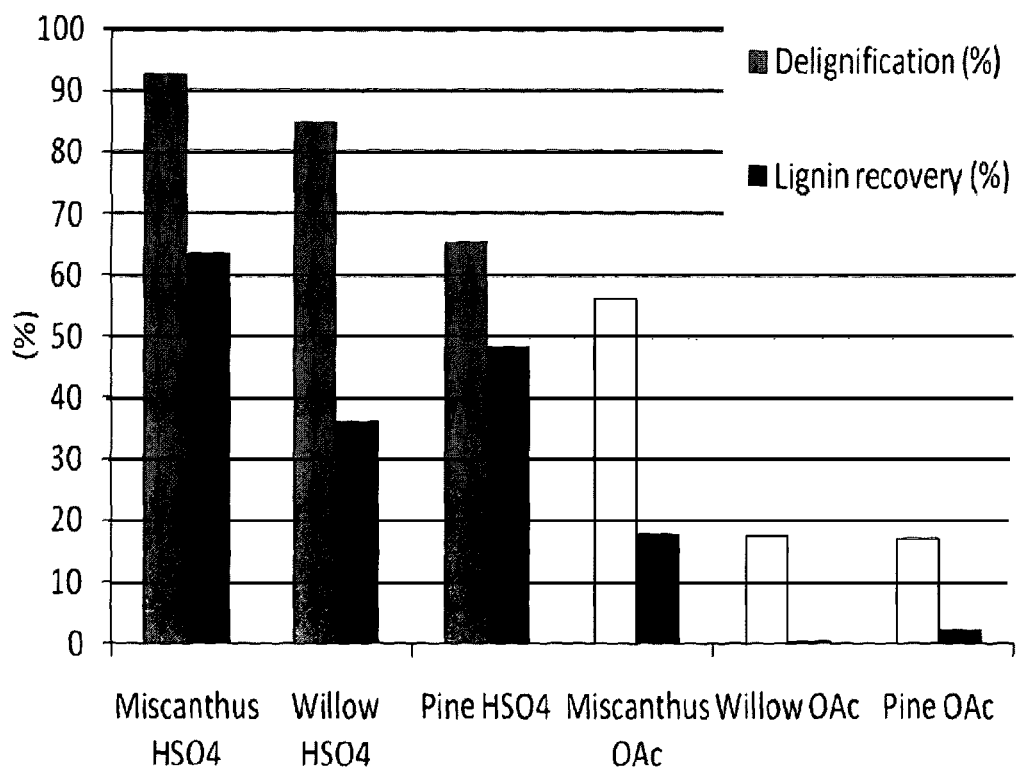
FIG. 22 shows delignification and recovery of lignin after pretreatment with 80/20% v/v ionic liquid water mixtures. The ionic liquids were $[C_4C_1im][HSO_4]$ and $[C_2C_1im][MeCO_2]$. No replicates were obtained. The yield is displayed as percentage of lignin in the untreated biomass.

The lignin yields are shown in FIG. 22, together with the delignification efficiencies. The delignification was generally higher with [$C_4C_1$im][$HSO_4$]$_{80\%}$ than with [$C_2C_1$im][$MeCO_2$]$_{80\%}$. Moreover, the lignin recovery appears to be better from the [$C_4C_1$im][$HSO_4$]$_{80\%}$ liquor.

It has been reported that acidification of the pretreatment liquor improves the lignin recovery. This might be the main advantage of using a hydrogen sulfate ionic liquid, as this ionic liquid is already acidic itself. The poor delignification with [$C_2C_1$im][$MeCO_2$]$_{80\%}$ is probably due to the high water content. A negative correlation between the water content and lignin removal with [$C_2C_1$im][$MeCO_2$] has already been demonstrated.

Example 9

Pretreatment of *Miscanthus* and Willow Chips

Both *Miscanthus* and willow appeared to be very good substrates for pretreatment with [$C_4C_1$im][$HSO_4$]$_{80\%}$. So far, the substrate was ground biomass. A truly energy-efficient pretreatment process, however, will use coarsely chopped biomass, as grinding is a energy-intensive operation. Therefore the pretreatment efficiency of [$C_4C_1$im][$HSO_4$]$_{80\%}$ was tested on chips-sized biomass. For *Miscanthus* chips, a substantial disintegration of the less recalcitrant pith was observed. The structure was softened and fragile upon mechanical impact. There was also a fine powder which settled on the filter paper, which must be parts of the cell wall that have dissociated from the chips.

Willow chips also underwent significant changes upon pretreatment. In addition to discoloration, the chips were significantly easier to break down. Untreated pine chips require strong mechanical impact in order to break them up, e.g. sawing or grinding, while the pretreated chips could be broken up using a blunt spatula. This suggests that the pretreatment of chips with ionic liquids prior to grinding can reduce the energy required for comminution.

Figure 23:
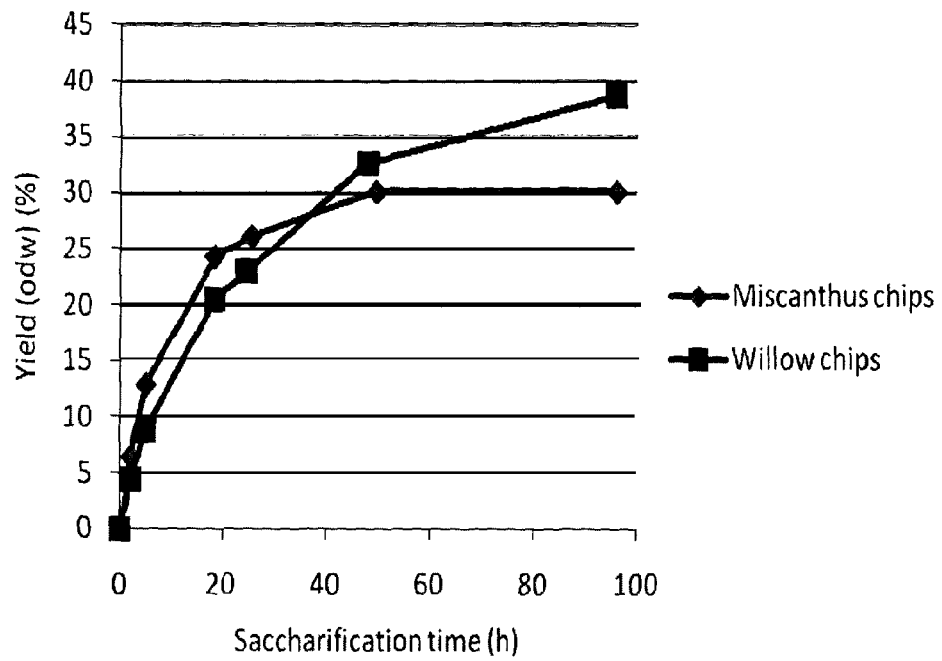
FIG. 23 shows saccharification time course of *Miscanthus* and willow chips. Yields are based on the oven-dried sample weight before the pretreatment.

The glucose yields obtained from chip-sized biomass are depicted in FIG. 23. The enzyme hydrolysis of the *Miscanthus* cellulose proceeded faster, but came to a halt after 48 h. Only 70% of the glucose was liberated in the saccharification, compared to >85% obtained from ground material. A visible check of the residue showed that the left-over was material from the recalcitrant outer ring. The saccharification yield from willow chips was surprisingly good, reaching levels comparable to ground biomass (84% glucose recovery compared to 81% from ground willow). The thicker cell walls of hardwood and the reduced surface area were probably responsible for the slower saccharification.

Example 10

The Influence of Water on the Effectiveness of Ionic Liquid Pretreatment.

A notation to indicate the amount of the ionic liquid contained in the pretreatment solvent/liquor was devised. This involves a subscript being added to the usual ionic liquid notation indicating the ionic liquid content in volume percent (vol %), with the remainder being water. An example is $[C_4C_1im][MeSO_4]_{80\%}$, which is a mixture of 80 vol % $[C_4C_1im][MeSO_4]$ and 20 vol % water. Conversions of vol % into weight percent (wt %) and mole percent (mol %) were calculated and are listed in Table 1. When allowing $[C_4C_1im][MeSO_4]$ to equilibrate with the moisture in the laboratory air a water content of 70,400 ppm or 7.0 wt % was measured (last entry of Table 1 Table 1). Although the moisture content of air is variable, the measurement demonstrates the highly hygroscopic nature of this ionic liquid.

TABLE 1

Ionic liquid concentration in aqueous pretreatment liquors.

| Mixture | Volume percent (vol %) | Weight percent (wt %) | Molar percent (mol %) |
|---|---|---|---|
| $[C_4C_1im][MeSO_4]_{98\%}$ | 98 | 98 | 81 |
| $[C_4C_1im][HSO_4]_{95\%}$ | 95 | 96 | 64 |
| $[C_4C_1im][MeSO_4]_{90\%}$ | 90 | 92 | 44 |
| $[C_4C_1im][HSO_4]_{90\%}$ | | | 46 |
| $[C_4C_1im][MeSO_4]_{80\%}$ | 80 | 83 | 26 |
| $[C_4C_1im][HSO_4]_{80\%}$ | | 83 | 27 |
| $[C_4C_1im][MeSO_3]_{80\%}$* | | 82 | 26 |
| $[C_2C_1im][MeCO_2]_{80\%}$ | | 82 | 32 |
| $[C_4C_1im]Cl_{80\%}$* | | 81 | 30 |
| $[C_4C_1im][OTf]_{80\%}$ | | 84 | 24 |
| $[C_4C_1im][MeSO_4]_{60\%}$ | 60 | 65 | 12 |
| $[C_4C_1im][HSO_4]_{60\%}$ | | | |
| $[C_4C_1im][MeSO_4]_{40\%}$ | 40 | 45 | 6 |
| $[C_4C_1im][HSO_4]_{40\%}$ | | | |
| $[C_4C_1im][MeSO_4]_{20\%}$ | 20 | 23 | 2 |
| $[C_4C_1im][HSO_4]_{20\%}$ | | | |
| $[C_4C_1im][MeSO_4]_{wet}$ | n.a. | 93 | 49 |

*These ionic liquids are solid at room temperature. Therefore vol % and wt % were calculated using the density at 80° C.

The aim of this work is to investigate the effect of the composition of the ionic liquid liquor on the pretreatment. Solid recovery, pulp composition, its enzymatic digestibility, the precipitation of a lignin-containing fraction and the production of furfurals in the liquor were investigated. The application of an ionic liquid with a monoalkylated imidazolium cation was also examined. Pretreatment of different feedstocks was carried out to assess their recalcitrance towards pretreatment with ionic liquid water mixtures.

Tissue Softening of *Miscanthus* Chips

In preliminary experiments, we observed substantial disintegration of *Miscanthus* cross sections immersed in the ionic liquid 1-butyl-3-methylimidazolium methyl sulfate, $[C_4C_1im][MeSO_4]$, when heated above 80° C. This encouraged us to investigate the application of this ionic liquid for biomass pretreatment. The use of $[C_4C_1im][MeSO_4]$, dried to a water content below 0.3 wt %, resulted in formation of a degraded biomass-ionic liquid composite that was not enzymatically digestible. In contrast, using a mixture of 80 vol % ionic liquid and 20 vol % water yielded a solid fraction that was separable from the (intensely coloured) ionic liquid fraction and highly digestible. It was concluded that a certain amount of water was necessary for successful pretreatment with $[C_4C_1im][MeSO_4]$. In the "dry" sample, 0.3 wt % water was contained in the ionic liquid as residual moisture and 0.7 wt % was introduced with the air-dried biomass containing 8 wt % moisture, supplying 1.1 wt % or 15 mol % water in total. This was apparently not sufficient to obtain an enzymatically digestible pulp.

Example 11

Figure 24:
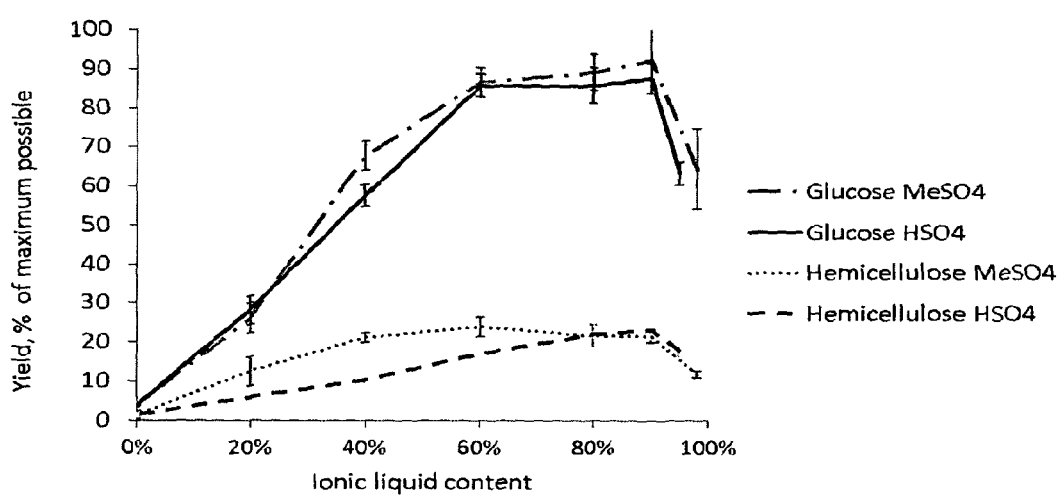
FIG. 24 shows sugar yields obtained from *Miscanthus* pulp after pretreatment with $[C_4C_1im][MeSO_4]$ or $[C_4C_1im][HSO_4]$ water mixtures at 120° C. The $[C_4C_1im][MeSO_4]$ pretreatment was carried out for 22 h, while $[C_4C_1im][HSO_4]$ pretreatment lasted 13 h, and the saccharification 96 h. The yields are based on the glucan and hemicellulose content of the untreated biomass.

Influence of the Water Content on the Saccharification Yield after Ionic Liquid Pretreatment with $[C_4C_1im][MeSO_4]$ A range of ionic liquid water mixtures were used for pretreatment of *Miscanthus* to explore the effect of the water content in more detail. The effect of water on the enzymatic release of glucose and hemicellulose is shown in FIG. 24. The yields are calculated based on the glucose and hemicellulose content found in the untreated *Miscanthus* feedstock (on an oven-dry basis), which were 43.6 wt % and 24.3 wt %, respectively. In preliminary experiments, it was shown that the only detectable hemicellulose sugar released during saccharification was xylose.

The best saccharification yields were obtained after pretreatment with mixtures containing 60-90 vol % ionic liquid. Pretreatment with $[C_4C_1im][MeSO_4]_{90\%}$, resulted in the release of 92% of the glucose originally contained in the biomass. Pretreatment with $[C_4C_1im][MeSO_4]_{80\%}$ and $[C_4C_1im][MeSO_4]_{60\%}$, resulted in the release of 89% and 87% based on the original glucan content. Glucose yields decreased when the ionic liquid content was higher or lower. The hemicellulose yield was significantly lower than the glucose yield, regardless of the mixture composition; 24% of the hemicellulose sugars (based on the initial hemicellulose content) were released after $[C_4C_1im][MeSO_4]_{60\%}$ pretreatment. Similar yields were obtained with mixtures containing 40-90 vol % $[C_4C_1im][MeSO_4]$.

Example 12 Attempted Recycling of $[C_4C_1im][MeSO_4]$

When attempting to recycle $[C_4C_1im][MeSO_4]$, we found that the ionic liquid anion was partially hydrolysed. After recording a mass spectrum of the recovered ionic liquid, a high abundance of a negatively charged species at m/z=97 was detected, which was ascribed to the hydrogen sulfate, $[HSO4]^-$, anion. This led to the conclusion that the ester bonds in methyl sulfate anions are hydrolytically unstable under the conditions of the pretreatment and mixtures of the ester and the hydrolysed form are produced.

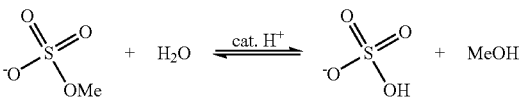

The extent of anion hydrolysis depended on the water content of the liquor (FIG. 25). The more water was present in the mixture, the greater the anion hydrolysis, with exception of mixtures where the water content was higher than 90 mol %. These results suggest that without extreme precautions to protect $[MeSO_4]^-$ containing ionic liquids, $[HSO_4]^-$ will be present and other studies using these ionic liquids should be interpreted in this light.[20]

Example 13 Influence of the Water Content on the Enzymatic Saccharification of $[C_4C_1im][HSO_4]$ Treated *Miscanthus*

With the knowledge that the binary 1-butyl-3-methylimidazolium methyl sulfate water mixtures turned into quaternary mixtures of two ionic liquids plus two molecular solvents (water and methanol) we set out to identify the active component(s). *Miscanthus* was pretreated with aqueous mixtures of $[C_4C_1im][HSO_4]$, which allowed us to exclude methyl sulfate and methanol. The saccharification yields obtained from the pulps pretreated with various $[C_4C_1im][HSO_4]$ water mixtures are shown in Figure. The glucose yields were almost identical to the glucose yields obtained with the quaternary mixtures. The pattern of hemicellulose release was also similar, however, after $[C_4C_1im]$ $[HSO_4]_{40\%-80\%}$ pretreatment, less hemicellulose was recovered than after treatment with the equivalent methyl sulfate containing mixtures.

A glucose recovery of 90% after ionic liquid pretreatment is a substantial improvement compared with the saccharification yields reported after pretreatment with other ionic liquids. It has been reported that 74% glucose was enzymatically released from ground maple wood after $[C_4C_1im]$ $[MeCO_2]$ treatment at 90° C. for 24 h. 70% glucose was released from maple wood after $[C_2C_1im][MeCO_2]$ treatment at 90° C. for 24 h. Li et al. reported only 15% glucose release from ground *Eucalyptus*, pretreated with 1-allyl-3-methylimidazolum chloride, $[C=C_2C_1im]Cl$, at 120° C. for 5 h, while 55% of the glucose was released after 1-ethyl-3-methylimidazolium diethyl phosphate, $[C_2C_1im][Et_2PO_4]$, pretreatment of ground wheat straw at 130° C. for 30 min. It should be noted that saccharification yields obtained from ball-milled lignocellulose samples were not considered for this listing because fine milling can have a considerable effect on cellulose digestibility.[22] The use of ground material reduces the economic viability,[31] but using fine powders obtained by ball-milling is of very little relevance for an industrial process. Studies using 3,5-dinitrosalicylic acid (DNS) for the determination of glucose yield were also not considered. The test is not specific for glucose and therefore glucose yields from lignocellulose are often overestimated.

Example 14 Effect of Pretreatment Time on the Enzymatic Saccharification

Next, we were interested in the optimisation of the pretreatment time. FIG. 26 shows the saccharification yields for both $[C_4C_1im][MeSO_4]_{80\%}$ and $[C_4C_1im][HSO_4]_{80\%}$ pretreatment after various lengths of time. It can be seen that the enhancement of the cellulose and hemicellulose digestibility mainly occurred within the first 4 h. This was also the period of where the mass loss increased significantly. The pretreatment was practically complete after 8 h, achieving around 80% glucose and 30% hemicellulose release. When prolonging the pretreatment, the glucose yield slightly increased to above 85%, but the hemicellulose yield decreased to just over 20%. This experiment shows that the presence or absence of methyl sulfate in the pretreatment mixture does not significantly influence the speed of the pretreatment. It is anticipated that the pretreatment time can be shortened by the application of higher temperatures, but it must be balanced with the ionic liquid stability and potential side reactions.

Example 15 the Effect of $[C_4C_1im][MeSO_4]_{80\%}$ and $[C_4C_1im][HSO_4]_{80\%}$ Pretreatment on Biomass Composition The composition of untreated *Miscanthus* and pretreated pulp is shown in Table 2 and FIG. 27. The untreated biomass contained 43.6% glucose, 24.3% hemicellulose and 26.5% lignin. After pretreatment with $[C_4C_1im][MeSO_4]_{80\%}$ for 2 h, the main effect was a reduction of the lignin content. Treatment with $[C_4C_1im][HSO_4]_{80\%}$ for 2 h resulted in the removal of lignin and hemicellulose. After an extended pretreatment for 22 h, most of the lignin and hemicellulose was solubilised and the glucan content increased from 44% in the untreated biomass to 85% in the pretreated biomass. 91% of the original glucan was still present in the pulp. The biomass recovery after 22 h was less than 46%, showing that more than half of the wood had been solubilised in the ionic liquid. Tan et al. reported a mass recovery between 46% and 55% after pretreatment with $[C_2C_1im][ABS]$ at 170-190° C., indicating that this ionic liquid mixture might be capable of similar biomass fractionation. The simultaneous removal of lignin and hemicellulose has also been reported for $[C_2C_1im][MeCO_2]$, albeit less complete than seen in this study with $[C_4C_1im][HSO_4]_{80\%}$.

TABLE 2

Composition of untreated Miscanthus and Miscanthus pretreated with $[C_4C_1im][MeSO_4]$ and $[C_4C_1im][HSO_4]$.

| | Glu | Xyl | Ara | Man | Gal | Lignin | Ash | Extractives | Mass loss |
|---|---|---|---|---|---|---|---|---|---|
| untreated | 43.6 | 18.3 | 3.4 | 1.1 | 2.4 | 26.5 | 1.3 | 4.7 | 0 |
| [MeSO$_4$] 2 h | 45.4 | 18.3 | 2.1 | 1.3 | 2.2 | 19.3 | 1.1 | — | 10 |
| [HSO$_4$] 2 h | 44.5 | 8.6 | 0 | 0 | 3.4 | 14.9 | 0.6 | — | 28 |
| [HSO$_4$] 22 h | 39.5 | 3.3 | 0 | 0 | 1.1 | 1.9 | 0.6 | — | 56 |

Example 16 Production of Solubilised Sugars and Furfurals

As seen above, the hemicellulose was removed from the biomass during treatment with $[C_4C_1im][HSO_4]$ and $[C_4C_1im][MeSO_4]$ water mixtures. It is likely that under the conditions of the pretreatment, (partial) hydrolysis of solubilised hemicellulose occurred. Therefore the concentration of monomeric carbohydrates in the pretreatment liquor was investigated. FIG. 28 shows the relative amount of hemicellulose sugars and glucose in $[C_4C_1im][HSO_4]_{80\%}$ and $[C_4C_1im][MeSO_4]_{80\%}$ liquors at different time points. The amount of hemicellulose monomers in the liquor increased within the first 4 h. The increase was more pronounced in the $[C_4C_1im][HSO_4]_{80\%}$ liquor. The maximum amount of hemicellulose monomers was detected around 4-8 h. This coincided with a major increase of cellulose digestibility after 4-8 h of treatment. Subsequently, the hemicellulose concentration in the pretreatment liquor decreased, suggesting that conversion of carbohydrate monomers into furfurals was occurring.

Furfural was detected in the ionic liquid liquors and quantified for selected mixtures (FIG. 29). The glucose content was significantly lower than the hemicellulose sugar content and hardly changed over time. The smaller amount of solubilised glucose is ascribed to the slow hydrolysis of cellulose under the conditions of the pretreatment and the decomposition of glucose to HMF. The small amount of HMF might be due to its decomposition to other degradation products in the presence of water.

Example 17 Lignin Recovery

We attempted to recover lignin from the liquor (FIG. 30), as this has been successfully demonstrated for other ionic liquids. It was found that diluting the ionic liquid liquor with water precipitated a fine powder. The powder was characterised by IR spectroscopy and comparison with a spectrum of a reference lignin (alkaline lignin) showed that the precipitate is likely to be mostly lignin (FIGS. 31-34). When methanol was used for washing the pulp, instead of water, the majority of the precipitate remained in solution and a 15-20% improvement of precipitate recovery was observed. Therefore washing the pulp with methanol was preferred. The final protocol consisted of washing the pulp with methanol, drying the combined ionic liquid fractions by evaporating the methanol, and precipitating the lignin by diluting the dried ionic liquid liquor with water. The precipitate was washed with copious amounts of water and dried before the yield was determined. The data (FIG. 30) show that the yield of precipitate was up to 50% of the Klason lignin content of the untreated biomass. More precipitate was obtained when the ionic liquid content in the pretreatment liquor was high.

We also examined the time dependency of the precipitate yield and observed that the yield of precipitate plateaued within 8 h (FIG. 34). The yield was slightly higher from $[C_4C_1im][HSO_4]_{80\%}$ compared to $[C_4C_1im][MeSO_4]_{80\%}$.

Example 18 the Effect of the Ionic Liquid Cation

The use of ionic liquids with mono-alkylated imidazolium cations (1-alkylimidazolium, $[C_nHim]^+$) is advantageous from an industrial point of view, as the ionic liquids are easier to synthesise and thus cheaper to produce. Therefore an exemplary pretreatment of *Miscanthus* with 1-butylimidazolium hydrogen sulfate, $[C_4Him][HSO_4]$, was carried out. The sugar yields after treatment with $[C_4Him][HSO_4]_{80\%}$ and a subsequent enzymatic saccharification are shown in FIG. 35. After 4 h pretreatment, 69% of the original glucose and 10% of the original hemicellulose were enzymatically released. The yield was somewhat improved by prolonging the treatment to 20 h, when 75% of the glucose was recovered. However, the xylose yield was reduced to only 3%. Pretreatment with $[HC_4im][HSO_4]_{95\%}$ resulted in significantly reduced glucose yields (44%).

The results of the compositional analysis and the mass loss of $[C_4Him][HSO_4]$ treated *Miscanthus* are presented in Table 3 and FIG. 36. 80-93% of the lignin and more than 95% of the hemicellulose were removed. The thorough removal of hemicellulose is reflected by the low xylose yields obtained during saccharification. Treatment with $[C_4Him][HSO_4]_{95\%}$ not only resulted in the solubilisation of lignin and hemicellulose, but also in a substantial removal of the cellulose fraction (51% of the glucan), explaining the reduced glucose yield shown in FIG. 35. The results indicate that pretreatment with $[C_4Him][HSO_4]$ was harsher than with $[C_4C_1im][HSO_4]$ under comparable conditions, potentially due to the increased acidity of the $[C_4Him][HSO_4]$ compared to $[C_4C_1im][HSO_4]$.

TABLE 3

Composition of Miscanthus pretreated with $[C_4Him][HSO_4]_{80\%}$ and $[C_4Him][HSO_4]_{95\%}$ at 120° C. Values are given in %; Glu = glucan, Xyl = xylan, Man = mannan, Gal = galactan, Ara = arabinan.

| IL content, treatment time | Glu | Xyl | Man | Gal | Ara | Lignin | Ash | Mass loss |
|---|---|---|---|---|---|---|---|---|
| 80%, 4 h | 40.9 | 2.9 | 0 | 0.7 | 0.2 | 5.0 | 0.8 | 49.5 |
| 80%, 20 h | 37.7 | 1.0 | 0 | 1.0 | 0 | 5.4 | 0.6 | 54.2 |
| 95%, 20 h | 22.4 | 0.6 | 0 | 0.6 | 0 | 1.9 | 0.4 | 74.2 |

It was also possible to obtain a precipitate upon dilution of the ionic liquid liquor (FIG. 37). For the $[C_4Him][HSO_4]_{80\%}$ liquor, the yield was nearly 100% of the lignin content. For the 95% liquor, the amount of precipitate was almost double the amount of the lignin content. We explain the unusually high precipitate yield with the formation of pseudo-lignin. The formation of water-insoluble carbohydrate degradation products has been observed during biomass pretreatment under severe acidic conditions and found to obscure the Klason lignin yield. Therefore it has been termed pseudo-lignin. The formation of such degradation products is undesirable and optimisation of the pretreatment conditions is required to minimise this.

Example 19 the Effect of the Ionic Liquid Anion on the Composition of Ionic Liquid Treated *Miscanthus*

The effect of treatment with $[C_4C_1im][HSO_4]_{80\%}$ on the composition of *Miscanthus* was compared with the effect that other 20/80 vol % dialkylimidazolium ionic liquid water mixtures have on the composition. The anions that we examined were trifluoromethanesulfonate, $[OTf]^-$, methanesulfonate, $[MeSO_3]^-$, chloride, $Cl^-$, and acetate, $[MeCO_2]^-$. It should be noted that the acetate containing ionic liquid, $[C_2C_1im][MeCO_2]$, was of commercial quality.

TABLE 4

Composition of pretreated Miscanthus after treatment with 80/20% ionic liquid water mixtures at 120° C. for 22 h. Values are given in %; Glu = glucan, Xyl = xylan, Man = mannan, Gal = galactan, Ara = arabinan.

| Ionic liquid anion | Glu | Xyl | Man | Gal | Ara | Lignin | Ash | Mass loss |
|---|---|---|---|---|---|---|---|---|
| $[MeCO_2]^-$ | 41.9 | 7.9 | 0 | 4.0 | 3.4 | 11.6 | 0.5 | 30.6 |
| $Cl^-$ | 44.5 | 17.8 | 0 | 2.3 | 2.7 | 22.5 | 0.7 | 9.5 |
| $[MeSO_3]^-$ | 37.1 | 4.3 | 0 | 2.3 | 0 | 8.5 | 1.0 | 46.8 |
| $[HSO_4]^-$ | 39.5 | 3.3 | 0 | 1.1 | 0 | 1.9 | 0.6 | 53.6 |
| $[OTf]^-$ | 43.6 | 13.7 | 0 | 5.1 | 4 | 24.3 | 1.0 | 8.3 |

FIG. 38 and Table 4 show that the nature of the anion has a profound effect on mass loss and pulp composition. $[C_4C_1im][HSO_4]_{80\%}$ removed lignin and hemicellulose most thoroughly, followed by $[C_4C_1im][MeSO_3]_{80\%}$ and then by $[C_2C_1im][MeCO_2]_{80\%}$. Hardly any change of the composition was observed when the biomass was treated with $[C_4C_1im]Cl_{80\%}$ and $[C_4C_1im][OTf]_{80\%}$, despite the fact that high solubility of Kraft lignin has been reported for both ionic liquids (in anhydrous form). The contradiction could be resolved if lignin solubilisation and lignin extraction (which usually involves chemical modifications) were regarded as different properties.

Example 20 the Effect of the Anion on the Saccharification Yield

Enzymatic saccharification of *Miscanthus* treated with the ionic liquid liquors was also carried out (FIG. 39). In general, the enzymatic glucose release appeared to reflect the extent of compositional change/mass loss achieved during ionic liquid pretreatment. The highest glucose yield was observed after $[C_4C_1im][MeSO_3]_{80\%}$ and $[C_4C_1im][HSO_4]_{80\%}$ pretreatment. The hemicellulose yield behaved slightly differently. The xylose yield was the highest after pretreatment with $[C_2C_1im][MeCO_2]_{80\%}$. The yield was significantly lower after $[C_4C_1im][MeSO_3]_{80\%}$ and $[C_4C_1im][HSO_4]_{80\%}$ pretreatment. Comparatively high hemicellulose yields after $[C_4C_1im][MeCO_2]$ treatment can also be found in the literature. The increased hemicellulose recovery after $[C_2C_1im][MeCO_2]_{80\%}$ treatment could be due to a buffering effect exerted by the basic acetate anion. Its ability to combine with protons to form acetic acid may limit the acid-catalysed hydrolysis of hemicellulose polymers. Inhibition of the hydrolysis of cellobiose by $[C_4C_1im][MeCO_2]$ has been observed in mixtures of the ionic liquid, water and catalytic amounts of strong acid. Binder et al., have also observed inhibition of cellulose depolymerisation in $[C_4C_1im][MeCO_2]$, despite addition of catalytic amounts of HCl. The methanesulfonate anion appears to have a less protective effect and acid-catalysts which are released from the biomass (acetic acid and hydroxycinnamic acids) can aid xylan hydrolysis. Hydrogensulfate increases the amount of available protons, which could explain the particularly low xylan content in the pulp. The glucose and xylose yields obtained after treatment with $[C_4C_1im]Cl_{80\%}$ and $[C_4C_1im][MeSO_3]_{80\%}$ were low, despite their ability to dissolve cellulose and lignin preparations (in case of triflate only lignin solubility).

Example 21 the Effect of the Anion on Delignification and Precipitate Recovery The yield of precipitate seems to be related to the ability of the liquor to extract lignin (FIG. 40). The best delignification and the highest precipitate yield was obtained with $[C_4C_1im][HSO_4]_{80\%}$, followed by $[C_4C_1im][MeSO_3]_{80\%}$ and then $[C_2C_1im][MeCO_2]_{80\%}$. This supports the notion that the precipitate comprises lignin, although it was shown in FIG. 37 that pseudo-lignin also precipitate upon dilution of the ionic liquid liquor.

Example 22 the Effect of the Anion on the Formation of Soluble Degradation Products The quantities of carbohydrate monomers and dehydration products solubilised in the pretreatment liquors are shown in FIG. 41. The $[C_4C_1im][HSO_4]_{80\%}$ and $[C_4C_1im][MeSO_3]_{80\%}$ liquors contained approximately 45% of the total hemicellulose as either sugar monomers or furfural. In $[C_4C_1im][HSO_4]_{80\%}$, the majority of the largest fraction was furfural. Conversion of pentoses into furfurals was also observed in $[C_4C_1im][MeSO_3]_{80\%}$, but to a lesser extent. This is ascribed to the non-acidic nature of this ionic liquid. Only small quantities of monomers were detected in the acetate containing liquor, which is probably due to fact that the solubilised carbohydrates are mostly in oligomeric form. No furfural was formed in $[C_2C_1im][MeCO_2]_{80\%}$ in our experiment. It is likely that the acidity of the liquor is responsible for the varying concentrations of sugar monomers and furfural found in the liquor. Like the hydrolysis of glycosidic bonds, the rate of furfural formation depends on the acid concentration. Since the acidity/basicity of 1,3-dialkylimidazolium ionic liquids is determined by the anion, its nature should have a profound impact on the fate of the solubilised hemicellulose. The amount of solubilised glucose and HMF were small in all cases. This is ascribed to the enhanced stability of the cellulose fraction towards hydrolysis under pretreatment conditions and the propensity of HMF to react to formic and levulinic acid in the presence of water.

Example 23 the Effect of the Biomass Type: Pretreatment of Willow and Pine

Pretreatment with $[C_4C_1im][HSO_4]_{80\%}$ was also performed on ground willow (a hardwood species) and pine (a softwood species). For comparison, willow and pine were also pretreated with $[C_2C_1im][MeCO_2]_{80\%}$. The effect of the pretreatment on the biomass composition is shown in Table 5 and FIG. 42.

TABLE 5

Composition of untreated willow and pine and the pulps after treatment with $[C_4C_1im][HSO_4]80\%$ and $[C_4C_1im][MeCO_2]_{80\%}$.

| | Glu | Xyl | Man | Gal | Ara | Lignin | Ash | Extractives | Mass loss |
|---|---|---|---|---|---|---|---|---|---|
| Willow | 46.7 | 16.8 | 3.6 | 1.9 | 2.5 | 24.1 | 0.7 | 3.7 | 0 |
| Willow, [MeCO$_2$] | 36.3 | 6.4 | 2.9 | 2.7 | 1.9 | 19.9 | 0.7 | — | 29 |
| Willow, [HSO$_4$] | 39.1 | 3.4 | 0 | 0.8 | 0.9 | 3.6 | 0.5 | — | 52 |
| Pine | 45.8 | 2.5 | 12.0 | 2.6 | 3.4 | 25.5 | 1.3 | 4.3 | 0 |
| Pine, [MeCO$_2$] | 40.4 | 2.5 | 16.1 | 3.4 | 2.7 | 21.1 | 0.6 | — | 13 |
| Pine, [HSO$_4$] | 37.9 | 3.2 | 4.6 | 0 | 0 | 8.8 | 0.2 | — | 45 |

For both substrates, lignin and hemicellulose removal were more extensive after $[C_4C_1im][HSO_4]_{80\%}$ pretreatment than after treatment with $[C_2C_1im][MeCO_2]_{80\%}$. The degree of cellulose enrichment after $[C_4C_1im][HSO_4]_{80\%}$ pretreatment of willow was almost as good as the enrichment observed for *Miscanthus* pulp. A precipitate could be recovered from all samples. Significantly higher yields were obtained from the $[C_4C_1im][HSO_4]_{80\%}$ liquors. The glucose yields obtained via enzymatic saccharification are shown in FIG. 43. More than 80% of the original glucose was released from $[C_4C_1im][HSO_4]_{80\%}$ pretreated willow pulp, approaching the saccharification yields obtained from *Miscanthus* pretreated with this liquor. However, enzymatic saccharification of pine pulp only released up to 30% of the glucose; the type of ionic liquid playing a minor role. The generally higher yields obtained after $[C_4C_1im]$

[HSO$_4$]$_{80\%}$ pretreatment could be due to the improved lignin and hemicellulose removal by the hydrogen sulfate containing liquor, as observed for *Miscanthus*.

Example 24 Ionic Liquid Solvent Properties and Biomass Digestibility

We measured the Kamlet Taft polarity (as described in A. Brandt, J. P. Hallett, D. J. Leak, R. J. Murphy and T. Welton, *Green Chemistry*, 2010, 12, 672-679) of [C$_4$C$_1$im][HSO$_4$] and [C$_4$C$_1$im][MeSO$_3$] (Table 6), as it has not been reported in the literature. Three parameters are used to determine the strength of solvent solute interactions. The parameter α describes the hydrogen-bond acidity of the solvent, β the hydrogen-bond basicity and π* the polarisability. Our measurements showed that the β parameter of [C$_4$C$_1$im][HSO$_4$] is the same as the value for [C$_4$C$_1$im][MeSO$_4$]. The hydrogen-bond acidity is very different, in fact, the α value cannot be determined for [C$_4$C$_1$im][HSO$_4$], because it protonates one of the dye probes.

We would like to point out that the high glucose yields were achieved without complete solubilisation of the biomass. This is due to the relatively low β values of [C$_4$C$_1$im][MeSO$_4$], [C$_4$C$_1$im][HSO$_4$] and [C$_4$C$_1$im][MeSO$_3$], which do not enable cellulose solubilisation. The β parameters are lower than the values of [C$_4$C$_1$im][MeCO$_2$] (β=1.20), 1-butyl-3-methylimidazolium dimethyl phosphate, [C$_4$C$_1$im][Me$_2$PO$_4$], (β=1.12) and [C$_4$C$_1$im]Cl (β=0.83).[19] Although [C$_2$C$_1$im][MeCO$_2$] can dissolve cellulose when it is anhydrous, the presence of 20 vol % water prevents cellulose solubility.

TABLE 6

Kamlet-Taft parameters of selected ionic liquids used in this work.

| | α | β | π* |
|---|---|---|---|
| [C$_4$C$_1$im][MeSO$_3$] | 0.44 | 0.77 | 1.02 |
| [C$_4$C$_1$im][MeSO$_4$][19] | 0.55 | 0.67 | 1.05 |
| [C$_4$C$_1$im][HSO$_4$] | — | 0.67 | 1.09 |

We also attempted to correlate the glucose yields with the ionic liquids' hydrogen-bond basicity. While it is clear that the nature of the anion affects the saccharification yield, it could not be correlated with the ionic liquid's β value.

It has been demonstrated for the first time that the ionic liquids [C$_4$C$_1$im][HSO$_4$], [C$_4$C$_1$im][MeSO$_3$] and the ionic liquid mixture [C$_4$C$_1$im][MeSO$_4$]/[HSO$_4$] can be used to pretreat lignocellulosic biomass. These ionic liquids functioned effectively in the presence of significant quantities of water, eliminating the need for anhydrous conditions during pretreatment. Commercial [C$_2$C$_1$im][MeO$_2$] was also effective in the presence of 20 vol % water, but the saccharification yield was lower. Lignin and hemicellulose were solubilised during pretreatment, leaving behind a solid residue that was highly enriched in cellulose. The enzymatic saccharification of *Miscanthus* pulp pretreated at 120° C. with liquors containing 80 vol % ionic liquid resulted in glucose yields of ca. 90%. The hemicellulose was partially recovered with the solid and readily hydrolysable during enzymatic saccharification. However, a significant portion of the hemicellulose remained in the pretreatment liquor as sugar monomers and was partially converted dehydration products. The amount of furfurals generated during ionic liquid pretreatment arises from the acidity of the ionic liquid liquors. In the presence of 20 vol % water, treatment with [C$_4$C$_1$im]Cl and [C$_4$C$_1$im][OTf] had little effect on the biomass, showing that the anion of 1,3-dialkylimidazolium ionic liquids plays an important role in determining the effectiveness of ionic liquid pretreatment and the tolerance towards water. We could not find a correlation between the pretreatment effectiveness and the anion basicity, as previously found for cellulose solubility or wood chips swelling. While the enzymatic sugar release from the grass and hardwood pulps was very good, yields from softwood pulp were only moderate. Upon dilution with water, a precipitate was recovered that is likely to contain lignin as well as pseudo-lignin. This study also suggests that mono-alkylated imidazolium ionic liquids, such as [C$_4$Him][HSO$_4$], appear to be promising, industrially relevant alternatives to dialkylimidazolium ionic liquids.

Example 25 Effect of Acid: Base Ratio on Yield

In order to investigate the effect of the acid/base properties of the mono-alkylated imidazolium sulphate/hydrogen sulphate ILs in the biomass pre-treatment, a series of different ILs with [C$_4$Him] cation and different ratios of [HSO$_4$]/[SO$_4$] anions and/or a H$_2$SO$_4$ excess were prepared. The ILs were synthesised via the addition of different ratios of sulphuric acid over 1-butylimidazole in water (Table 7).

A solution of H$_2$SO$_4$ (95%) in water (3 mL water/mL H$_2$SO$_4$) was added dropwise to a solution of 1-butylimidazole (98.4%) in water (1 mL water/mL of 1-butylimidazole). The mixture was stirred at room temperature for several hours.

Once the reaction was completed, ILs were decoloured by the addition of charcoal and filtrated through neutral alumina. Water was then removed by heating at 50° C. for 48 h and ILs were obtained as colourless liquids at room temperature with high yields and purity. Structure and composition of ILs was confirmed by $^1$H-NMR, $^{13}$C-NMR, mass spectroscopy and elemental analysis. The final quantities of [C$_4$Him], [HSO$_4$], [SO$_4$] and H$_2$SO$_4$ present in the ILs prepared are shown in Table 8.

TABLE 7

Rates of H$_2$SO$_4$ and 1-butylimidazole employed in the ILs synthesis.

| IL | H$_2$SO$_4$ (eq.) | 1-butylimidazole (eq.) | Yield |
|---|---|---|---|
| [C$_4$HIm][HSO$_4$] + 50% H$_2$SO$_4$ | 1.5 (56.49 mL, 1006.8 mmol) | 1 (90 mL, 671.2 mmol) | 99% |
| [C$_4$HIm][HSO$_4$] + 1% H$_2$SO$_4$ | 1.01 (42.26 mL, 753 mmol) | 1 (100 mL, 746 mmol) | 96% |
| 1.01[C$_4$HIm]0.99[HSO$_4$]0.01[SO$_4$] | 1 (41.43 mL, 738 mmol) | 1.01(100 mL, 746 mmol) | 98% |

TABLE 7-continued

Rates of $H_2SO_4$ and 1-butylimidazole employed in the ILs synthesis.

| IL | $H_2SO_4$ (eq.) | 1-butylimidazole (eq.) | Yield |
|---|---|---|---|
| 1.25[$C_4$HIm]0.75[$HSO_4$]0.25[$SO_4$] | 1 (30.13 mL, 537 mmol) | 1.25 (90 mL, 671 mmol) | 98% |
| 1.5[$C_4$HIm]0.5[$HSO_4$]0.5[$SO_4$] | 1 (26.6 mL, 499.2 mmol) | 1.5 (100 mL, 748.8 mmol) | 99% |
| [$C_4$HIm]0.5[$SO_4$] | 1 (26.15 mL, 466 mmol) | 2 (125 mL, 932 mmol) | 99% |

TABLE 8

Amounts of [$C_4$Him], [$HSO_4$], [$SO_4$] and $H_2SO_4$ present in the ILs prepared.

| IL | [$C_4$HIm] (eq.) | [$HSO_4$] (eq.) | [$SO_4$] (eq.) | $H_2SO_4$ (eq.) |
|---|---|---|---|---|
| [$C_4$Him][$HSO_4$] + 50% $H_2SO_4$ | 1.00 | 1.00 | 0.00 | 0.50 |
| [$C_4$Him][$HSO_4$] + 1% $H_2SO_4$ | 1.00 | 1.00 | 0.00 | 0.01 |
| 1.01[$C_4$Him]0.99[$HSO_4$]0.01[$SO_4$] | 1.01 | 0.99 | 0.01 | 0.00 |
| 1.25[$C_4$Him]0.75[$HSO_4$]0.25[$SO_4$] | 1.25 | 0.75 | 0.25 | 0.00 |
| 1.5[$C_4$Him]0.5[$HSO_4$]0.5[$SO_4$] | 1.50 | 0.50 | 0.50 | 0.00 |
| [$C_4$Him]0.5[$SO_4$] | 2.00 | 0.00 | 1.00 | 0.00 |

The relative concentrations of acid and base were varied in the $C_4$Him $HSO_4$ system as described above. The saccharification yields relative to the glucose or hemicelluloses content in the untreated *Miscanthus*, were measured and are shown in FIGS. 44 and 45. The best results were obtained with a slight (1%) excess of the acid ($5^{th}$ column group from left), where a maximum glucose yield and a decent hemicelluloses yield was achieved already after 4 h. It seems that addition of a little acid significantly accelerates the pretreatment process, when other variable such as water content and temperature are kept constant. Too much acid seems to char the biomass and excess base increases the hemicelluloses yield slightly but also the time required until maximum glucose yield is achieved.

Example 26 Woodchip Grinding Energy

Pine wood chips (8 chips, size 8×7×7 mm, approx. 1.3 g) were placed in 5 mL of the pre-treatment liquid in a glass tube and heated to 90° C. in an oven for either 1 or 18 hours. The chips were then cooled and excess liquid removed from their surfaces with paper towel, then ground in an analytical grinder for 30 seconds. The power consumption of the grinder was determined using a power analyser. Energy saving (Table 9, FIG. 49) is calculated per gram of wood by subtracting the energy used by the grinder when empty and comparison to the energy used to grind dry wood.

TABLE 9

Woodchip grinding energy saving for various pretreatment methods relative to dry wood

| Liquid | Treatment Conditions | Energy saving relative to dry wood (%) |
|---|---|---|
| [bmim]$NTf_2$ | 90° C., 1 h | 75 |
| [bmim]$HSO_4$ | 90° C., 1 h | 59 |
| [bmim]$HSO_4$ + 20% $H_2O$ | 90° C., 1 h | 62 |
| [bmim]$HSO_4$ + 20% $H_2O$ | 90° C., 18 h | 37 |
| [bmim]OAc | 90° C., 1 h | 36 |
| [bmim]OAc + 20% $H_2O$ | 90° C., 1 h | 49 |
| silicone oil | 90° C., 1 h | 43 |
| silicone oil | 90° C., 18 h | 44 |
| PFPE Fomblin Y 06/6 | 90° C., 1 h | 43 |
| DMSO | 90° C., 1 h | 31 |
| Organosolv | 90° C., 1 h | 29 |

After grinding, samples were soaked overnight in 20 mL of an appropriate volatile solvent (in all cases methanol, except petroleum spirit used for silicone oil and perfluorohexane for Fomblin). They were then filtered, rinsed twice with 5 mL of the solvent and left to air-dry for at least 24 hours. The resulting dry powder was gravimetrically checked for significant quantities of residual treatment liquid. The powder was then passed through a nested column of sieves with decreasing pore sizes (2 mm-53 µm) by shaking on a vibratory sieve shaker for 8 minutes. The percentage weight of material retained by each sieve was measured, and from this data the log-normal distribution mass median diameter ($D_{50}$) was calculated, i.e. the particle size that 50% of the sample is smaller than by mass. (Table 10). It is used herein as a measure of the wood powder's average particle size, and was calculated by linear interpolation using the following Equation.

$$D_{50} = 10^{\left[(log x_2 - log x_1) \times \left(\frac{50 - y_1}{y_2 - y_1}\right) + log x_1\right]}$$

Where $x_1$ and $x_2$ are the pore sizes of the sieves which allowed just under and just over 50% of the sample to pass through by weight, respectively, and $y_1$ and $y_2$ are the percentages of material passing through those sieves.

TABLE 10

Median particle size ($D_{50}$) of wood powder obtained by grinding woodchips pretreated in various ways

| Liquid | Treatment Conditions | $D_{50}$ (µm) |
|---|---|---|
| no liquid | 90° C., 1 h | 789 |
| [bmim]$NTf_2$ | 90° C., 1 h | 219 |
| [bmim]$HSO_4$ | 90° C., 1 h | 223 |
| [bmim]$HSO_4$ + 20% $H_2O$ | 90° C., 1 h | 392 |
| [bmim]$HSO_4$ + 20% $H_2O$ | 90° C., 18 h | 457 |
| [bmim]OAc | 90° C., 1 h | 416 |

TABLE 10-continued

Median particle size ($D_{50}$) of wood powder obtained by grinding woodchips pretreated in various ways

| Liquid | Treatment Conditions | $D_{50}$ (μm) |
|---|---|---|
| [bmim]OAc + 20% $H_2O$ | 90° C., 1 h | 466 |
| silicone oil | 90° C., 1 h | 318 |
| silicone oil | 90° C., 18 h | 302 |
| PFPE Fomblin Y 06/6 | 90° C., 1 h | 243 |
| DMSO | 90° C., 1 h | 458 |
| Organosolv | 90° C., 1 h | 826 |

Saccharification 150 mg of wood powder was taken from a certain particle size fraction of each sample.

For comparison, woodchips that were pretreated but not ground were also prepared. This was added to a buffer solution containing cellulose-hydrolysing enzymes and incubated for 96 hours at 50° C. The enzyme preparations used were Celluclast, a cellulase mix from *Trichoderma reesei*, and Novozyme 188 β-glucosidase which can also hydrolyse xylan due to its hemicellulolytic activity. 60 μL of each preparation was used. The amount of glucose and hemicellulose present after this was determined using HPLC (Table 11, FIG. 50). Sugar yields are given as a percentage of each sample's dried-weight.

TABLE 11

Sugar yields from enzymatically treated wood powder ground from woodchips pretreated in different ways, as a percentage of sample dried-weight

| No. | Liquid | Treatment Conditions | Particle Size (μm) | Glucose Yield (%) | Hemi-cellulose Yield (%) |
|---|---|---|---|---|---|
| 1 | no liquid | 90° C., 1 h | 180-850 | 2.83 | 0.93 |
| 2 | DMSO | 90° C., 1 h | 180-850 | 3.34 | 0.80 |
| 3 | Organosolv | 90° C., 1 h | 180-850 | 2.52 | 0.80 |
| 4 | PFPE Fomblin Y 06/6 | 90° C., 1 h | 180-850 | 1.90 | 0.63 |
| 5 | silicone oil | 90° C., 1 h | 180-850 | 1.50 | 0.60 |
| 6 | silicone oil | 90° C., 18 h | 180-850 | 1.87 | 0.72 |
| 7 | silicone oil | 90° C., 18 h | 53-150 | 2.91 | 1.02 |
| 8 | [bmim]$HSO_4$ | 90° C., 1 h | 180-850 | 1.81 | 0.53 |
| 9 | [bmim]$HSO_4$ + 20% $H_2O$ | 90° C., 1 h | 180-850 | 0.73 | 0.37 |
| 10 | [bmim]$HSO_4$ + 20% $H_2O$ | 90° C., 18 h | 180-850 | 2.96 | 3.10 |
| 11 | [bmim]$HSO_4$ + 20% $H_2O$ | 90° C., 18 h | 53-150 | 3.65 | 2.93 |
| 12 | [bmim]$HSO_4$ + 20% $H_2O$ | 90° C., 18 h | unground | 1.16 | 2.20 |
| 13 | [bmim]OAc | 90° C., 1 h | 180-850 | 7.53 | 2.30 |
| 14 | [bmim]OAc + 20% $H_2O$ | 90° C. 1 h | 180-850 | 2.59 | 0.90 |
| 15 | [bmim]OAc + 20% $H_2O$ | 90° C., 18 h | unground | 0.75 | 0.41 |
| 16 | [bmim]$NTf_2$ | 90° C., 1 h | 180-850 | 2.02 | 0.77 |

The invention claimed is:

1. A method of treating a biomass to dissolve the lignin therein, but not the cellulose comprising:
   (a) contacting the lignocellulose biomass with a composition comprising an ionic liquid and 20-40% v/v water to dissolve lignin and produce a cellulose pulp, wherein the ionic liquid comprises a cation and an anion selected from $C_{1-20}$ alkyl sulfate [AlkylSO$_4$]$^-$, $C_{1-20}$ alkylsulfonate [AlkylSO$_3$]$^-$, hydrogen sulfate [HSO$_4$]$^-$, hydrogen sulphite [HSO$_3$]$^-$, dihydrogen phosphate [H$_2$PO$_4$]$^-$, and hydrogen phosphate [HPO$_4$]$^{2-}$, and wherein the contacting is performed such that the majority of the cellulose in the lignocellulose biomass remains solid; and
   (b) separating the ionic liquid-containing composition from the cellulose pulp produced in (a).

2. The method as claimed in claim 1 wherein said cation is a protic cation.

3. The method as claimed in claim 1 wherein the anion is selected from [MeSO$_4$]$^-$, [HSO$_4$]$^-$ and [MeSO$_3$]$^-$.

4. The method as claimed in claim 1 wherein the cation in the ionic liquid is selected from an imidazolium derivative, a pyridinium derivative and an ammonium derivative.

5. The method as claimed in claim 1 wherein the cation is selected from 1-butyl-3-methylimidazolium [C$_4$C$_1$im]$^+$, 1-ethyl-3-methylimidazolium [C$_2$C$_1$im]$^+$, 1-methylimidazolium [C$_1$Him]$^+$ and 1-butylimidazolium [C$_4$Him]$^+$.

6. The method as claimed in claim 1 wherein said ionic liquid is selected from 1-butyl-3-methylimidazolium methyl sulfate [C$_4$C$_1$im][MeSO$_4$], 1-butyl-3-methylimidazolium hydrogen sulfate [C$_4$C$_1$im][HSO$_4$], 1-butyl-3-methylimidazolium methanesulfonate [C$_4$C$_1$im][MeSO$_3$], and 1-butyl-imidazolium hydrogen sulfate [C$_4$Him][HSO$_4$].

7. The method as claimed in claim 1 wherein the composition further comprises 0.01-20% v/v acid.

8. The method as claimed in claim 1 wherein the lignocellulose biomass is contacted with the composition at a temperature in the range of 100-160° C.

9. The method as claimed in claim 1 wherein the lignocellulose biomass is contacted with the composition for a time in the range of 1-22 hours.

10. The method as claimed in claim 1 wherein the biomass is contacted with the composition prior to mechanical processing.

11. The method as claimed in claim 1 wherein the biomass is contacted with the composition after mechanical processing.

12. The method as claimed in claim 1 further comprising the step of washing the pulp with an organic solvent which is miscible with the composition.

13. The method as claimed in claim 12 further comprising
   (c) adding an anti-solvent to the ionic liquid obtained in (b) to precipitate out the dissolved lignin; and
   (d) separating the precipitated solid from the anti-solvent/ionic liquid.

14. The method as claimed in claim 13 further comprising
   (e) removing the anti-solvent from the ionic liquid obtained in (d).

15. The method as claimed in claim 13 wherein the anti-solvent is water.

16. A process according to claim 11, further comprising subjecting the cellulose pulp to enzymatic hydrolysis to form glucose.

17. The method as claimed in claim 1 wherein the contacting is performed such that at least 90% of the cellulose in the lignocellulose biomass remains solid.

18. The method as claimed in claim 1 wherein the contacting is performed such that at least 95% of the cellulose in the lignocellulose biomass remains solid.

19. The method as claimed in claim 1, wherein the ionic liquid comprises a cation and an anion selected from $C_{1-20}$ alkyl sulfate [AlkylSO$_4$]$^-$ and hydrogen sulfate [HSO$_4$]$^-$.

* * * * *